(12) United States Patent
Patterson et al.

(10) Patent No.: US 8,057,424 B2
(45) Date of Patent: *Nov. 15, 2011

(54) LOOP-TIP CATHETER

(75) Inventors: Ryan C. Patterson, Flagstaff, AZ (US);
Kelly B. Powers, North Salt Lake, UT (US); John A. Zawacki, Shorewood, MN (US); Ryan Moehle, Salt Lake City, UT (US); Jeff Kraus, Los Gatos, CA (US)

(73) Assignee: C. R. Bard, Inc., Murray Hill, NJ (US)

( * ) Notice: Subject to any disclaimer, the term of this patent is extended or adjusted under 35 U.S.C. 154(b) by 124 days.

This patent is subject to a terminal disclaimer.

(21) Appl. No.: 12/334,879

(22) Filed: Dec. 15, 2008

(65) Prior Publication Data

US 2009/0093748 A1 Apr. 9, 2009

Related U.S. Application Data

(63) Continuation of application No. 11/072,052, filed on Mar. 3, 2005, now Pat. No. 7,465,286.

(60) Provisional application No. 60/549,688, filed on Mar. 3, 2004.

(51) Int. Cl.
*A61M 3/00* (2006.01)
(52) U.S. Cl. ........................................................ 604/43
(58) Field of Classification Search .................. 604/5.01, 604/6.16, 8, 19, 27, 28, 39, 43, 104, 105, 604/264–266, 271, 507, 508, 523; 600/433; 606/108

See application file for complete search history.

(56) References Cited

U.S. PATENT DOCUMENTS

| | | | |
|---|---|---|---|
| 2,286,462 | A | 6/1942 | Chaffin |
| 2,492,384 | A | 12/1949 | Kaslow |
| 2,531,793 | A | 11/1950 | Sulek |
| 4,681,564 | A | 7/1987 | Landreneau |
| 5,395,316 | A | 3/1995 | Martin |
| 5,509,900 | A | 4/1996 | Kirkman |
| 5,555,883 | A | 9/1996 | Avitall |
| 5,702,365 | A | 12/1997 | King |
| 5,713,863 | A | 2/1998 | Vigil et al. |
| 5,738,666 | A | 4/1998 | Watson et al. |
| 5,800,414 | A | 9/1998 | Cazal |
| 6,048,332 | A | 4/2000 | Duffy et al. |
| 6,206,849 | B1 | 3/2001 | Martin et al. |

(Continued)

FOREIGN PATENT DOCUMENTS

EP 0417865 A1 3/1991
(Continued)

OTHER PUBLICATIONS

Jun. 20, 2005 PCT Written Opinion for PCT/US2005/006881 filed Mar. 3, 2005.

(Continued)

*Primary Examiner* — Nicholas Lucchesi
*Assistant Examiner* — Nathan R Price
(74) *Attorney, Agent, or Firm* — Rutan & Tucker, LLP

(57) ABSTRACT

A hemodialysis catheter, including an elongate body with an outer wall enclosing an arterial lumen and a venous lumen, and a method of making same. A loop extends from a distal end of the body and defines an enclosed opening. An arterial inlet in fluid communication with the arterial lumen, and a venous outlet in fluid communication with the venous lumen, are positioned on the loop.

10 Claims, 30 Drawing Sheets

U.S. PATENT DOCUMENTS

| | | | |
|---|---|---|---|
| 6,280,414 | B1 | 8/2001 | Shah et al. |
| 6,558,349 | B1 | 5/2003 | Kirkman |
| 6,605,061 | B2 | 8/2003 | VanTassel et al. |
| 6,620,139 | B1 | 9/2003 | Plicchi et al. |
| 6,780,175 | B1 | 8/2004 | Sachdeva et al. |
| 6,942,641 | B2 | 9/2005 | Seddon |
| 7,276,043 | B2 | 10/2007 | Heath et al. |
| 7,465,286 | B2 * | 12/2008 | Patterson et al. ............... 604/43 |
| 2001/0049500 | A1 | 12/2001 | VanTassel et al. |
| 2002/0068897 | A1 | 6/2002 | Jenkins et al. |
| 2003/0144623 | A1 | 7/2003 | Heath et al. |

FOREIGN PATENT DOCUMENTS

| | | |
|---|---|---|
| WO | WO 03/068303 A2 | 8/2003 |
| WO | WO 03/094764 A1 | 11/2003 |
| WO | WO 2004/002563 | 1/2004 |
| WO | WO 2004/100813 | 11/2004 |

OTHER PUBLICATIONS

Jun. 20, 2005 PCT Search Report for PCT/US2005/006881 filed Mar. 3, 2005.

Jun. 6, 2006 PCT International Preliminary Report on Patentability for PCT/US2005/006881 filed Mar. 3, 2005.

Nov. 16, 2009 European Office Action issued for EP Application No. 05 724 426.1 filed Mar. 3, 2005.

Mar. 23, 2006 Non-final Office Action in U.S. Appl. No. 11/072,052, filed Mar. 3, 2005.

Jul. 28, 2006 Final Office Action in U.S. Appl. No. 11/072,052, filed Mar. 2, 2005.

Jun. 27, 2008 Final Office Action in U.S. Appl. No. 11/072,052, filed Mar. 3, 2005.

Jan. 5, 2007 Non-final Office Action in U.S. Appl. No. 11/072,052, filed Mar. 3, 2005.

* cited by examiner

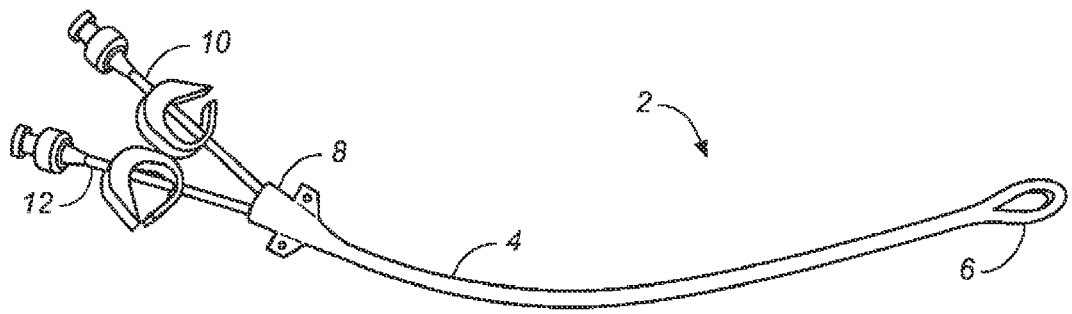
FIG. 1
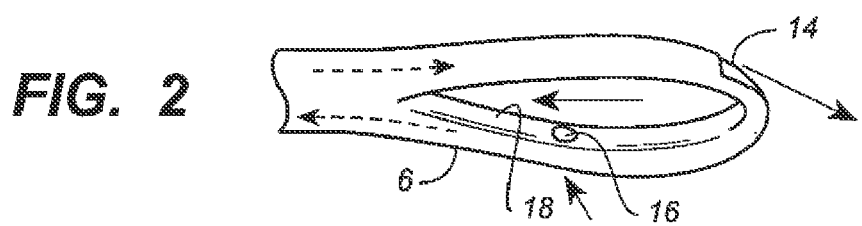
FIG. 2
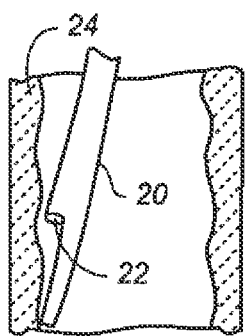
FIG. 3A
(PRIOR ART)
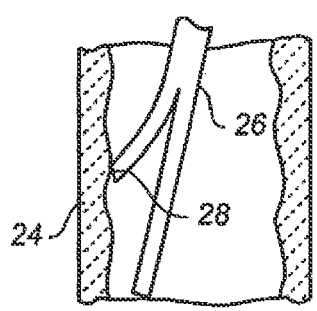
FIG. 3B
(PRIOR ART)
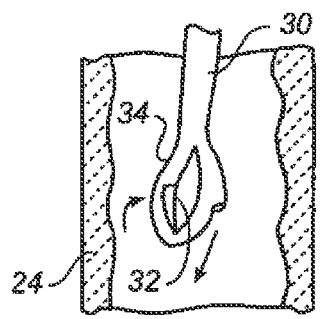
FIG. 3C
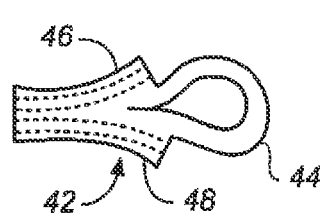
FIG. 4A
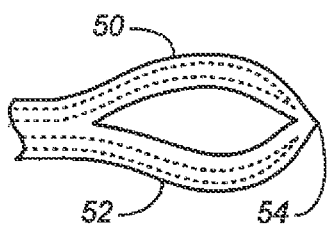
FIG. 4B
FIG. 4C

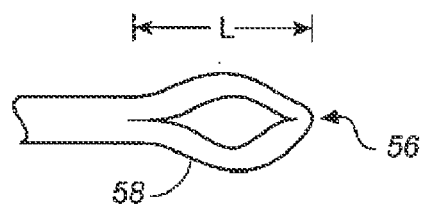
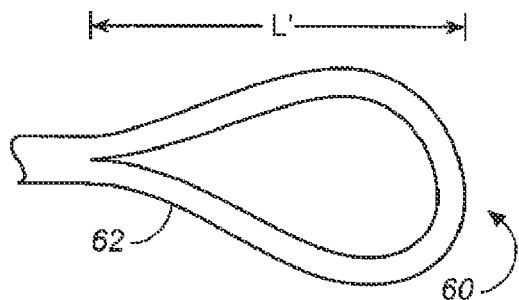
*FIG. 5A*  *FIG. 5B*
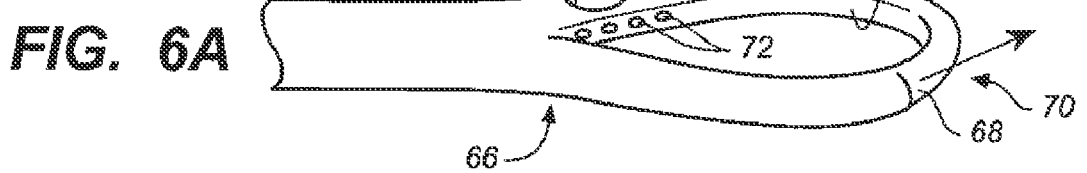
*FIG. 6A*
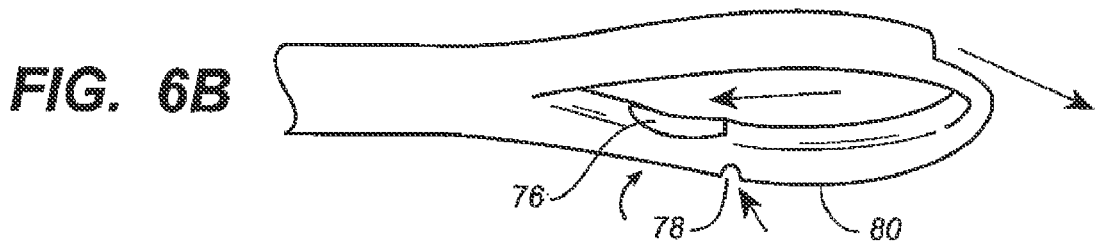
*FIG. 6B*
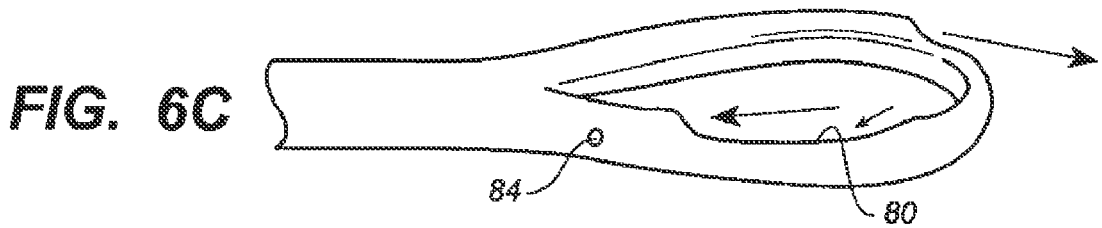
*FIG. 6C*
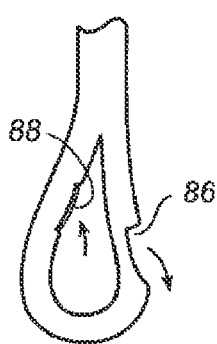 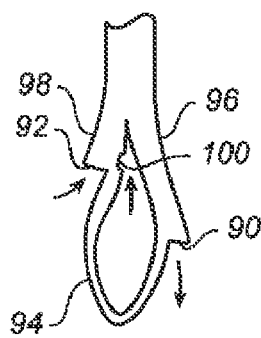 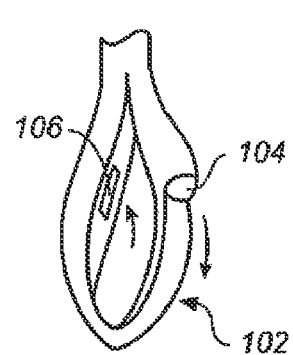 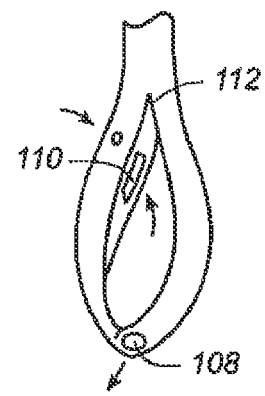
*FIG. 6D*   *FIG. 6E*   *FIG. 6F*   *FIG. 6G*

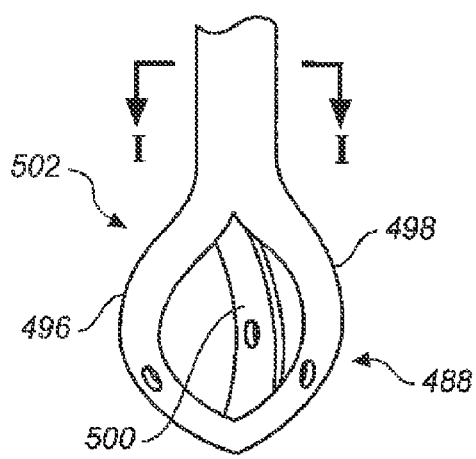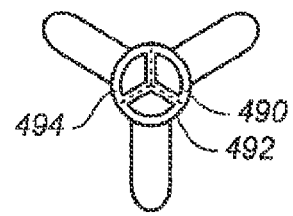
FIG. 42        FIG. 43
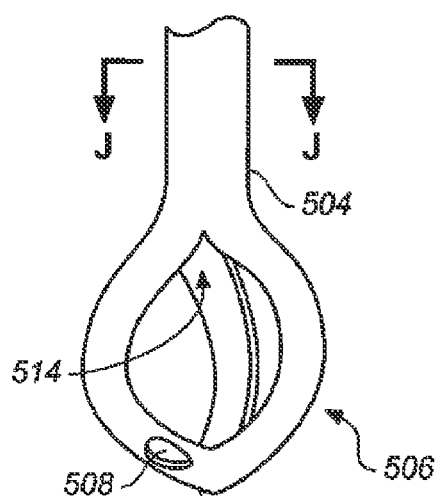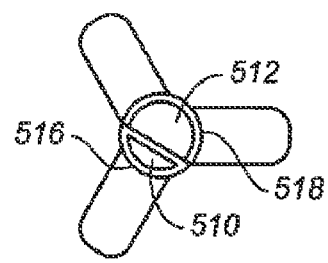
FIG. 44A        FIG. 44B
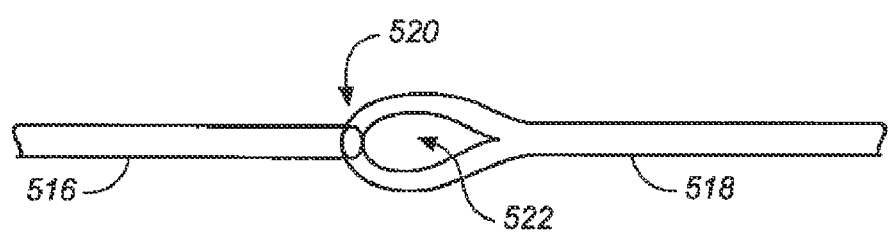
FIG. 45

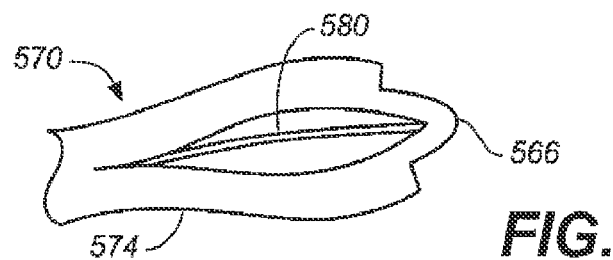
FIG. 51
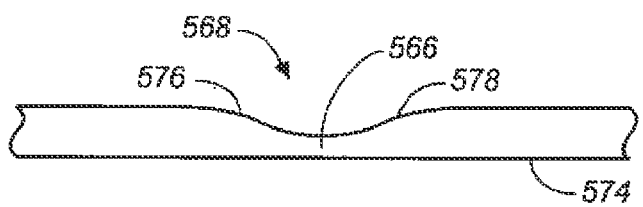
FIG. 52
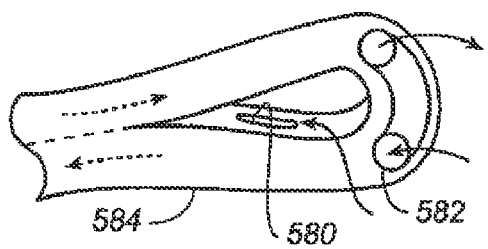
FIG. 53
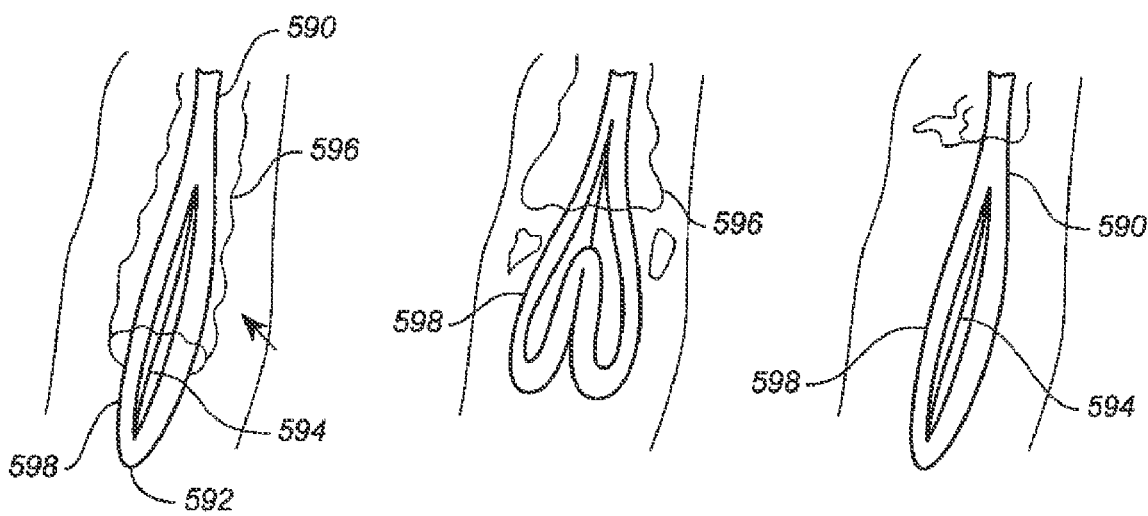
FIG. 54A  FIG. 54B  FIG. 54C

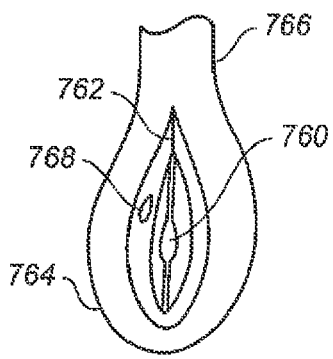 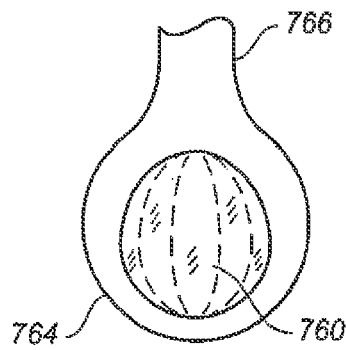 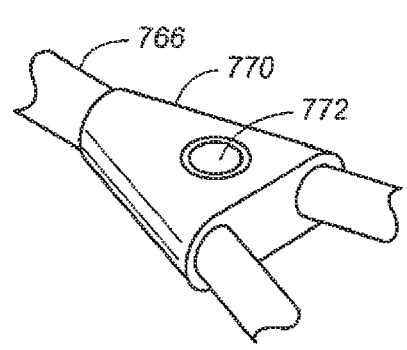
FIG. 77A  FIG. 77B  FIG. 78
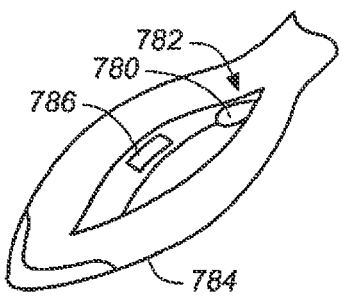 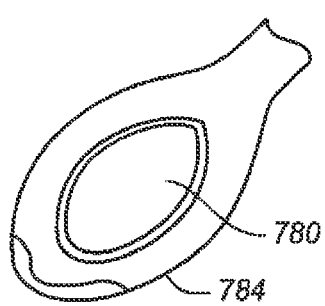
FIG. 79A  FIG. 79B
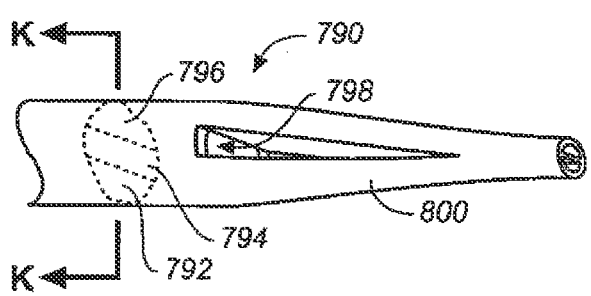 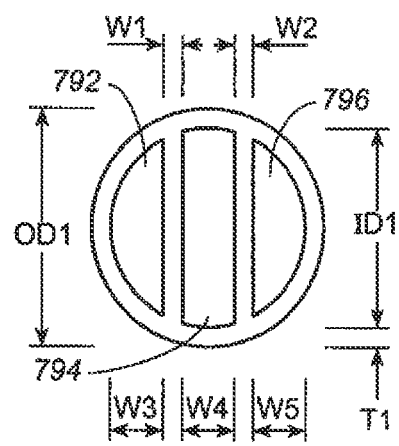
FIG. 80  FIG. 81A
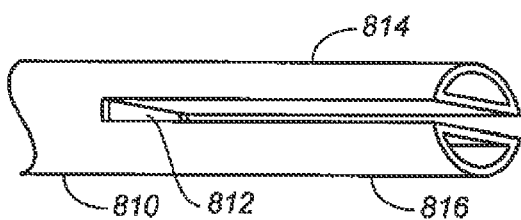 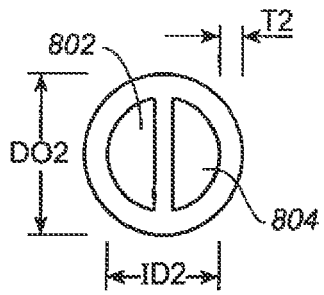
FIG. 82  FIG. 81B

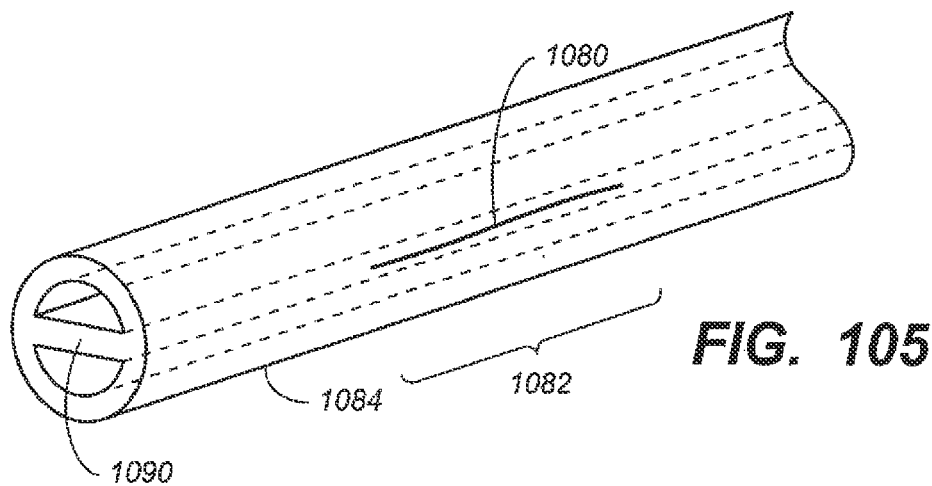
FIG. 105
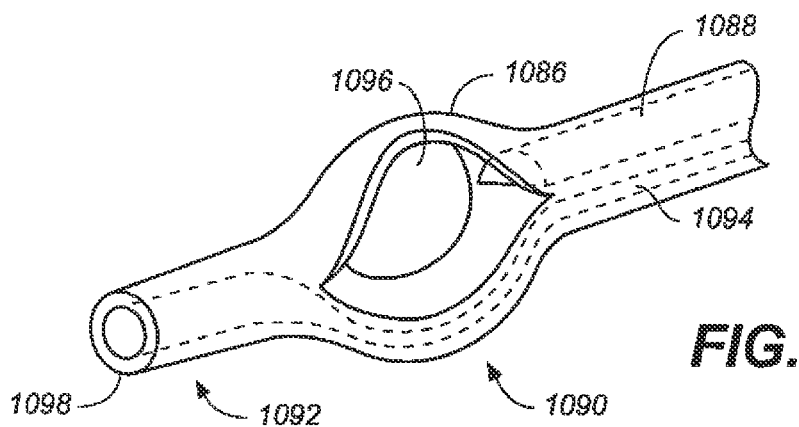
FIG. 106
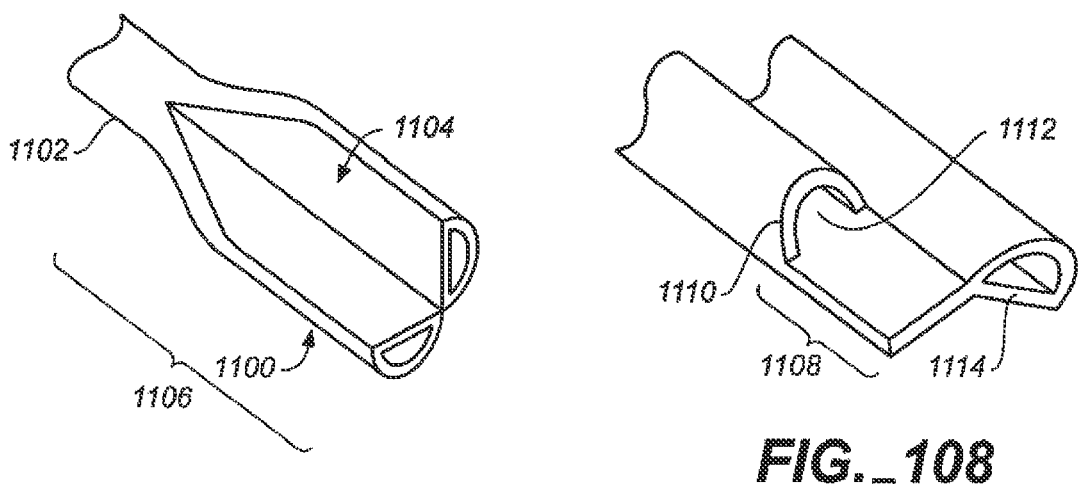
FIG. 107
FIG. 108
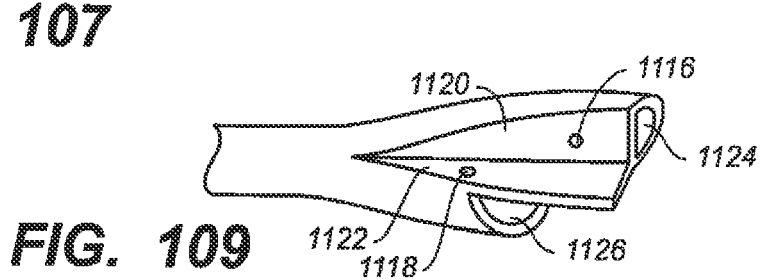
FIG. 109

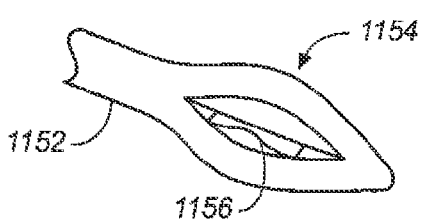
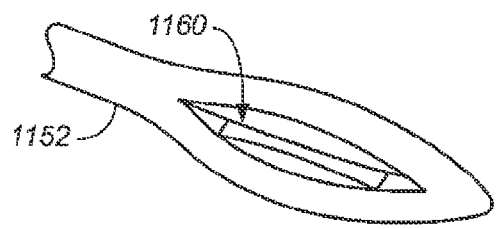
FIG. 112A    FIG. 112B
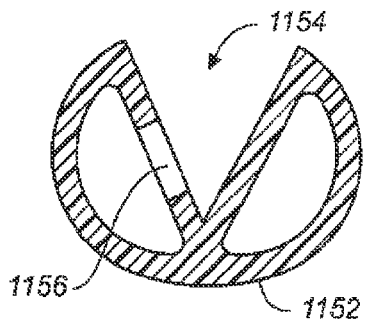
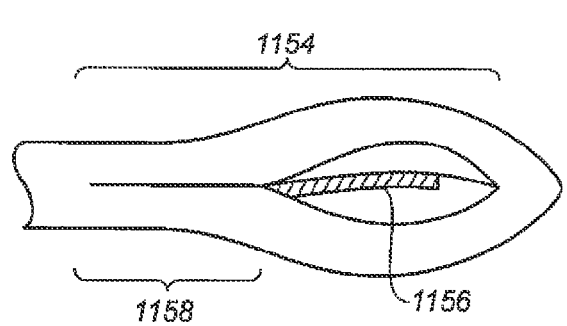
FIG. 113    FIG. 114
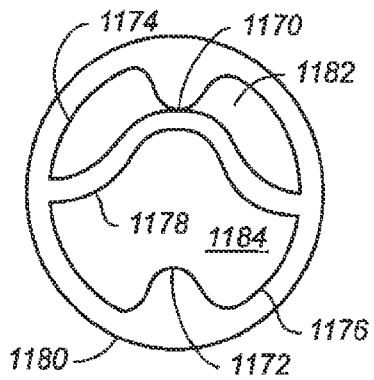
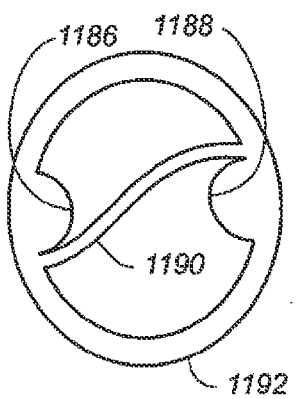
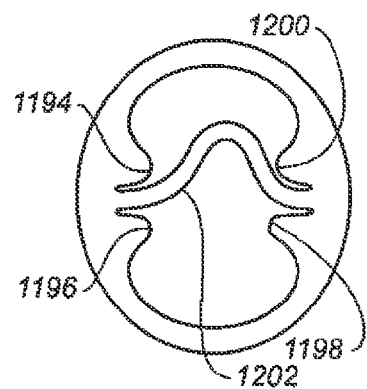
FIG. 115A    FIG. 115B    FIG. 115C
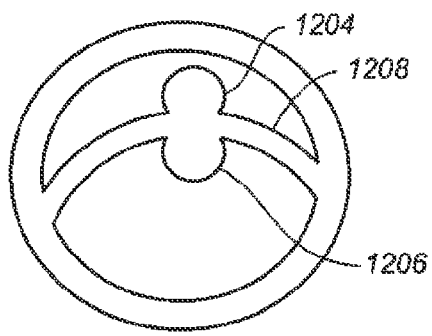
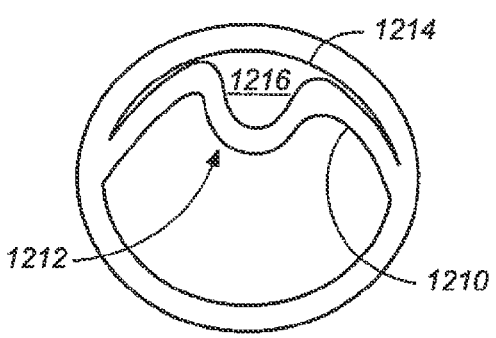
FIG. 115D    FIG. 115E

LOOP-TIP CATHETER

CROSS-REFERENCE TO RELATED APPLICATIONS

This application is a continuation of U.S. patent application Ser. No. 11/072,052, filed Mar. 3, 2005, now U.S. Pat. No. 7,465,286, which claims the benefit of priority to U.S. Provisional Patent Application No. 60/549,688, filed Mar. 3, 2004, each of which is incorporated herein by reference in its entirety.

BACKGROUND OF THE INVENTION

Multi-lumen catheters are used for the purpose of creating two or more separate fluid pathways, such as in hemodialysis applications. A primary goal of hemodialysis access is to provide a reliable and effective means of dialysis, which means that a sufficient volume of blood over a period of time must be removed from and returned to the patient. Because the contaminated and cleansed blood must be kept separate for an effective dialysis procedure, a dual lumen catheter is generally used. These dual lumen catheters are usually configured so that there is a shorter lumen that aspirates blood from a blood vessel of a patient to a dialysis machine where it is processed for the removal of toxins, and a longer lumen that infuses the purified blood to the patient. The shorter lumen utilized for aspiration is generally referred to as the "arterial lumen," while the longer lumen utilized for infusion is generally referred to as the "venous lumen." The reason for the different lengths is to minimize co-mingling of aspirated and infused blood.

The primary problems occurring in dual lumen dialysis catheters are blood clotting (thrombosis) and fibrin (the protein formed during normal blood clotting that is the essence of the clot) sheath formation. Thrombus and fibrin sheath formation can occlude distal tips of the dialysis catheter lumens, resulting in loss of catheter function when such an occlusion prevents blood flow. This typically occurs initially in the arterial lumen used for aspiration of blood from a patient. Other common problems related to dual lumen dialysis catheters include, (1) the arterial lumen "sucking" against the vessel wall, in which the arterial lumen openings become fully occluded by the patient's vasculature, and (2) recirculation of cleansed blood, which necessarily lowers the efficiency of a dialysis procedure.

Therefore, it would be desirable to provide an improved multi-lumen catheter that would overcome performance and manufacturability concerns present in currently offered products. It would also be desirable to provide designs and methods for making a multi-lumen catheter for enhanced overall functionability thereof.

SUMMARY OF THE INVENTION

Accordingly, a multi-lumen catheter (e.g., a dialysis catheter) is described, which addresses one or more of the common catheter design issues, such as flow performance, insertion ease, and longevity issues. One variation of the multi-lumen catheter includes a unique design on the distal end thereof, which will protect the arterial inlet and prevent sidewall occlusion. Another variation of the multi-lumen catheter has a catheter body that houses wires, mandrels or balloons to improve patency. The distal portion of such a catheter can be configured such that it is atraumatic to the vessel walls, and capable of minimizing recirculation rates. Another variation of the multi-lumen catheter can be easily manufactured. Another variation of the multi-lumen catheter provides resistance to fibrin sheath formation and/or is configured such that fibrin sheath removal is possible without removing the catheter from its implanted location. Still another variation of the multi-lumen catheter is introduced into a vessel with minimal risk of air embolism. Another variation of the multi-lumen catheter allows the user to seal the arterial inlet between dialysis sessions.

In one aspect of the invention, the tip of the catheter incorporates a loop-like structure. The catheter can be a single lumen catheter or includes a plurality of lumens. In one variation, the loop structure is designed to mechanically separate the channel outlets/inlets at the tip of the multi-lumen catheter to minimize vessel trauma, to protect the arterial inlet and to prevent sidewall occlusion. In another variation, a displacement mechanism is provided within the distal portion of the catheter for actively breaking or removing deposits (e.g., fibrin sheath, clots, etc.) from the distal end of the catheter. For example, a wire or mandrel can be embedded within the catheter for twisting or displacing the distal portion of the loop-tip catheter. In another example, a balloon is positioned within the loop structure at the distal portion of the catheter for expanding the tip of the catheter. The displacement mechanism may also be implemented for reconfiguring the catheter tip structure to protect a lumen opening on the loop structure. Wires, mandrels, balloons, etc., may also be utilized to improve patency, and/or to minimize recirculation. Furthermore, the loop structure may be flattened, compressed, contracted, or otherwise reduced in size to facilitate placement within an introducer sheath for introduction into the patient's circulatory system. The contraction of the distal loop-tip may also reduce the risk of air embolism.

The loop structure may be constructed in a number of different ways, including, but not limited to: 1) extruding a single lumen tube and folding the tube onto itself, bonding the proximal and medial regions thereof, while leaving the distal region unbonded; 2) extruding two tubes and bonding together along a majority of the length thereof, leaving only a distal portion unbonded to form a loop; and 3) extruding a multiple lumen tube, cutting the outer walls at the distal end of the tube, and manipulating the walls to form one or more loop structures. Various other improvements for the design and manufacture of a multi-lumen catheter are also disclosed herein.

The loop-tip can be designed with various configurations. For example, one configuration of the loop-tip design permits the placement of two single lumen catheters as a coupled unit, without the need to place the catheters separately. The bowed/looped tip may prevent arterial suction and acts to ensure that the side holes are oriented appropriately to maximize flow performance. Moreover, the tip may prevent fibrin formation due to its dynamic movement during dialysis procedures. The loop-tip can be configured to facilitate an "over-the-guidewire" placement, and can also be coil reinforced to improve kink and pinch resistance.

To facilitate insertion, one variation is provided with a disposable mandrel for insertion into the catheter lumen to straighten the tip, resulting in a flattening of the loop configuration. Another configuration of the loop-tip design places the arterial and/or venous inlet/exit sites along the length of the loop. The inlet/exit sites may be positioned in locations within the central vein (i.e., superior vena cava (SVC) or right atrium) that may improve the efficiency of the dialyses process. To minimize recirculation, the arterial and venous openings may be formed on different sides of the loop-tip and/or may be staggered along the length thereof.

These and other embodiments, features and advantages of the present invention will become more apparent to those skilled in the art when taken with reference to the following more detailed description of the invention in conjunction with the accompanying drawings that are first briefly described.

BRIEF DESCRIPTION OF THE DRAWINGS

FIG. 1 illustrates one variation of a dual lumen loop-tip catheter.

FIG. 2 is an expanded view of the distal portion of the loop-tip catheter of FIG. 1. The arrows illustrate the direction of fluid flow for one possible application, where the catheter is utilized for hemodialysis.

FIG. 3A illustrates a typical hemodialysis catheter with staggered lumen openings suctioning against the wall of a blood vessel.

FIG. 3B illustrates a typical slip-tip hemodialysis catheter suctioning against the wall of a blood vessel.

FIG. 3C illustrates one variation of a loop-tip catheter utilized in a blood vessel for hemodialysis application. The loop structure prevents the arterial inlet from suctioning against the vessel wall.

FIGS. 4A-4B illustrates various examples of loop-tip configurations. In FIG. 4A one variation including a loop extending distally from the tip of a dual lumen catheter is shown.

FIG. 4B illustrates another example where the distal tip of the dual lumen catheter is split as it extends to form the loop.

FIG. 4C illustrates yet another variation where the dual lumens of the catheter extends into the loop section at the distal end of the catheter.

FIG. 5A illustrates one variation of a loop-tip with a short loop length. In this variation, the loop is configured to kink at the distal end of the catheter.

FIG. 5B illustrates another variation of a loop-tip with a long loop length. In this variation, the loop forms a semi-oval shape and does not have a kink at the distal tip.

FIGS. 6A-6G illustrate that loop-tip catheters with varying designs can be configured by changing the configurations and positions of outlets and inlets along the circumference of the loop.

FIG. 42 illustrates another variation of a triple loop-tip catheter. In this example, two of the loops are configured with outwardly facing lumen openings, while a third loop supports an inwardly facing lumen opening.

FIG. 43 illustrates a cross-sectional view of the shaft of the catheter of FIG. 42. The cross-section is taken at I-I, as shown in FIG. 42.

FIG. 44A illustrates one variation of a loop-tip catheter with three legs forming the loop portion of the catheter. In this example, one of the three legs has a built-in lumen.

FIG. 44B is a cross-sectional view showing the two lumens inside the catheter of FIG. 44A. The cross-section is taken at J-J, as shown in FIG. 44A.

FIG. 45 illustrates one method of fabricating a three-leg loop by connecting a C-shaped extrusion to a D-shaped catheter, and then folding the C-shaped extrusion over the D-shaped catheter.

In FIG. 46A the wire is advanced distally to force the loop to collapse towards the axis of the catheter.

FIG. 51 illustrates another variation of the loop-tip catheter with an integrated control wire. In this example, the tubing cut-away is positioned over the distal tip portion of the catheter, such that the tip of the catheter has a low profile for easy insertion into a narrow opening.

FIG. 52 shows a catheter with a tapered cut-away zone, such that the resulting loop-tip catheter would have a tapered profile at the distal tip.

FIG. 53 shows a loop-tip catheter configured from a catheter with a tapered cut-away zone, as shown in FIG. 52.

FIGS. 54A-54C illustrate the built-in contraction mechanism in a loop-tip catheter being utilized to remove fibrin built-up around the distal portion of the implanted catheter.

As shown in FIG. 57, the control shaft comprises a flexible rod with a lumen for delivering fluids or medications to the distal end of the catheter.

FIG. 77A illustrates a variation of loop-tip catheter including a balloon positioned within the loop for covering the arterial inlet. In this example the balloon is positioned within the center opening of the loop.

FIG. 77B illustrates the balloon in the loop-tip catheter of FIG. 77A in an inflated condition.

FIG. 78 illustrates an example implementation where a bifurcation including an access port is provided for connection to a loop-tip catheter with an integrated balloon. The port on the bifurcation allows the user to access a channel that is in fluid communication with the balloon.

FIG. 79A illustrates another variation where the balloon integrated within the loop of the loop-tip catheter comprises a diaphragm positioned on an inner circumferential surface of the loop.

FIG. 79B shows the diaphragm in the loop-tip catheter of FIG. 79A in an inflated condition.

FIG. 80 illustrates another variation of a loop-tip catheter. In this example, the catheter comprises three lumens, and two of the lumens extend distally to exit at the tip of the catheter.

FIG. 81A is a cross-sectional view of the shaft of the catheter from FIG. 80. The cross-section is taken at K-K, as shown in FIG. 80.

FIG. 81B shows the distal tip of the catheter of FIG. 80. As shown, the distal tip of the catheter comprises two lumen openings.

FIG. 82 illustrates an exemplary method of utilizing a triple lumen catheter to fabricate a loop-tip catheter shown in FIG. 80.

FIG. 83A shows the loop in a contracted state.

FIG. 88B is a cross-sectional view, illustrating one variation where the loop portion of the loop-tip catheter includes a continuous lumen, which is in fluid communication with the two lumens extending down the length of the catheter shaft.

FIG. 88C is a cross-sectional view illustrating another variation where the two lumens extending down the shaft of the catheter terminates within the loop portion. The two lumens functions independently and are not in fluid communication with each other.

FIG. 89 illustrates another loop-tip catheter design where the loop portion comprises silicone while the shaft portion of the catheter comprises polyurethane.

FIG. 90 illustrates another approach to configure a catheter with a silicone loop on the distal end of a polyurethane shaft.

FIG. 91 illustrates an adaptor implemented over a loop-tip catheter with a slit-valve to allow self-flushing of the catheter lumen.

FIG. 92A illustrates an adaptor configured to couple to the bifurcating branching at the proximal end of a dual lumen loop-tip catheter for simultaneous infusion of fluids through both of the lumens.

FIG. 92B illustrates another variation of a hub adaptor configured to support both infusion and flushing operations.

Figure 92A:
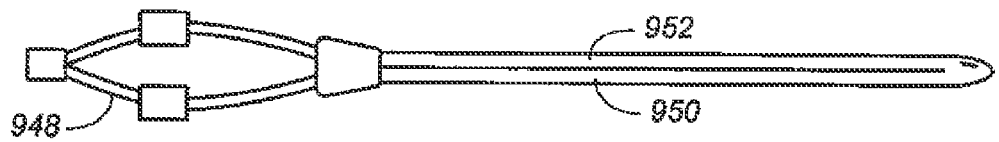
Figure 92B:
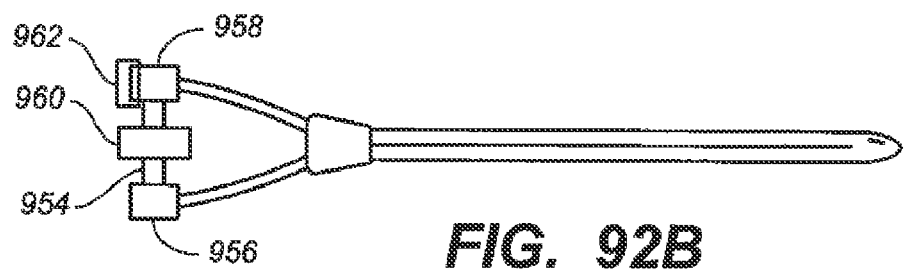
Figure 92C:
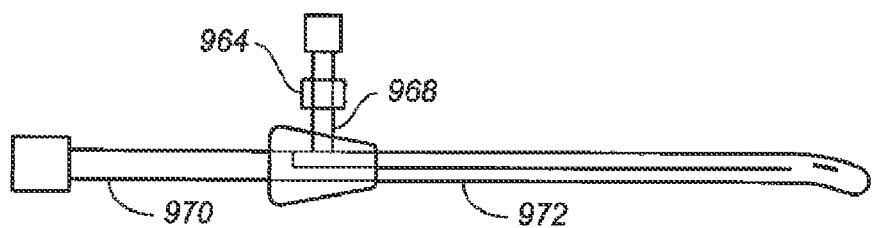

FIG. 92C illustrates another configuration where a loop-tip catheter is configured to allow self-flushing capability. An exit port connected to one of the two lumens can be closed to allow fluid infusion into the body of the patient through an input port. The exit port can be opened to allow the user to flush the catheter.

Figure 93:
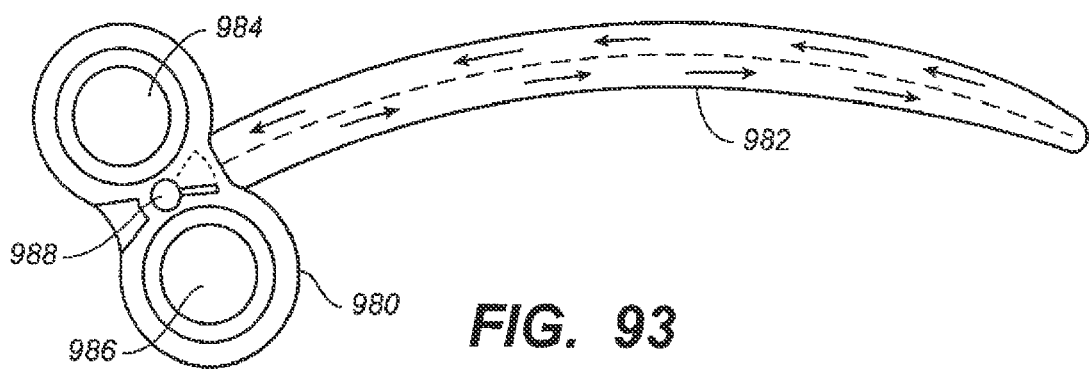

FIG. 93 illustrates another variation where the loop-tip catheter is implemented with a septum port for accessing the catheter after the implantation of the catheter assembly.

Figure 94A:
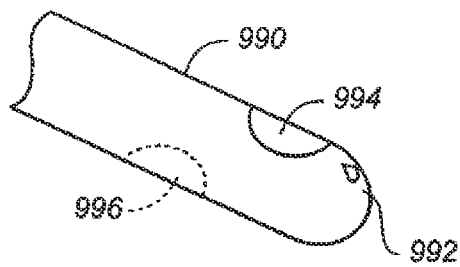

FIG. 94A illustrates yet another variation of a loop-tip catheter where a loop is configured at the tip of the catheter to allow the user to couple a tunneler or other medical instruments to the distal end of the catheter.

Figure 94B:
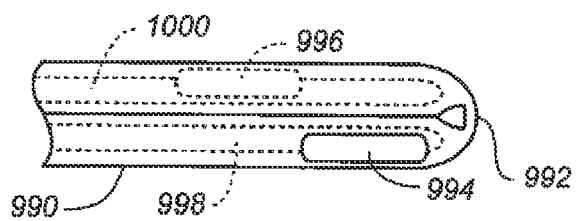

FIG. 94B is a semi-transparent view of the loop-tip catheter of FIG. 94A.

Figure 95:
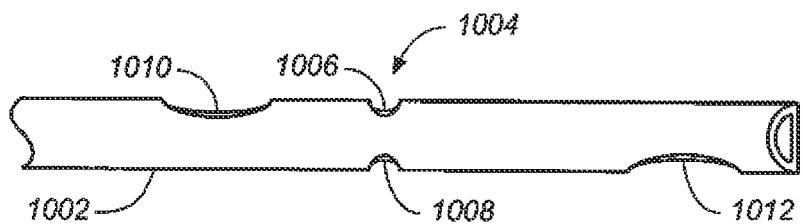

FIG. 95 illustrates an example of a tubing configuration for fabricating a catheter with an interfacing loop at the distal end of the catheter.

Figure 96:
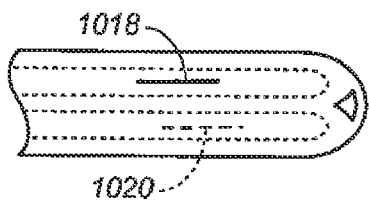

FIG. 96 illustrates one variation where a through-hole is provided at the tip of a loop-tip catheter to allow over-the-guidewire placement of the catheter.

Figure 97:
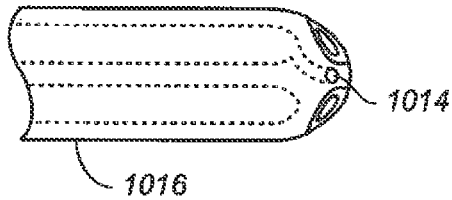

FIG. 97 illustrates another variation where slit-valves are implemented on the loop-tip catheter.

Figure 98:
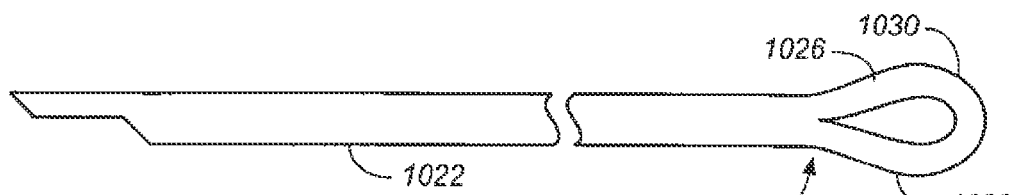

FIG. 98 illustrates another design, where the proximal end of a dual lumen catheter is configured with a loop.

Figure 99:
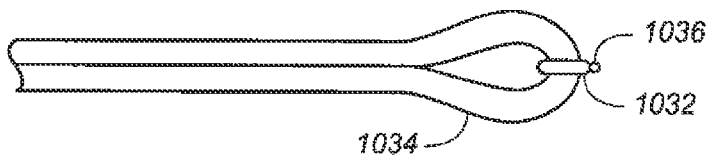

FIG. 99 illustrates a removable locking interface that can be coupled to the loop on the loop-tip catheter for connecting a tunneler to the loop-tip catheter.

Figure 100:
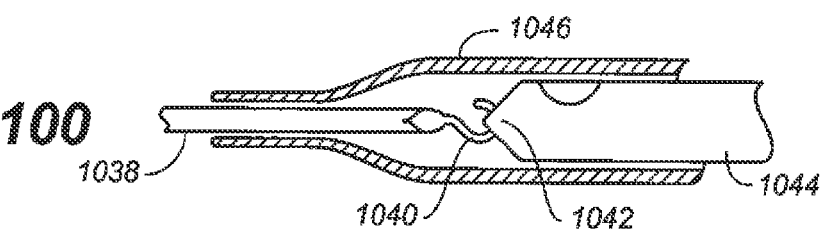

FIG. 100 illustrates a tunneler with a hook being utilized to engage a loop at the distal end of a catheter.

Figure 101:
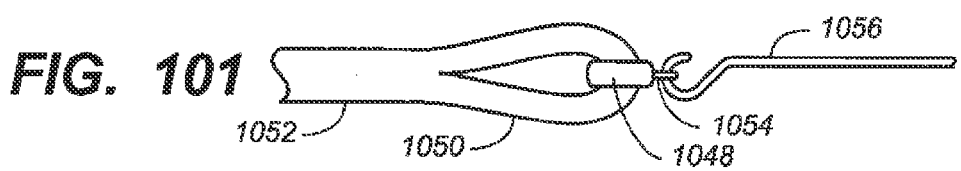

FIG. 101 illustrates another design where a mechanism adapted over the loop of the loop-tip catheter is utilized for connecting to a hook on a tunneler.

Figure 102:
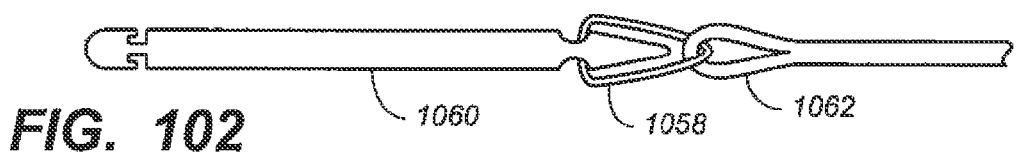

FIG. 102 illustrates yet another approach where strings are used to couple the loop of the catheter to a tunneler.

Figure 103:
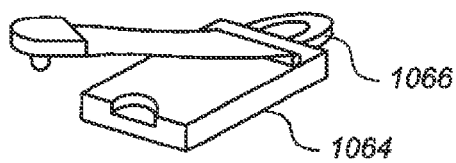

FIG. 103 illustrates one variation of an adaptor clip for connecting a medical instrument to the loop on a catheter.

Figure 104:
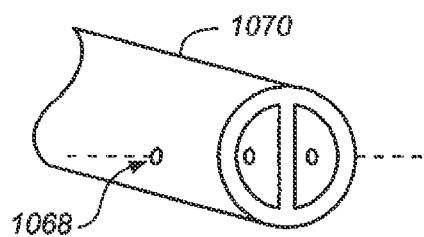

FIG. 104 illustrates another design where a through-hole is provided at the proximal end of the catheter, such that an instrument or a string may be passed through the through-hole to engage the proximal end of the catheter to a tunneler or other instrumentation.

FIG. 105 illustrates another approach for creating a loop-tip catheter. As shown in FIG. 105, a mid-portion along the length of a dual lumen catheter is partitioned to form the loop on the catheter.

FIG. 106 illustrates one variation of a dual lumen catheter configured from mid-shaft partitioning of a dual lumen catheter.

FIG. 107 illustrates another catheter design configured through partitioning/splitting the distal portion of a dual lumen catheter.

FIG. 108 illustrates another variation of a partitioned catheter tip design, where the distal ports of the two lumens are staggered along the length of the catheter.

FIG. 109 illustrates another variation of a partitioned catheter tip design. In this design, additional side ports are created for accessing the lumens of the catheter.

Figure 110A:
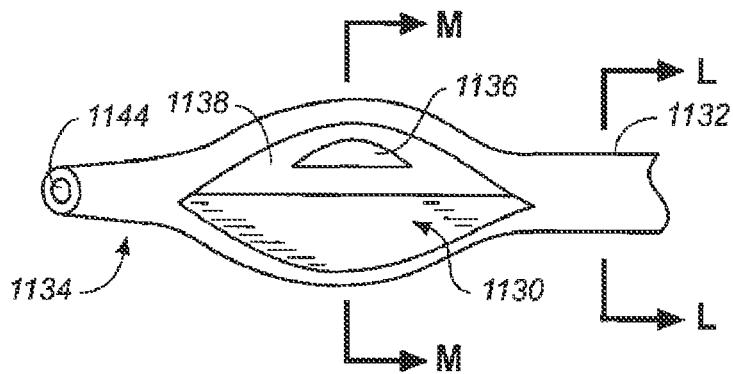

FIG. 110A illustrates another variation of a partition design where the partition is configured on the mid-shaft of the catheter. In this example, a port for accessing one of the catheter lumens is placed on one of the two surfaces created through the partition.

Figure 110B:
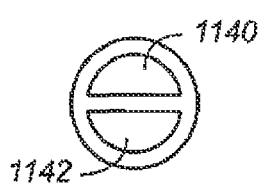

FIG. 110B is a cross-sectional view of the shaft of the catheter of FIG. 110A. The cross-section is taken at L-L on the proximal shaft of the catheter, as shown in FIG. 110A.

Figure 110C:
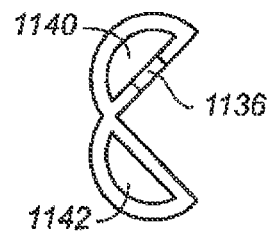

FIG. 110C is another cross-sectional view of the catheter of FIG. 110A. This cross-section is taken at M-M on the distal partitioned portion of the catheter, as shown in FIG. 110A.

Figure 111A:
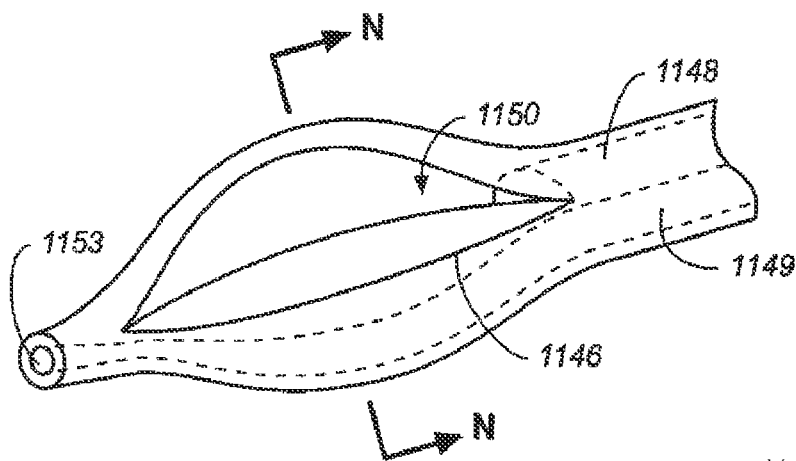

FIG. 111A illustrates another variation of catheter with a partitioned design. In this example, at the catheter is partition both above and below the septum, such that two flared openings are provided for accessing the lumens in the catheter. Each of the lumens exits right into the space in a partition which forms the corresponding flared opening.

Figure 111B:
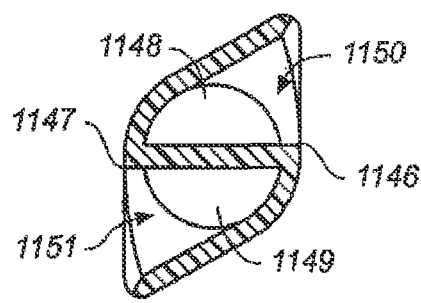

FIG. 111B is a cross sectional view of the catheter of FIG. 111A. The cross-section is taken at N-N, as shown in FIG. 111A.

FIG. 112A illustrates another partitioned catheter design. In this example, the longitudinal length of the slit forming the partition can be expanded to expose additional orifices for accessing the catheter lumen. FIG. 112A shows the slit in its initial (pre-expansion) condition.

FIG. 112B shows the catheter of FIG. 112A with the slit extended to expose an enlarged orifice for accessing one of the two lumens in the catheter.

FIG. 113 is a cross-sectional view of the catheter of FIG. 112A taken at the midsection of the partitioned opening.

FIG. 114 shows the catheter with a pre-configured slit that is initially sealed to cover a portion of the orifice which enters one of the two catheter lumens. The closed slit can be opened after implantation to provide additional access to the catheter lumen.

FIG. 115A-115E illustrate various lumen wall configurations for preventing lumen collapse. FIG. 115A shows one example where raised surface profiles are provided on the wall of the catheter to prevent the septum/divider between the two lumens from collapsing against the wall of the catheter.

FIG. 115B illustrates another example where raised surface profiles on the catheter wall are provided next to the septum.

FIG. 115C illustrates another variation where raised surface profiles are provided on both sides of the septum to support the septum. As shown in this figure, the septum may comprise a flexible material, such that during high flow rate infusion, the infused lumen may expand towards the adjacent lumen to allow a larger throughput of fluids.

FIG. 115D illustrates another variation, where the raised profiles are provided on the septum. As shown in FIG. 115D, the raised profile on the inner lumen wall may allow one to create a catheter with lumens of unequal size, while preventing the smaller lumen from collapsing onto itself.

FIG. 115E illustrates yet another variation where the septum is configured with a curved profile to prevent the septum from completely occluding a catheter lumen when it is has collapsed against the catheter wall.

DESCRIPTION OF THE INVENTION

The following detailed description should be read with reference to the drawings, in which identical reference numbers refer to like elements throughout the different figures.

The drawings, which are not necessarily to scale, depict selective embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

Before describing the present invention, it is to be understood that unless otherwise indicated this invention need not be limited to applications in humans. As one of ordinary skill in the art would appreciate, variations of the invention may be applied to other mammals as well. Moreover, it should be understood that variations of the present invention may be applied in combination with various catheters, connectors, adaptors, tubing introducers, and implantation instruments, for establishing a fluid conduit into a patient's body.

Hemodialysis is used herein as an example application of the loop-tip catheter to illustrate the various aspects of the invention disclosed herein. "Arterial lumen" and "venous lumen" are used herein as examples to describe a dual lumen catheter that may be utilized as a hemodialysis catheter. In light of the disclosure herein, one of ordinary skill in the art would appreciate that variations of the loop-tip catheter may be utilized in various medical procedures to establish fluid conduits into patients' body. One of ordinary skill in the art would appreciate that one may utilize both the arterial lumen and the venous lumen for simultaneous aspiration or infusion. It is also foreseeable that for certain applications, the arterial lumen may be utilized for infusion of fluid into the patient's body, while the venous lumen is being utilized for aspirating fluid from the patient's body.

It must also be noted that, as used in this specification and the appended claims, the singular forms "a," "an" and "the" include plural referents unless the context clearly dictates otherwise. Thus, for example, the term "a valve" is intended to mean a single valve or a combination of valves, "a fluid" is intended to mean one or more fluids, or a mixture thereof. Furthermore, the words "proximal" and "distal" refer to directions closer to and away from, respectively, a physician operating the device, with the tip end (i.e., distal end) placed inside the patient's body. Thus, for example, the catheter end placed within the body of the patient would be the distal end of the catheter, while the catheter end outside the patient's body would be the proximal end of the catheter.

In one aspect of the invention, the loop-tip catheter comprises an elongated catheter body with a loop coupled to the distal end of the elongated catheter body. The loop may be configured to prevent blockage of distal end catheter opening (s). The catheter may comprise a plurality of lumens. The lumen openings at the distal end of the catheter may be positioned on the loop structure. One or more of the lumens may be configured to extend into the loop structure.

For example, the loop-tip catheter may comprise a dual lumen catheter where the tip of the catheter incorporates a loop-like structure. The loop-like structure is designed to mechanically separate the lumen outlets/inlets at the tip of the catheter. The loop-like structure may protect the arterial inlet and prevent sidewall occlusion. The loop-tip catheter may further comprise a mechanism to allow the user to manipulate the loop-like structure. In one variation, an expansion and/or contraction mechanism may be implemented to allow the user to cover one or more of the lumen openings and/or allow user to clear obstructions at the distal portion of the catheter. For example, the loop-tip catheter may house a wire, a mandrel, or a balloon to improve patency and/or to minimize recirculation. The loop-tip catheter may also be configured such that the looped portion can be compressed for insertion into a narrow channel. For example, the looped tip may be compress and inserted into an introducer sheath and inserted into the patient's body. Once the catheter is put in place, the sheath is removed and the loop will expand and return to its original configuration. In one variation, the loop comprises a material with mechanical memory (e.g., elastic polymer, etc.) such that after the release of the compression force the loop can return to an expanded state. The elastic/pliable property of the loop structure may also prevent the side walls of the vessel from collapsing against each other when a negative pressure is generated within the lumen of the catheter.

The loop-tip catheter design may provide various benefits, including but not limited to: (1) occlusion resistance—the loop at the tip of the catheter can be utilized to protect the arterial inlet from sidewall occlusion (i.e., preventing the aspirating lumen opening from suctioning against the wall of the blood vessel); (2) improving the efficiency of the catheter's ability to circulate blood in and out of the body by minimizing recirculation—the loop structure can serve as a flow divider, thus minimizing recirculation; (3) improved manufacturability—for example, starting from a simple D-shaped or double-D shaped extrusion, a loop-tip catheter can be manufactured by modifying the extrusion, bending portions of it onto itself, and bonding portions together; (4) resistance to fibrin sheath formation—fibrin sheaths often occlude the arterial inlet of a traditional hemodialysis catheters, making them inoperable; the loop provides a diverting structure that may inhibit the propagation of a fibrin sheath around the distal tip of the catheter; (5) atraumatic looped tip may reduce fibrin formation due to reduced vessel side wall agitation—a traditional catheter with sharp surface profile may induce significant fibrin formation when it comes into contact with the vessel side wall; the rounded shape of the loop structure, on the other hand, may be less irritable to the tissue on the side wall of the vessel; (6) the loop may also be configured to serve as a stop to prevent a wire or a mandrel, introduced into the catheter from the proximal end, from going beyond the tip of the catheter; (7) the loop structure may also serve to maintain patency within the blood vessel, by keeping the vessel walls separated when a suction is applied within the lumen of the blood vessel—the loop may be configured to provide mechanical leverage to prevent the vessel wall from collapsing against each other; in addition, the loop may also be configured with a material stiff enough to protect the catheter outlets/inlets (i.e., preventing the side wall of the vessel from covering the lumen openings) when the catheter is inserted in a narrow vein (e.g., acting as a scaffolding, etc.).

In addition, the loop-tip catheter design may be configured to support one or more of the following capabilities: (1) protection of the arterial inlet when the catheter is not in use—the catheter may comprise a mechanism to cover the arterial inlet; for example, the loop structure may be compressed or twisted to cover one or more of the lumen openings on or near the loop structure; a balloon, mandrel, magnets, or wire may be utilized to seal the arterial inlet in between dialysis sessions; (2) ability to clear obstructions—the catheter may comprise a mechanism for compressing and/or expanding the loop structure to remove obstructions, such as fibrin sheaths, from an area surrounding the loop structure; for example, a mandrel or wire may be utilized to fold the loop structure in order to break up the fibrin sheath; (3) support sheath/introducer placement—the loop may be flattened either by pinching or by using a stiffening stylet so that the catheter can be introduced through a sheath while minimizing the risk of air embolism. Certainly, the loop-tip catheter of the present invention may be configured to support capabilities in addition to those specifically mentioned herein as well.

In one variation, the loop-tip catheter 2 comprises an elongated dual lumen tube 4, including a loop structure 6 at the distal end of the tube, as shown in FIG. 1. The proximal end of the catheter is connected to a bifurcation 8. Two extension tubings 10, 12 are connected to the bifurcation 8. Each of the two extension tubings is in fluid communication with one of the two lumens in the catheter. The two lumens in the elongated tube extend into the loop structure 6. In this example, the two lumens are separated within the loop, and thus, are prevented from communicating fluid directly from one to the other. In another design, the two lumens is allowed to communicate fluid through the loop structure.

One or more ports/openings can be positioned on the loop structure to provide access to one or both lumens. The ports may be positioned anywhere along the circumference of the loop. Access ports may also be provided along the shaft of the elongated catheter, if so desired. In the design shown in FIG. 2, a first port 14 is located close to the distal end on the outwardly facing side of the loop 6 for accessing a first lumen in the catheter, and a second port 16 is located on the inwardly facing side 18 of the loop for accessing a second lumen in the catheter. When the catheter is utilized as a hemodialysis catheter, the first lumen serves as the venous lumen for infusing processed blood into the patient's vascular system through the first port (i.e., venous outlet), while the second lumen serves as the arterial lumen for aspirating blood from the patient's body through the second port (i.e., arterial inlet).

As mentioned above, a common problem that frequently occurs during hemodialysis is arterial insufficiency caused by the arterial inlet suctioning against the wall of the blood vessel. FIG. 3A illustrates a typical dual lumen catheter with staggered lumen openings 20. The proximal opening 22, which serves as the arterial inlet, tends to suction against the wall of the blood vessel 24, resulting in partial or complete occlusion of the arterial inlet. FIG. 3B illustrates a typical split tip dual lumen catheter 26 with its arterial lumen 28 suctioning against the wall of the blood vessel 24. In both of these designs 20, 26 (i.e., staggered lumen and split tip), there is no mechanism to prevent the arterial inlet from suctioning against the wall of the blood vessel when the arterial inlet is positioned closed to the vessel wall. However, a catheter with a loop tip design 30 may minimize arterial insufficiency by preventing the arterial inlet 32 from suctioning against the wall of the blood vessel 24. In particular, when the arterial inlet 32 is positioned on the inner circumferential surface of the loop structure 34, it becomes very difficult for the wall of the vessel 24 to cover the arterial inlet 32, as shown in FIG. 3C.

There are various configurations for forming a loop at the distal end of the catheter. For example, a loop 36 can be placed at the distal tip 38 of the dual lumen catheter 40, as shown in FIG. 4A. In another variation, the tip of the dual lumen catheter has a bifurcation 42, and a loop 44 is coupled to the distal ends of the bifurcating branches 46, 48, as shown in FIG. 4B. Although in this example the two bifurcating branches are shown with equal lengths, one of ordinary skill in the art having the benefit of this disclosure would appreciate that the two extension branches may be of varying lengths. FIG. 4C shows another example where the two bifurcating branches 50, 52 connect to each other at the tip portion 54 to form the loop.

The loop may be formed by folding one tube onto itself and then bonding the shaft together. A catheter with either circular or non-circular (e.g., D-shaped, etc.) lumens may be utilized.

In addition, the loop-tip's natural/relaxed conformation may be modified during the formation process. For example, the tip can be made to kink 56 at its apex by shortening the loop 58 length, as illustrated in FIG. 5A. In another variation, the tip 60 is made to loop in an oval configuration by increasing its loop 62 length, as shown in FIG. 5B. The loop may be configured with a single channel providing fluid communication between the two lumens in the shaft of the catheter. In another variation, the two lumens extending into the loop are separated by a septum or divider somewhere along the length of the loop, such that the two lumens may function independently of each other.

One or more orifices for accessing the lumen/lumens of the catheter may be positioned along the circumference of the loop and/or along the shaft of the catheter. In one variation, the loop-tip catheter is configured for a hemodialysis type application where one lumen of the catheter is utilized for fluid infusion while the other lumen is utilized for fluid aspiration. The two lumens extending from the shaft of the catheter into the two ends of the loop are separated at the distal portion of the loop to allow the two lumens to function independently. FIG. 6A illustrates one example where the aspirating lumen (e.g., arterial lumen) is configured with an inlet 64 positioned close to the base 66 of the loop, while the infusion lumen (e.g., venous lumen) is configured with an outlet 68 positioned close to the tip portion 70 of the loop. The loop structure mechanically separates the outlets from the inlets, which may minimize recirculation. Furthermore, the curved shaped of the loop may keep the outlet and the inlet from being occluded by the sidewall of the vessel. Moreover, in another variation, additional side holes 72 are positioned on the inner side 74 of the loop to prevent arterial insufficiency.

The loop-tip catheter may be configured with two or more outlets/inlets to improve fluid flow rate. One of ordinary skill in the art having the benefit of this disclosure would appreciate that the outlets/inlets may be positioned anywhere along circumference of loop. In addition one or more orifices may be placed on the shaft in a region close to the distal loop. For example, an additional inlet may be placed at a location on the shaft close to the base of the loop.

FIG. 6B illustrates another variation where the inlet 76 is positioned on the inner circumferential surface of the loop. The configuration prevents the inlet from suctioning against the wall of the blood vessel. An optional inlet 78 is provided on the outer circumferential surface 80 of the loop as a secondary opening for aspirating fluids. In another variation, the inlet is configured with an extended opening 82 along the inner circumferential surface of the loop, as show in FIG. 6C. Additional side holes 84 may also be positioned on the loop.

FIGS. 6D-6G illustrate additional examples of different inlets/outlets placement designs. In FIG. 6D, the outer circumferential surface of the loop includes an extended opening 86 which serves as the outlet for the venous lumen, while the inner circumferential surface includes an elongated opening 88 which serves as the inlet for the arterial lumen. The outlet 86 is distally positioned in relation to the inlet 88 to minimize recirculation. FIG. 6E shows an example where the loop section distal to the outlet 90 and the inlet 92 are removed, leaving only a loop layer 94 to keep the two branches 96, 98 separated. In this design, the two lumen openings 90, 92 exit in the distal direction, instead of facing the side wall of the vessel. An optional orifice 100 can be provided to allow fluid intake from the region within the center of the loop. FIG. 6F shows another design where the distal portion of the venous branch 102 is substantially open such that the venous outflow may exit the outlet 104 and flow directly in the distal direction. On the arterial branch, an inlet 106 is provided on the inner circumferential surface of the loop to prevent suctioning against the wall of the vessel. FIG. 6G is an example in which the venous outlet 108 is positioned at the distal tip of the loop, while the arterial inlet 110 is positioned on the inner circumferential surface of the loop and is close to the branching point 112, such that the distance between the venous outlet 108 and the arterial inlet 110 is maximized.

Figure 7A:
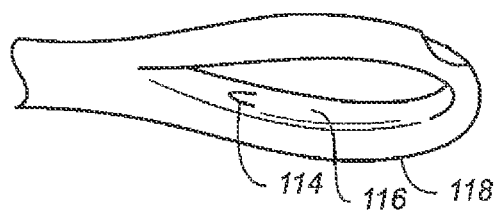
FIGS. 7A-7B illustrate implementation of various slit valve designs on the loop-tip catheter.
Figure 7B:
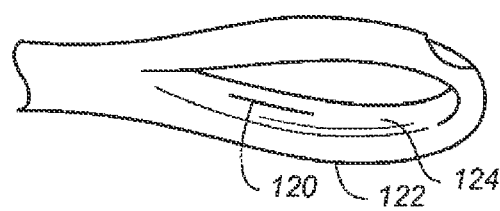

In another variation, valves are implemented at the inlet and/or the outlet. For example, slit valves may be implemented such that the distal lumen openings are closed when they are not being utilized for fluid infusion or aspiration. Since tissue build-up at the arterial inlet may compromise the catheter's ability to aspirate, a valve can be placed over the arterial inlet to cover the inlet when the arterial inlet is not being used. For example, a slit valve can be implemented on the arterial inlet to prevent clot growth. FIG. 7A illustrates one variation where a U-shaped slit valve 114 is placed on the inner circumferential surface 116 of the loop 118 for accessing the arterial lumen. In FIG. 7B, a straight slit 120 is positioned on the loop 122. In one variation, the loop is configured with a flat surface 124 on the inner loop surface, which may improve the performance of the slit valve. In certain embodiments, the loop portion or the entire catheter is comprised of silicone to further improve the performance of the slit valve. In another variation, both the arterial inlet and the venous outlet are configured with slit valves.

One of ordinary skill in the art having the benefit of this disclosure would appreciate that there are various approaches for manufacturing the loop-tip catheter of the present invention, some of which are disclosed herein. An example utilizing a single tubing to form a catheter with a loop tip is described below. A catheter with one or more lumens is folded onto itself, wherein the proximal portion of the catheter is bonded to form the loop-tip catheter. Orifices is created on the catheter through etching, cutting or otherwise removing portion of the catheter wall to form the access ports at the distal portion of the loop-tip catheter. The orifices can be created either before or after the catheter is folded. If a dual lumen catheter with lumens which can function independently is desired, the midsection of the catheter may be sealed by heat bonding or through the placement of a septum.

Figure 8A:
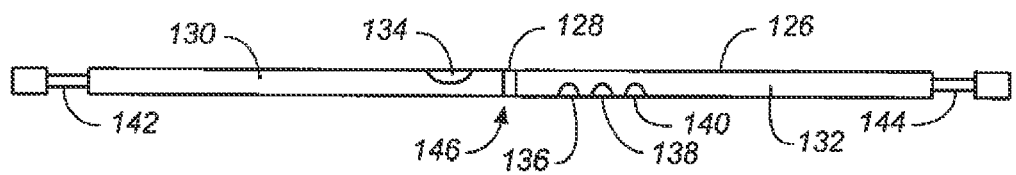
FIGS. 8A-8C illustrate an exemplary approach to fabricate a loop-tip catheter. In this example, orifices are formed on a single lumen catheter to serve as inlets and outlets. The catheter is then folded to form a dual lumen loop-tip catheter.
Figure 8B:
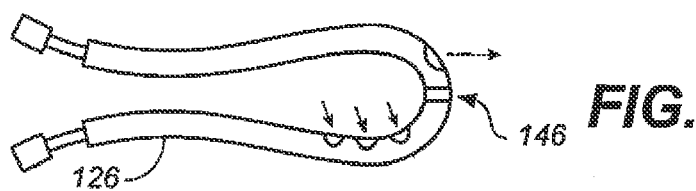
Figure 8C:
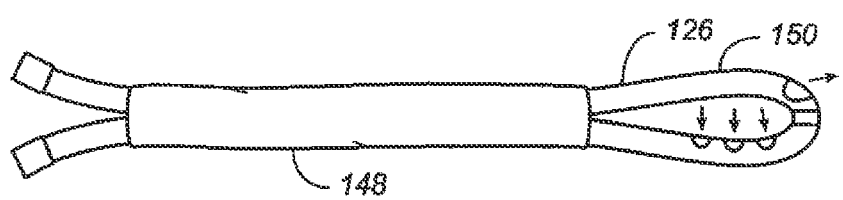

In one variation, as shown in FIG. 8A, a polyurethane catheter 126 is utilized to form the loop-tip catheter. A seal 128 is created on the midpoint of the catheter to form two separate lumens 130, 132 extending towards the two ends of the catheter. Selective openings 136, 138, 140 are created at the mid-region of the catheter 126 by cutting of portion of the catheter wall. Luer fittings 142, 144 are placed at the two ends of the catheter to serve as the coupling interfaces. The catheter 126 is then folded onto itself at the midpoint 146, as shown in FIG. 8B. An oversleeve 148 is then placed over the proximal portion of the catheter 126 and bonded onto the catheter to form a loop-tip catheter, as shown in FIG. 8C. In another variation, a silicone tubing is utilized to form the loop while a polyurethane tubing is placed over the silicone catheter to form the loop-tip catheter.

Figure 9A:
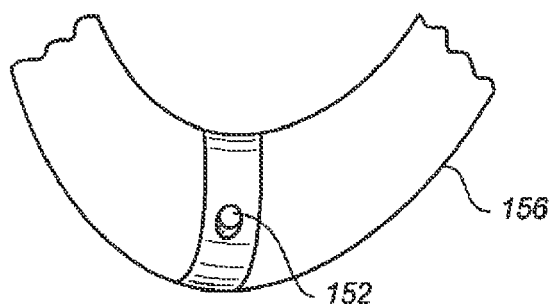
FIG. 9A illustrates one example of implementing a through-hole to accommodate a guidewire.
Figure 9B:
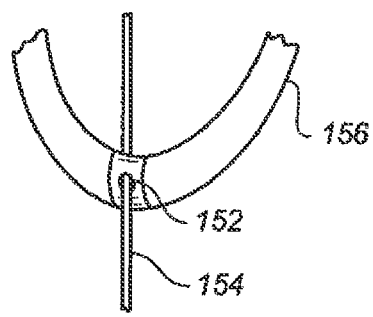
FIG. 9B shows a guidewire passing through the through-hole on the loop-tip catheter of FIG. 9A.
Figure 10:
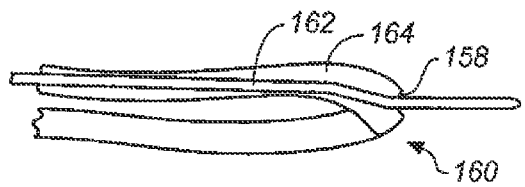
FIG. 10 illustrates another approach, where a guidewire is passed through the lumen within the loop-tip of the catheter and exits at the distal venous lumen opening.

The loop-tip catheter can also be configured to support over-the-guidewire placement of the catheter. In one design, a through hole 152 is positioned at the distal tip of the catheter 156, as shown in FIG. 9A. The catheter can then be placed over-the-guidewire by inserting the proximal end of the guidewire 154 into the through hole 152 and advancing the guidewire along the length of the catheter, as shown in FIG. 9B. If an arterial inlet is placed on the inner circumferential surface of the loop, the user can simply insert the guidewire into the arterial lumen through the inlet. In another design, a separate lumen is provided along the length of the catheter to support the guidewire. However, if the venous lumen 158 is placed close to the distal tip 160 of the loop, the user may simply pass the guidewire 162 through the venous lumen 164, as shown in FIG. 10.

Figure 11A:
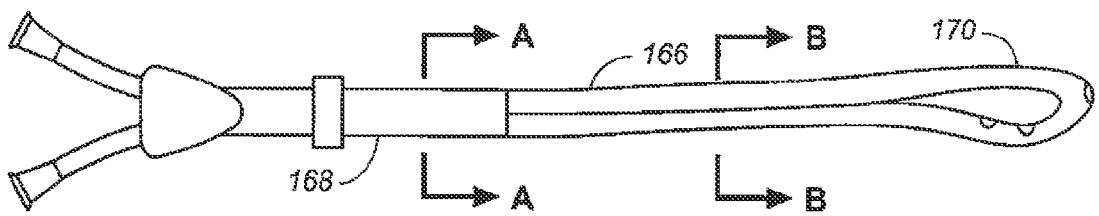
FIG. 11A illustrates another variation of a dual lumen loop-tip catheter.
Figure 11B:
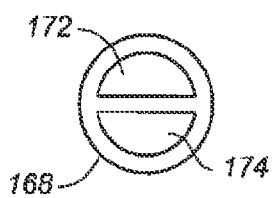
FIG. 11B shows a cross-sectional view of a proximal section of the catheter of FIG. 11A. The cross-section is taken at A-A, as shown in FIG. 11A.
Figure 11C:
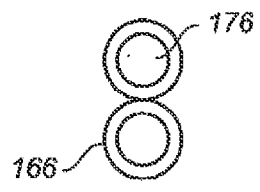
FIG. 11C shows a cross-sectional view of a distal section of the catheter of FIG. 11A. The cross-section is taken at B-B, as shown in FIG. 11A.

In another design, the loop-tip catheter comprises a folded tubing 166 connected to a dual lumen catheter 168. As shown in FIG. 11A, the folded tubing 166 forms the loop section 170 of the catheter. Depending on the design criteria, the folded tubing 166 and the dual lumen catheter 168 may comprise the same type of material or different types of materials. The folded tubing and the dual lumen catheter may be configured with matching structural characteristics. In one variation, both the dual lumen catheter and the folded tubing includes D-shaped lumens. In another variation, the dual lumen catheter and the folded tubing comprise different structural characteristics. For example, the dual lumen catheter may include two D-shaped lumens 172, 174 (FIG. 11B), while the folded tubing has a circular shaped lumen 176 (FIG. 11C).

Figure 12A:
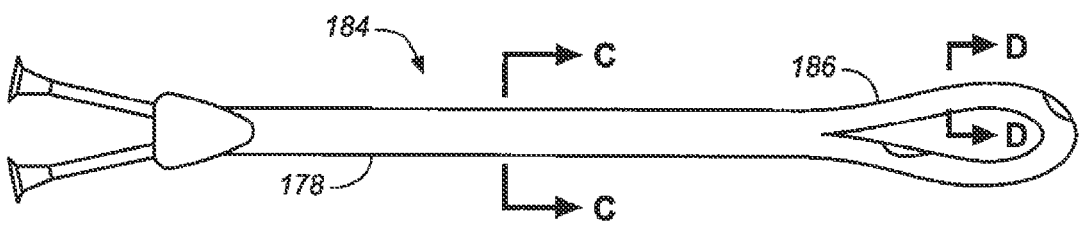
FIG. 12A illustrates another variation of a loop-tip catheter comprises a D-shaped tube folded over itself to form a dual lumen catheter with a loop-tip.
Figure 12B:
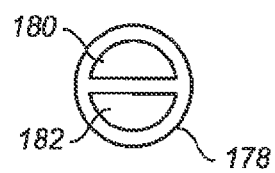
FIG. 12B is a cross-sectional view of the shaft of the loop-tip catheter of FIG. 12A. The cross-section is taken at C-C, as shown in FIG. 12A.
Figure 12C:
FIG. 12C is a cross-sectional view of the looped segment of the catheter of FIG. 12A. The cross-section is taken at D-D, as shown in FIG. 12A.

In yet another design, the loop-tip catheter is formed from a single dual lumen catheter. First, the distal end of the catheter is partitioned to form two branches. Then, the distal ends of the two branches are connected to form the loop. In FIG. 12A, a dual lumen catheter 178 with D-shaped lumens is utilized to form the loop-tip catheter. The proximal portion 184 of the loop-tip catheter includes two D-shaped lumens 180, 182 positioned side by side (FIG. 12B), while the distal loop 186 section has a single D-shaped lumen 188 (FIG. 12C).

Figure 13A:
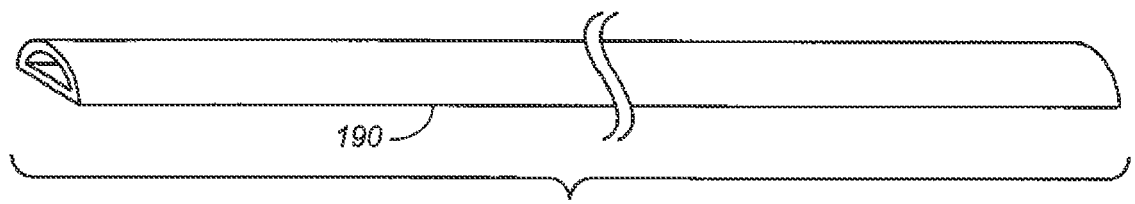
FIGS. 13A-13E illustrate one approach to form a loop-tip catheter from a D-shaped tubing.
Figure 13B:
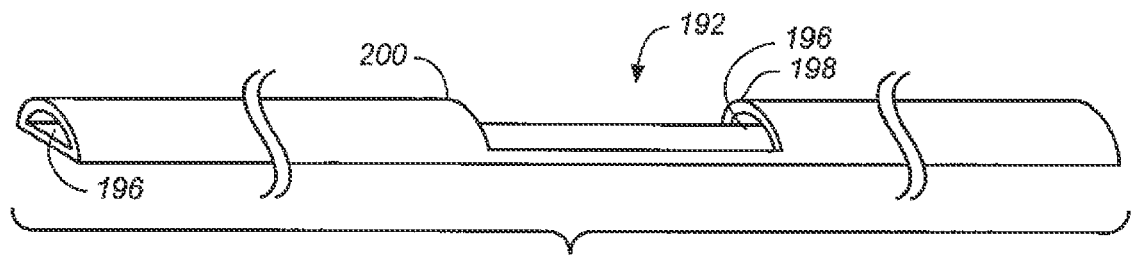
Figure 13C:
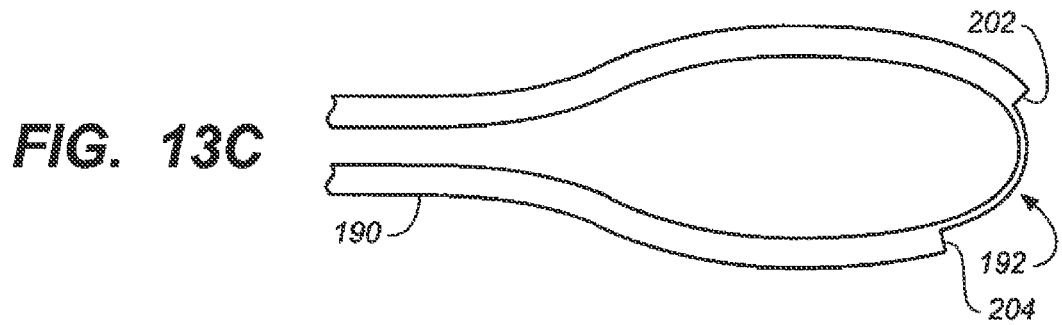
Figure 13D:
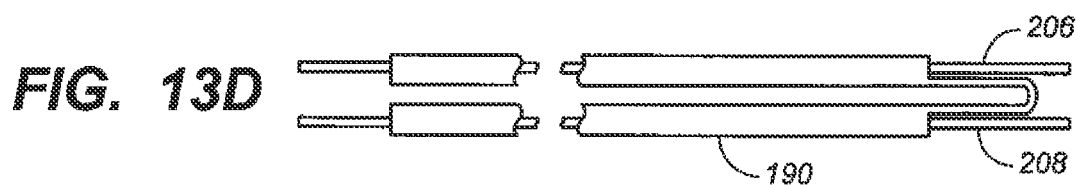
Figure 13E:
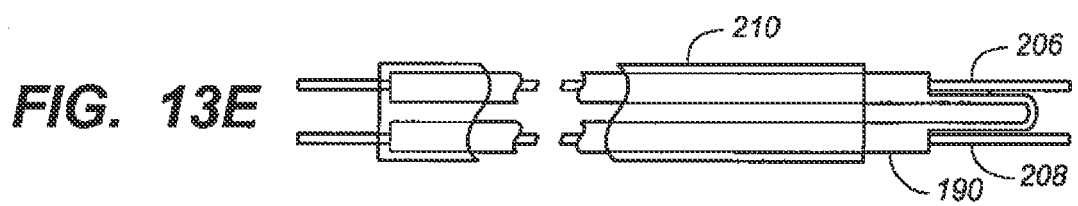

FIGS. 13A-13E illustrates another approach to fabricate a loop-tip catheter. To improve shape and symmetry of the loop-tip, the apex thereof may be positioned at the center of a cut-away section. Starting with a single D-shaped lumen catheter 190 (FIG. 13A), a midsection 192 of the catheter is removed to provide access to the lumens 194, 196 at the two ends of the catheter (FIG. 13B). To facilitate insertion, the edges 198, 200 of the cut-away may be tapered rather than straight cut. The catheter 190 is then folded over its midsection 192 (FIG. 13C). The position of the two midsection openings 202, 204 can be adjusted relative to each other depending on the user's desire in the placement of the arterial inlet and the venous outlet. Next, mandrels 206, 208 are placed into the lumens of the catheter 190 (FIG. 13D). A heat shrink tubing 210 is then placed over the proximal portion of the folded catheter 190 to bind the two segments of the catheter tubing together and form a loop-tip catheter with double-D configuration along the shaft of the loop-tip catheter (FIG. 13E).

Figure 14A:
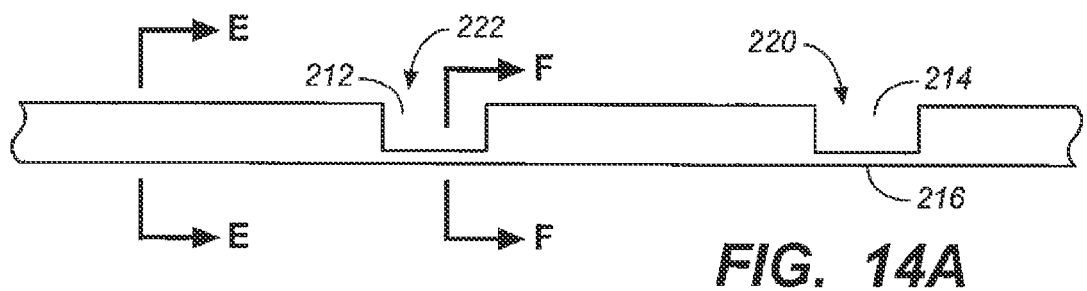
FIG. 14A illustrates a D-shaped catheter configured for forming another variation of a loop-tip catheter.
Figure 14B:
FIG. 14B is a cross-sectional view of the catheter of FIG. 14A. The cross-section is taken at E-E, as shown in FIG. 14A.
Figure 14C:
FIG. 14C is a cross-sectional view of a cut-down portion of the catheter. The cross-section is taken at F-F, as shown in FIG. 14A.
Figure 15:
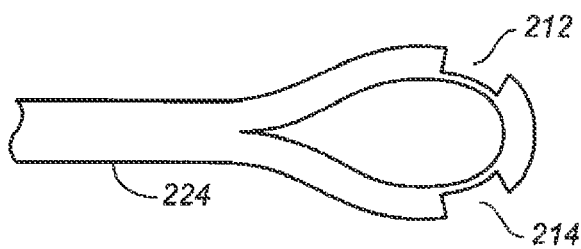
FIG. 15 illustrated a loop-tip catheter configured from the D-shaped catheter of FIG. 14A.

In another example, two or more orifices are created on an elongated tubing to form the plurality of inlets/outlets on a loop-tip catheter. The elongated tubing is then folded and bonded to form the loop-tip catheter. For example, one may cut two openings 212, 214 on an elongated D-shaped tubing to form the tubing 216 shown in FIG. 14A. Sections of the catheter retain the D-shaped lumen 218, a shown in FIG. 14B, while the cut-sections 220, 222 have the side walls removed, as shown in FIG. 14C. The tubing 216 is folded, and then bonded to form the catheter 224 shown in FIG. 15.

Figure 16:
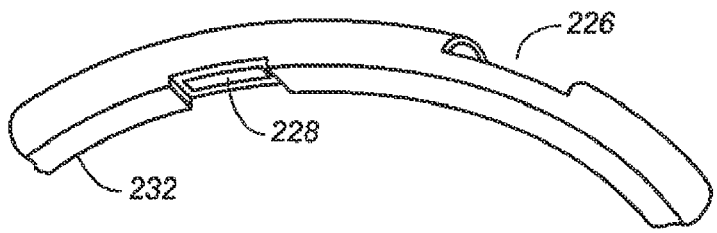
FIG. 16 illustrates a tube which has been modified for configuration into a loop-tip catheter with an outwardly facing opening for a first lumen, and an inwardly facing opening for a second lumen.
Figure 17:
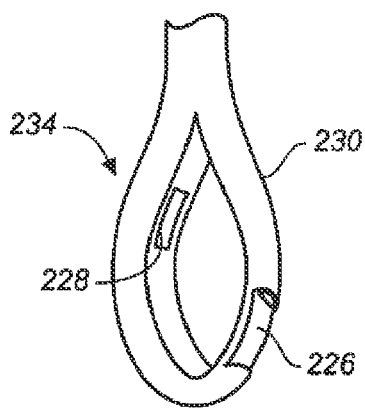
FIG. 17 illustrates a loop-tip catheter configured from the tube of FIG. 16.
Figure 18:
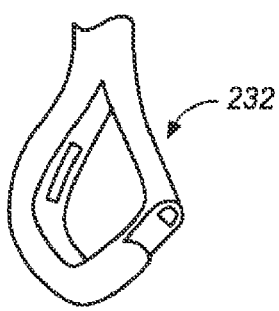
FIG. 18 illustrates another variation where the loop-tip catheter is fabricated from a tubing with inhomogeneous material distribution, such that the loop forms a predefined shape.

In FIG. 16, the two cuts that create the orifices 226, 228 on the loop are placed on the opposite sides of the tubing 232. An opening is created on the flat side of the D-shaped catheter to form the arterial inlet 228 on the inner circumferential circle of the loop 230. Once the tubing 232 is folded and bonded, a catheter 234 shown in FIG. 17 is formed. In one variation, the tubing forming the loop-tip catheter comprises inhomogeneous material along its length, such that when the catheter is folded, the resulting loop 232 has a distorted (i.e., non-circular) shape, as shown in FIG. 18. One of ordinary skill in the art having the benefit of this disclosure would appreciate that by varying the material characteristic of the tubing along its length one can fabricate loops of specific shapes and sizes to meet particular design specifications.

Figure 19A:
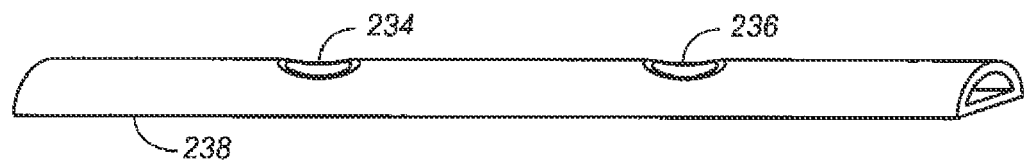
FIGS. 19A-19C illustrate one method for preparing a tubing for the fabrication of a loop-tip catheter.
Figure 19B:
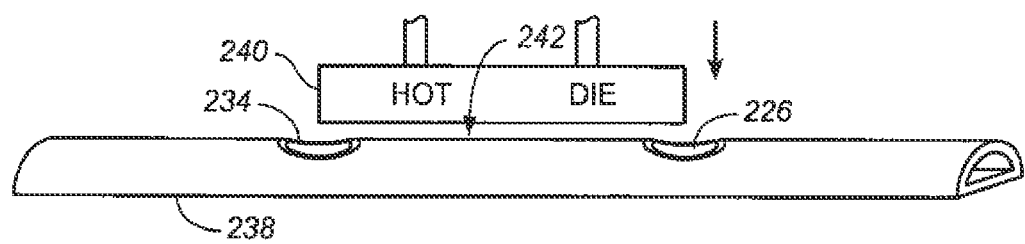
Figure 19C:
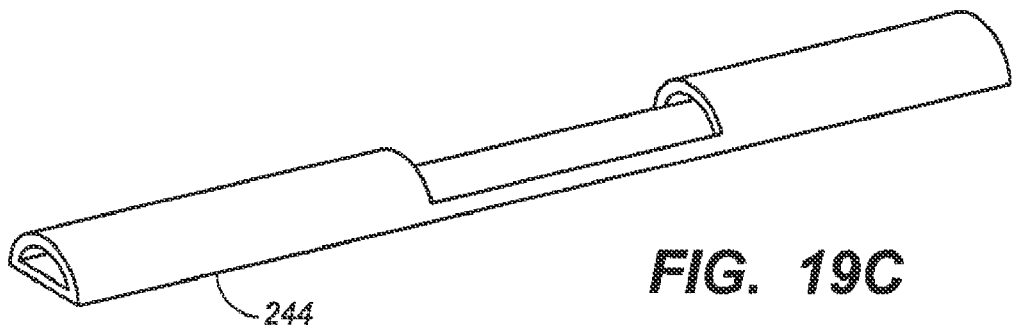
Figure 20:
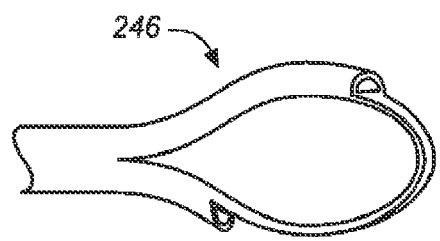
FIG. 20 illustrates one possible configuration of a loop-tip catheter fabricated from a tubing shown in FIG. 19C.

FIGS. 19A-19C show another approach to prepare a tubing for the formation of loop-tip catheter. Two holes 234, 236 are drilled or cut into a D-shaped tubing 238 as shown in FIG. 19A. A crimping hot die 240 is then used to deform the center portion 242 of the tubing between the two holes 234, 236, as shown in FIG. 19B. This approach may allow one to ensure that the loop tip configuration remains symmetrical by producing the loop section in an controlled and systematic manner. The resulting catheter 244 is shown in FIG. 19C. The die-processed catheter is then folded and bonded to form a loop-tip catheter 246, as shown in FIG. 20. This compression technique may allow one to conserve material and form a loop structure with a stronger mechanical property and/or a more ridged structural property.

Figure 21:
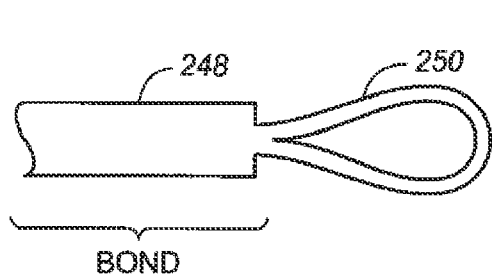
FIG. 21 illustrates one variation of a loop configuration where the lumen portion of the catheter is completely bonded.
Figure 22:
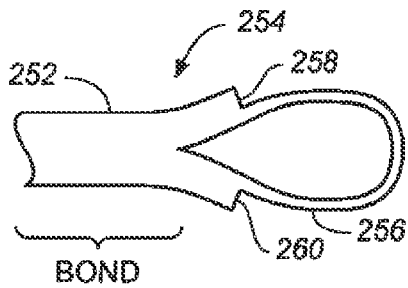
FIG. 22 illustrates a variation which is related to the loop configuration shown in FIG. 21; however, a distal section of the lumen portion of the catheter is not bonded, allowing the distal lumens to diverge from one another.

By varying the bonding lengths of the tubing, one may create loops of different characteristics. For example, by bonding the complete uncut portion of the tubing, a dual lumen catheter 248 with a loop 250 at the distal end is formed, as shown in FIG. 21. In another variation, by leaving a portion of the uncut tubing separated from each other, a dual lumen catheter 252 with a distal bifurcation 254 is formed, as shown in FIG. 22. The loop 256 at the distal end of the catheter keeps the two distal ports/openings 258, 260 separated from each other. One may also vary the relative position (along the axial length of the catheter) between the two distal openings such that one lumen has an opening that is distally positioned relative to the other one.

Figure 23A:
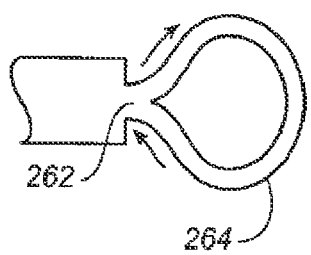
FIGS. 23A-23C illustrate various loop configurations which are designed with different shapes.
Figure 23B:
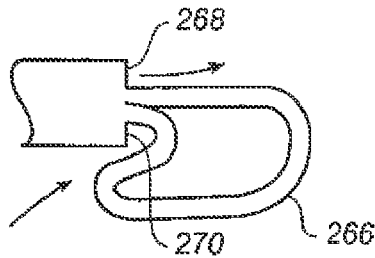
Figure 23C:
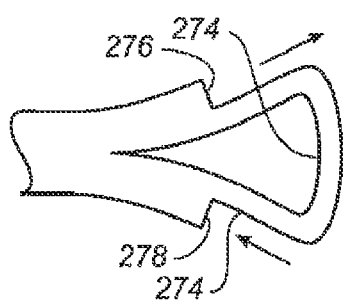

FIGS. 23A-23C illustrate additional examples of a loop-tip catheter of the present invention. In one example, a shaft 262 extends from the tip of a dual lumen catheter before it bifurcates and forms a loop 264 (FIG. 23A). In another example, the loop 266 is molded such that it is offset to one side of the catheter longitudinal axis. This configuration may prevent the loop 266 from blocking the outlet 268 of the venous lumen to facilitate fluid outflow in the distal direction (FIG. 23B). Furthermore, the loop 266 may be configured to direct fluid flowing from the proximal direction to enter the inlet 270 of the arterial lumen. In yet another example, the distal portion of the loop 272 is strengthened to form a bridge 274 that separates the openings 276, 278 of the two lumens (FIG. 23C).

Figure 24:
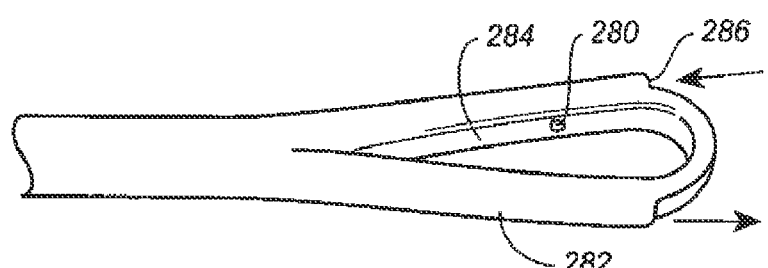
FIG. 24 illustrates another variation of loop-tip catheter. In this variation, the two lumens are symmetrically positioned in relation to the axis of the catheter and both lumens have exit opening at the distal end of the catheter. The catheter can be configured with one or more inwardly facing ports.

FIG. 24 shows another example of a loop tip design. Additional side holes 280 can be positioned on the loop 282 to provide additional openings for accessing one or both of the lumens. In this example, a side hole 280 is provided on the inner side 284 of the loop structure 282 to serve as an extra arterial inlet. Optionally, the distal arterial inlet 286 may be occluded using a heat process or a plug. An arterial inlet can be positioned along the circumferential surface along the length of the arterial branch to provide access to the arterial lumen. For example, the arterial inlet can be positioned on the inner portion of the loop-tip configuration in order to minimize recirculation and prevent suctioning against the vessel side wall, as discussed above. Furthermore, to improve kink resistance and maintain the shape of the loop, material reinforcements may be implemented within the looped section of the catheter. For example, a coil is integrated within the loop section to provide structural reinforcement while maintaining enough flexibility therein. As discussed above, various methods that are well known to one of ordinary skill in the art may be utilized to reinforce the loop structure to form different shapes.

Figure 25:
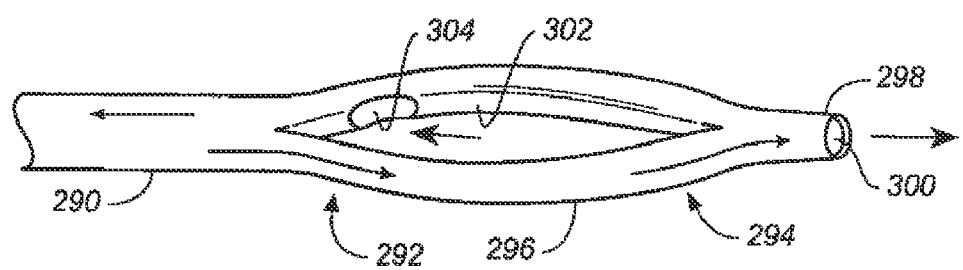
FIG. 25 illustrates another variation of a loop-tip catheter comprising a dual lumen catheter with a separated shaft section, which converges at the distal end of the catheter to form a loop.
Figure 26A:
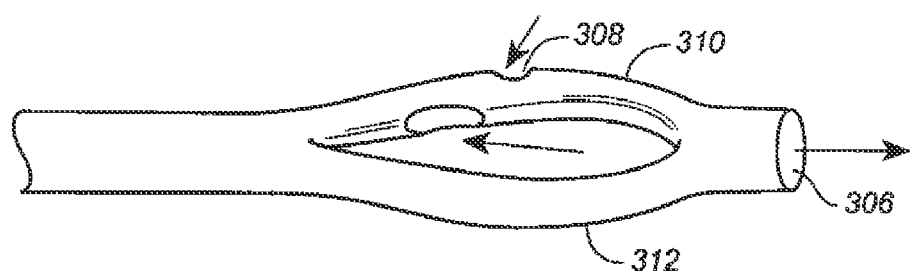
FIGS. 26A-26B show different variations of loop-tip catheters with a loop section that supported lumens that extend from the shaft of the catheter. A single opening is provided at the tip of the catheter for fluid communication with one of the two lumens.
Figure 26B:
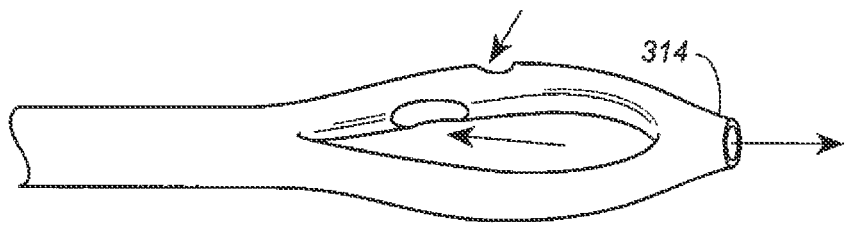
Figure 27:
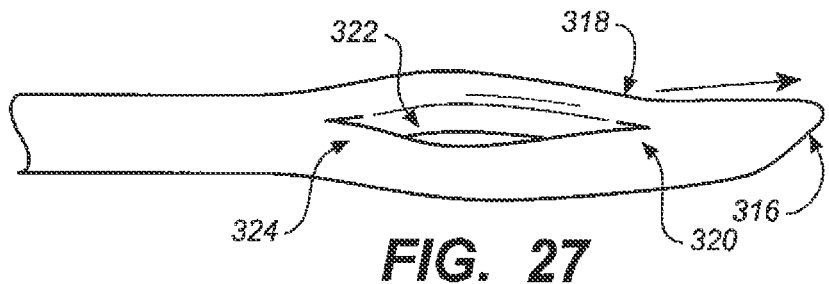
FIG. 27 illustrates another variation of a loop-tip catheter including a separated shaft section, which forms the loop. In this variation, the distal tip of the catheter is closed.

In another aspect of the invention, a section of the catheter shaft is separated to form a loop structure along the length of the catheter. The loop-tip catheter may comprise a dual lumen catheter 290 that bifurcates 292 for a section, and then merges 294 again to form the distal loop 296, as shown in FIG. 25. In the example shown in FIG. 25, a first lumen is configured to exit at the distal end 298 of the catheter, which may serve as the venous lumen 300, while the second lumen is configured with an opening positioned at the inner surface 302 of the loop 296, which may serve as the arterial lumen 304. FIG. 26A shows a variation, in which the distal venous lumen opening 306 is enlarged while the arterial lumen is configured with an additional inlet 308 positioned on the outer surface 310 of the loop 312. In FIG. 26B, a variation with a shortened distal end nozzle 314 is illustrated. One of ordinary skill in the art having the benefit of this disclosure would appreciate that the outlets/inlets may be positioned anywhere along circumference of loop. In another variation the loop-tip catheter is configured with a rounded atraumatic tip 316. The tip of the catheter may be closed and the ports for accessing the lumens are provided along the loop of the catheter. In one example, shown in FIG. 27, the outlet 318 to form the venous lumen is positioned on the outer surface of the loop close to the merging point 320 of the bifurcation, while the inlet 322 to the arterial lumen is positioned on the inner surface of the loop close to the bifurcating point 324 of the loop.

Figure 28A:
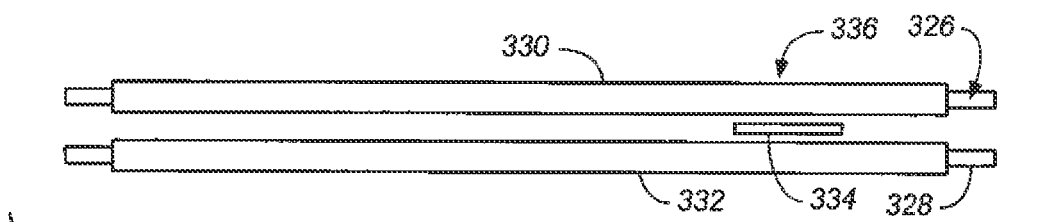
FIGS. 28A-28B illustrate an exemplary method for fabricating a loop-tip catheter with a separated shaft section by placing a divider to keep a portion of the tubes separated when the two tubes are bonded to form a dual lumen loop-tip catheter.
Figure 28B:
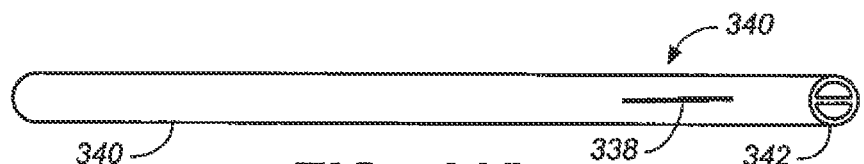

FIGS. 28A-28B illustrate one approach to fabricating a catheter with split shaft section for forming a loop. Two catheters are bonded together at all locations along the length thereof, but an intermediate segment proximal to the tip. In an exemplary process, mandrels 326, 328 are inserted into two tubings 330, 332 and then aligned with each other. A divider/shim 334 is positioned between the two tubings at a location proximal to the tip to prevent the designated section 336 from binding to each other (FIG. 28A). The two tubings 330, 332 are then bonded together (e.g., heating, adhesive, heat shrink, etc.). For example, a piece of shrink tubing is placed over the entire assembly. Heat is then applied to bond together all but the shimmed-off portion. After the catheters have bonded, the mandrels can be removed. In one variation, two D-shaped catheters are bonded with the flat sides facing each other such that a unified catheter with a circular cross-section can be formed.

Figure 29A:
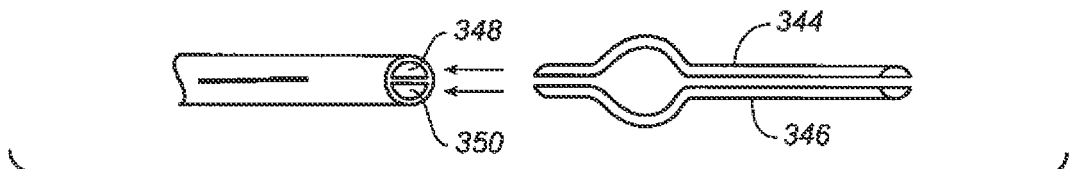
FIGS. 29A-29B illustrate the placement of pre-shaped mandrels in the catheter of FIG. 28B to form the loop on the catheter.
Figure 29B:
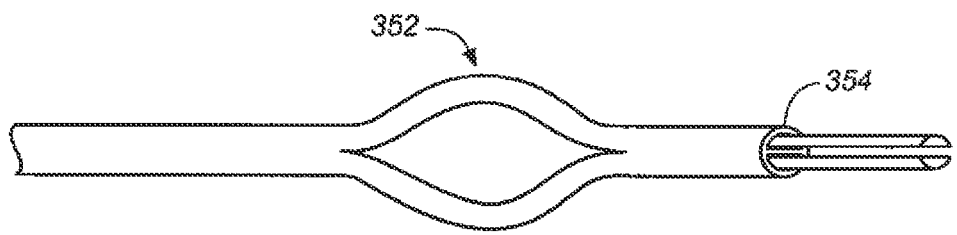

In another approach, a slit 338 is cut into the mid-shaft of a dual lumen catheter 340 along the length of the catheter to create a partitioned segment that is proximal to the tip 342 of the catheter (FIG. 28B). This segment may then be utilized to form the loop on the shaft of the catheter. Once a dual lumen catheter with a partially partitioned shaft is formed, two mandrels 344, 346 with predefined shapes are placed into the catheter lumens 348, 350 to form the loop shape on the shimmed/separated section (FIG. 29A). With the shaped mandrels positioned in place, heat is applied at the looped segment causing the material at the shimmed/separated section 352 to conform to the shape of the mandrel (FIG. 29B). Once the tubings have cooled down, the mandrels can be removed. The catheter may be further modified such that the arterial inlet(s) are positioned on the bowed section and the venous outlet(s) are positioned on the tip. An RF tipping process may be employed to enlarge the venous outlet by deforming the lumen into the arterial space—thus eliminating the arterial lumen at the tip 354.

Figure 30A:
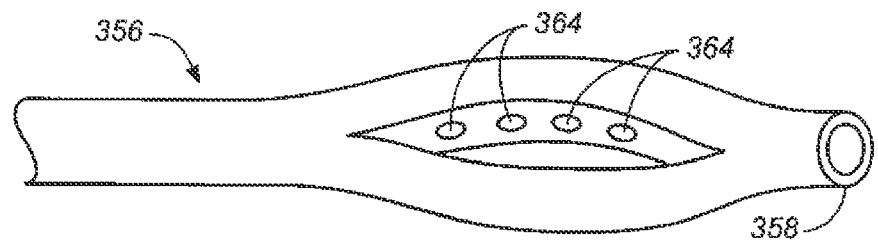
FIG. 30A illustrates another variation of a loop-tip catheter. In this variation, the venous outlet is located at the distal end of the catheter, while the arterial inlets comprise a plurality of inwardly positioned openings located on the inner surface of the loop.
Figure 30B:
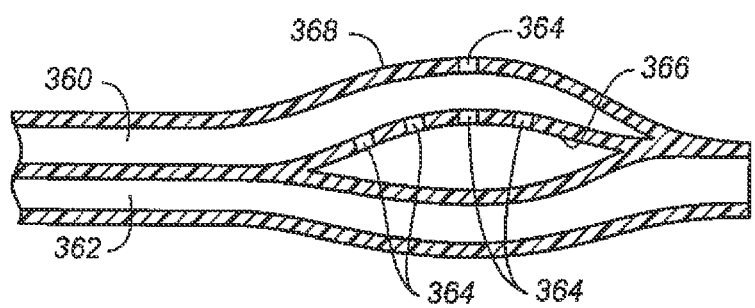
FIG. 30B is a cross-sectional view of the loop-tip catheter of FIG. 30A.

FIG. 30A shows one example of a loop-tip catheter 356 configured with a split shaft. A first lumen 360 is configured to pass-through from the proximal end to the distal end 358 of the catheter. A second lumen 362 is configured to terminate before it reaches the distal end of the catheter, while side ports 364 are created along the length of the loop for accessing the second lumen. As shown in FIG. 30B, two or more side ports 364 are positioned along the loop. The side ports are created on the inner side 366 and/or the outer side 368 of the loop. In this particular example, four side holes are positioned on the inner surface of the loop and one side hole is positioned on the outer surface of the loop. To insert a catheter into an orifice, a stiffening stylet may be placed in the arterial lumen terminating at the distal end of the venous lumen to straighten out the loop section. The venous lumen may be employed for over-the-wire procedures. The loop may be compressed together when placed inside a sheath for placement into a patient's body.

Figure 31A:
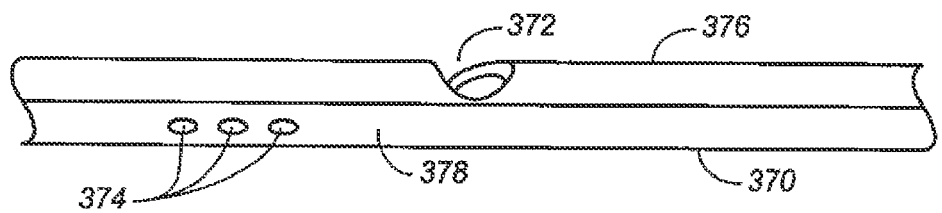
FIGS. 31A-31D illustrate one method for fabricating a dual lumen loop-tip catheter with a distal end venous outlet.
Figure 31B:
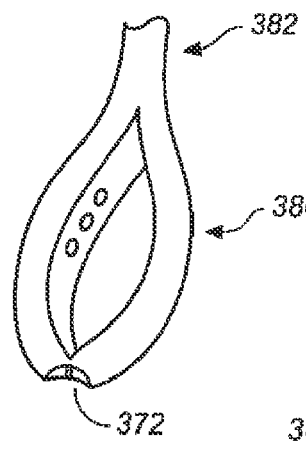

FIGS. 31A-31D illustrates yet another approach to prepare a loop-tip catheter with a distal end opening. Orifices are created on a D-shaped catheter 370, as shown in FIG. 31A. A large hole 372 is formed on the rounded side 376 of the D-shaped catheter to form a venous outlet. A plurality of holes 374 are placed on the flat side 378 of the D-shaped catheter to serve as the arterial inlets. The D-shaped catheter is folded at the large arterial opening. With the flat sides of the catheter coming in contact with each other, the proximal portion 382 of two folded catheter legs are bonded to each other, forming the structure 380 shown in FIG. 31B.

Figure 31C:
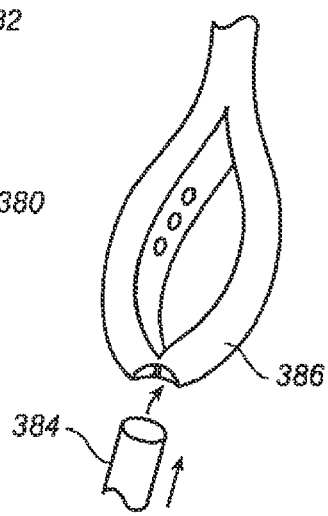
Figure 31D:
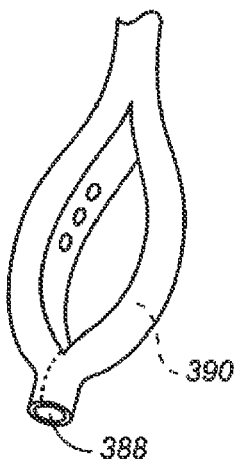

An RF tipping process may then be utilized to modify the shape of the venous outlet at the tip of the catheter. A rounded mandrel 384 is inserted into the venous side 386 of the lumen distal end outlet, as shown in FIG. 31C. The wall of the catheter at the center of the distal opening is sandwiched against the arterial side of the opening, sealing off access to the arterial lumen. As the result, the distal opening 388 becomes a single opening for accessing the venous lumen 390, as shown in FIG. 31D. The RF tipping process may relax the tubing such that the looped section reduces its propensity to bow outward. In this example, a round pin or other reinforcing material is introduced to strengthen the shape of the loop. A heating process may also be utilized to reset the loop back to a desired shape.

Figure 32:
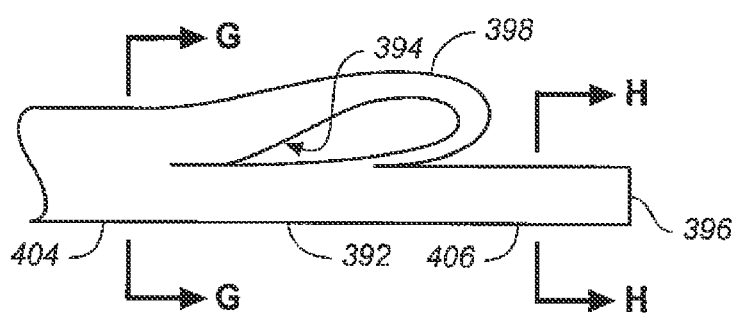
FIG. 32 illustrates another variation of a loop-tip catheter, which comprises an off-centered loop that is positioned over a distally extending fluid channel.
Figure 33A:
FIG. 33A is a cross-sectional view of a distal portion of the loop-tip catheter of FIG. 32. The cross-section is taken at H-H, as shown in FIG. 32.
Figure 33B:
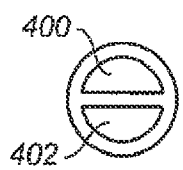
FIG. 33B is a cross-sectional view of a proximal shaft portion of the loop-tip catheter of FIG. 32. The cross-section is taken at G-G, as shown in FIG. 32.

In another aspect of the invention, the loop-tip catheter comprises an off-axis loop. One example is illustrated in FIG. 32. The catheter 392 comprises a dual lumen tubing with two distal ports 394, 396 staggered along the length of the catheter. A loop 398, which is offset from the longitudinal axis of the catheter, is configured next to the most proximally positioned distal port 394. The proximally positioned distal port 394 is thus protected by the loop 398 and prevented from suctioning against the wall of the blood vessel. In this particular example, the shaft 404 of the catheter comprises a pair of D-shaped lumens 400, 402 (FIG. 33B), while the distally extended leg 406 comprises a single D-shaped lumen 408 (FIG. 33A). In this example, the lumen that exits into the loop is utilized as the arterial lumen, while the corresponding lumen that exits at the distal end of the catheter is utilized as the venous lumen.

Figure 34A:
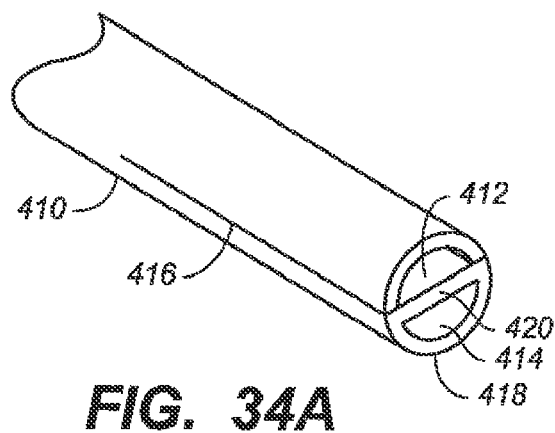
FIGS. 34A-34C illustrate a method for forming a loop-tip catheter by folding a portion of the outer wall towards the axis of the catheter body.
Figure 34B:
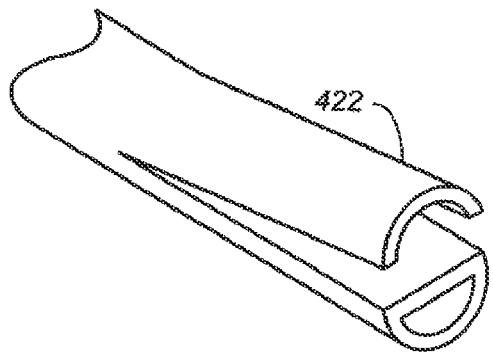
Figure 34C:
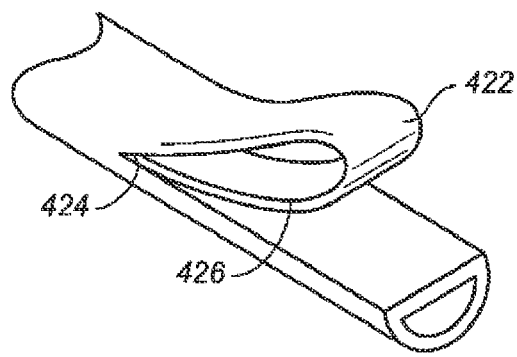

FIGS. 34A-34C illustrate one approach to fabricate a loop-tip catheter with an off-axis loop. A catheter 410 with a pair of D-shaped lumens 412, 414 is sliced at 416 from the distal end 418 along a wall of lumen 412 adjacent the septum 420 (FIG. 34A). The resulting segment 422 of the catheter wall is peeled back (FIG. 34B). The distal end 424 of the peeled back portion 422 is folded inward toward the axis of the catheter and then inserted proximally into the lumen 412 of the catheter. The created loop portion 426 is then bounded or otherwise connected to the catheter body to form the loop-tip catheter.

Figure 35:
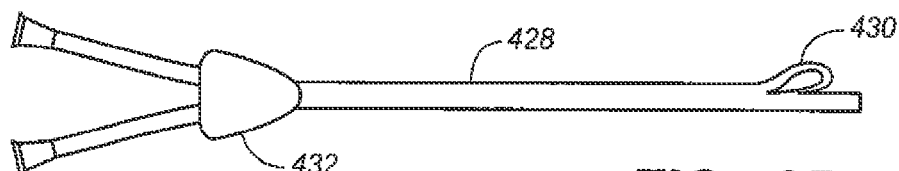
FIG. 35 illustrates one variation of a loop-tip catheter with integrated bifurcation at the distal end of the catheter.
Figure 36A:
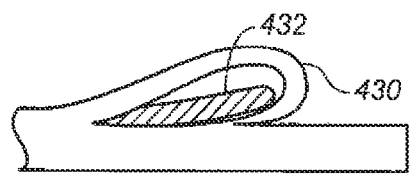
FIG. 36A illustrate the placement of a patency mandrel into the venous lumen of the loop-tip catheter to ensure the fluid channel is open. The loop at the distal venous lumen outlet prevents the patency mandrel from migrating beyond the venous outlet.
Figure 36B:
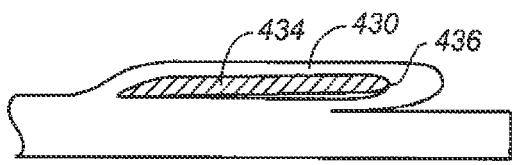
FIG. 36B illustrates the insertion of a stiff stylet into the lumen of the catheter to collapse the loop, thus allowing the user to insert the catheter into a vessel having a small diameter.

FIG. 35 illustrates one application where a loop-tip catheter 428 with an off-axis loop 430 is attached to a bifurcation 432 for utilization as a hemodialysis catheter. In addition to minimizing recirculation and preventing occlusion of the arterial inlet, the loop 430 may also serve as a stop for receiving a mandrel 432, as shown in FIG. 36A. For example, a patency mandrel can be safely inserted through the arterial inlet because the loop, acting as a safety mechanism, will prevent the mandrel from piercing the blood vessel. The patency mandrel can be utilized to clear obstructions, such as clots or fibrin formation from the arterial inlet. In addition, the mandrel can be used to collapse the loop to facilitate the inserted to the loop-tip catheter into the patient's body. As a stiff stylet 434 is advanced into the wall 436 of the loop 430, as shown in FIG. 36B, the loop 430 collapses towards the longitudinal axis of the catheter. With the loop compressed, the distal end of the catheter is easily inserted into an introducer sheath for insertion into a hollow body organ in a patient's body.

Figure 37A:
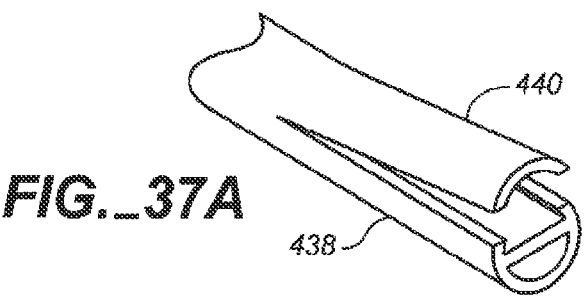
FIGS. 37A-37D illustrate one method for fabricating a catheter with a laterally extending loop.
Figure 37B:
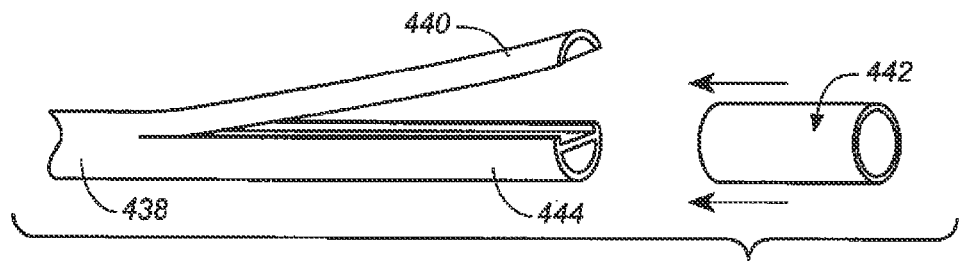
Figure 37C:
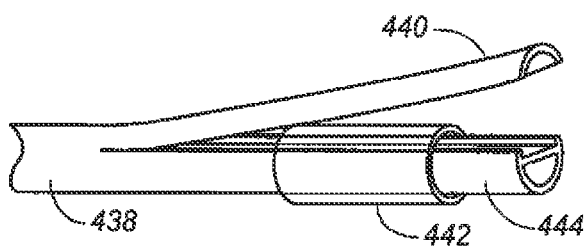
Figure 37D:
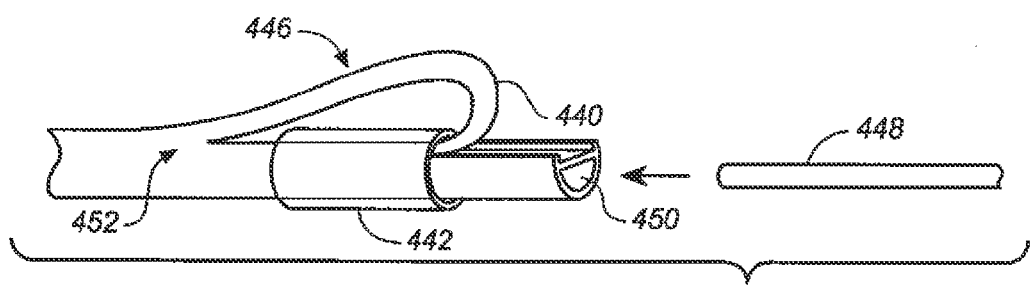
Figure 38:
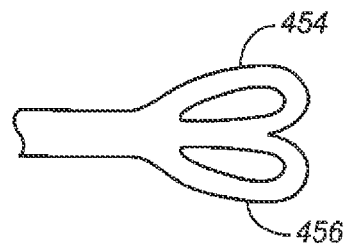
FIG. 38 illustrates one variation of a loop-tip catheter having dual loops. In this example, the catheter includes two laterally extending loops located at the distal portion of the catheter.
Figure 39:
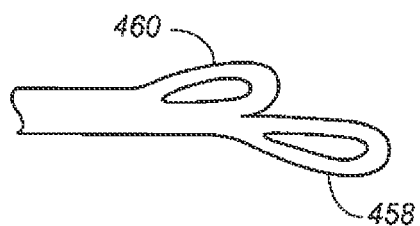
FIG. 39 illustrates another variation of a loop-tip catheter including two laterally extending loops that are staggered along the length of the catheter.
Figure 40:
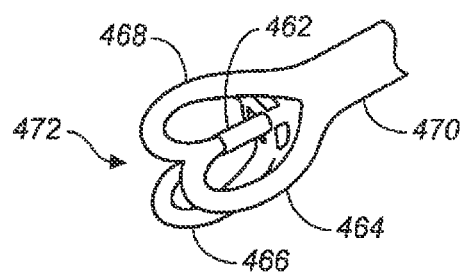
FIG. 40 illustrates yet another variation of a loop-tip catheter including three separate legs that form the loop portion of the catheter. In this particular example, the catheter comprises three separate lumens.

FIGS. 37A-37D illustrate another approach utilizing a segment of shrink tubing to fabricate a loop-tip catheter. First, the tip of a dual lumen catheter 438 is sliced open as shown in FIG. 37A. Next, the upper wall 440 is peeled back and a small piece of shrink tubing 442 is placed over the lower portion 444 of the catheter as shown in FIG. 37B and FIG. 37C. The upper wall 440 is then folded back on itself with the tip inserted into the shrink tubing 442, forming a loop 446 as shown in FIG. 37D. A mandrel 448 is then inserted into venous lumen 450 until the tip reaches past the upper wall separation point 452. Heat is applied to the shrink tubing region, allowing the material to conform between the shrink tubing and underlying mandrel. As a result, the loop is bonded into a permanent shape. The venous tip may be further formed by utilizing an additional shrink tubing operation or by simply cutting off the tip portion that extends past the loop junction. This looping technique can also be applied to create a catheter that is configured with a plurality of loop tips. The loops can be either, symmetrical 454, 456, as shown in FIG. 38, or staggered 458, 460, as shown in FIG. 39. Catheters with three or more loops can also be formed. FIG. 40 shows one example where a shrink tube 462 is utilized to bind the three sliced opened walls 464, 466, 468 on a triple lumen catheter 470 to form the triple loop 472 at the distal end of the catheter.

Figure 41A:
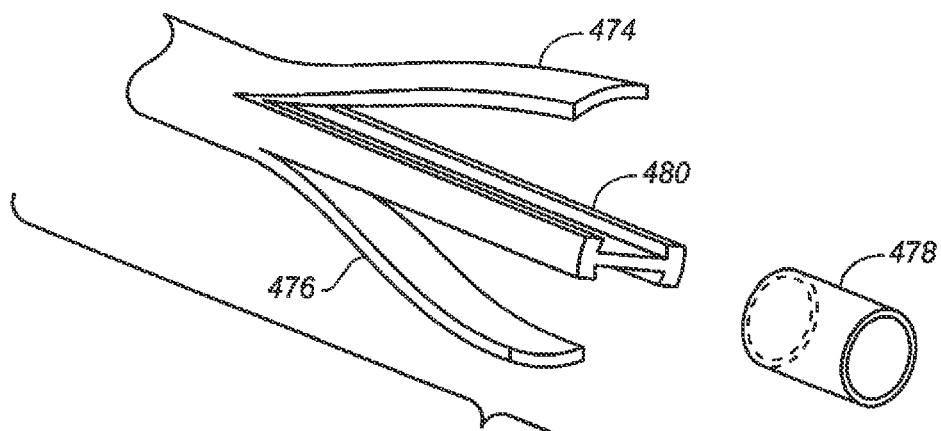
FIGS. 41A-41C illustrate an exemplary method for fabricating a catheter with two loops.
Figure 41B:
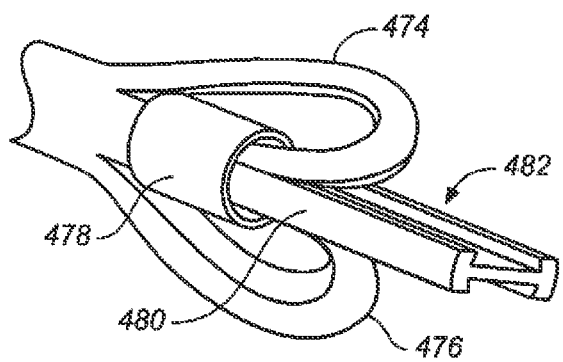
Figure 41C:
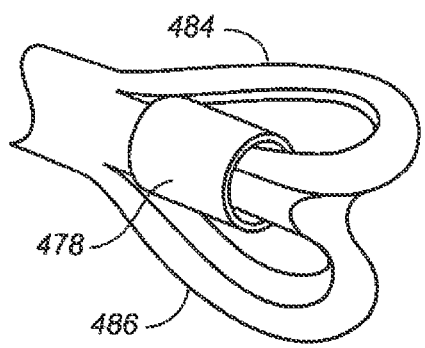

FIGS. 41A-41C illustrate a method for preparing a dual loop-tip catheter. The walls 474, 476 of the two lumens of a dual lumen catheter are sliced longitudinally from the distal end, followed by the placement of a shrink tube 478 on the remaining shaft/septum 480, as shown in FIG. 41A. The two partitioned walls 474, 476 are then looped back onto themselves and inserted into the shrink tube 478, as shown in FIG. 41B. The shrink tube 478 is then heated to bind the two walls 474, 476 to the central shaft/septum 480. After the loops are secured to the shaft/septum 480, the distally protruding section 482 of the shaft/septum can be cut off, resulting in the dual loop 484, 486 catheter shown in FIG. 41C.

In another aspect of the invention, the loop-tip concept is applied to a catheter with three or more lumens. An example of a catheter 502 with a three-legged loop 488 is shown in FIG. 42. This catheter is configured from three single lumen tubes 490, 492, 494 that are bound together, forming a circle in cross-section (i.e., each individual tube has a pie-shaped cross-sectional configuration), as shown in FIG. 43. The distal portion 496, 498, 500 of each of the tubes is folded back onto itself at a distal end thereof to form a partial loop. The proximal and medial portions of the tubes 496, 498, 500 are then bonded together to form the catheter 502 shown in FIG. 42. A three-legged loop acts to protect the arterial inlet from sidewall suction.

A third leg can be created in a dual lumen configuration to provide additional protection against side wall occlusion on a hemodialysis type catheter. An example of a dual lumen catheter 504 with a three-legged loop 506 is shown in FIG. 44A. The venous lumen 510 extends into one of the three legs and exits 508 at the distal end 510 of the catheter 504. The arterial lumen 512 has a distal opening located between the trifurcation 514 of the three legs. An exemplary approach to fabricate such a catheter is shown in FIG. 44B, where a D-shaped tubing 516 is bonded to an arc C-shaped extrusion 518. The two parts are bonded down the length of the shaft. First, the D-shaped tubing 516 and the arc C-shaped extrusion 518 are bonded to each other at their respective distal ends 520 using hot die or other bonding methods well know to one of ordinary skill in the art. The two parts 516, 518 are then bent back from each other and laid out as shown in FIG. 45. The C-shaped extrusion 518 is split 522 at the distal end. Supporting mandrels are then placed in the two lumens. The shafts are bonded together using a shrink-down technique, leaving the distal portion unbound to form the loop portion of the catheter.

Figure 46A:
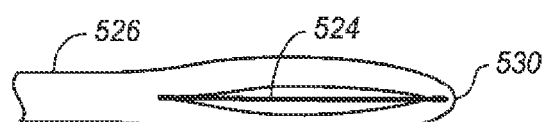
FIG. 46A illustrates a loop-tip catheter, including an embedded wire element for manipulating the loop structure.
Figure 46B:
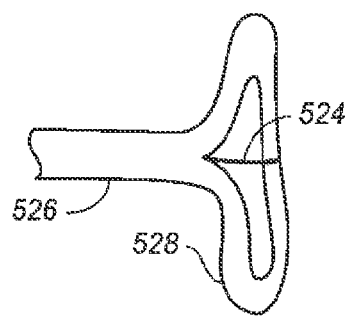
FIG. 46B shows the loop-tip catheter of FIG. 46A with the embedded wire element retracted, forcing the loop to expand away from the axis of the catheter.

In another aspect of the invention, the loop-tip catheter further comprises a mechanism to allow the user to manipulate the loop structure. For example, a wire may be integrated into the catheter to allow the user to extend or contract the loop at the distal end of the catheter. The wire may pass through either of the two lumens in a dual lumen catheter, or can be supported within a separate lumen/channel. In one variation, wire 524 extends from the proximal end of the catheter through the length of the catheter, passes the center of the loop and connects to the distal portion 530 of the loop 528. When the user advances the wire 524 into the catheter 526, the loop 528 extends distally and collapses towards its longitudinal axis, as shown in FIG. 46A. When the user retracts the wire 524, the loop 528 first expands away from the axis of the catheter and then collapses onto itself, as shown in FIG. 46B. One of ordinary skill in the art having the benefit of this disclosure would appreciate that other interlinking mechanisms (e.g., rods, etc.) may also be utilized to allow the user to control the shape of the catheter loop.

Figure 47:
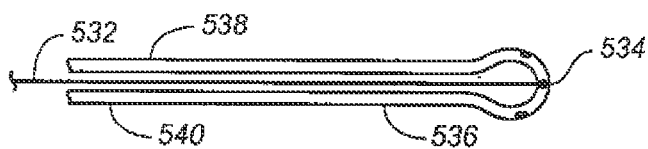
FIG. 47 illustrates an exemplary method to fabricate a loop-tip catheter with an embed wiring to control the loop position. The distal end of a wiring is coupled to a midsection of a catheter. The catheter is then folded over the wiring.
Figure 48:
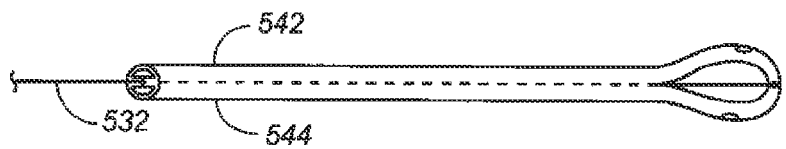
FIG. 48 illustrates a loop-tip catheter configured from the parts shown in FIG. 47.
Figure 49A:
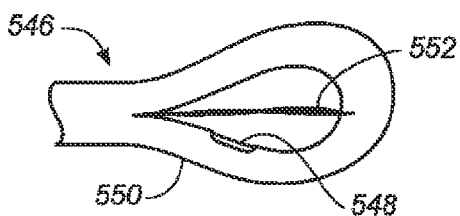
FIG. 49A illustrates one variation of a loop-tip catheter with a control wiring coupled to the distal loop.
Figure 49B:
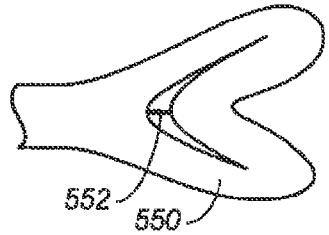
FIG. 49B illustrates the loop-tip catheter of FIG. 49A with its control wiring retracted, forcing the distal portion of the loop to collapse inwardly and, thus, covering the arterial inlet on the inner circumferential surface of the loop.

FIG. 47 illustrates one example of fabricating a catheter with a control wire. The wire 532 is coupled to the midpoint 534 of a catheter 536. The two ends 538, 540 of the catheter are folded onto the wire 532 and bonded to each other to form a loop-tip catheter. As the result the wire 532 is captured between the two folded segments 542, 544 of the catheter, as shown in FIG. 48. In one variation, a wired catheter 546 is configured with an orifice 548 on the inner surface of the loop 550, as shown in FIG. 49A. The user can cover the orifice by advancing the control wire 552 to collapse loop 550 axially. In another approach, the user can retract the wire 552 to cause the distal portion of the loop to collapse onto the orifice 548, as shown in FIG. 49B. As a result, the user can manipulate the control wire to cover the orifice and prevent tissue formation over and/or within the orifice to maintain the patency of the orifice when it is not in use.

Figure 50A:
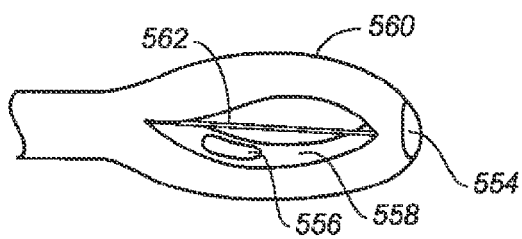
FIG. 50A illustrates another variation of a loop-tip catheter with control wiring. In this variation, the catheter includes a distal venous lumen opening located at the tip of the catheter, and a distal arterial lumen opening located on an inner circumferential surface of the loop.
Figure 50B:
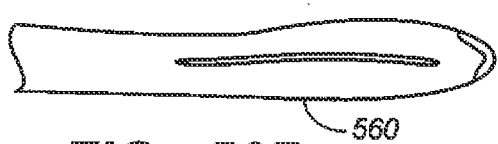
FIG. 50B shows the loop-tip catheter of FIG. 50A extended by the control wire. As a result, the arterial inlet is covered, while the infusion path (i.e., venous lumen) remains open.
Figure 50C:
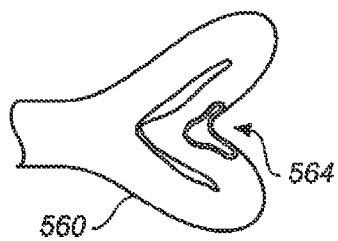
FIG. 50C shows the loop-tip catheter of FIG. 50A contracted by the control wire to form a bowed shape. As a result, the arterial inlet is covered by the distal portion of the loop.

In another variation, a wired catheter is configured for a hemodialysis-type application, with a distal outlet 554 for accessing the venous lumen, and an arterial inlet 556, located on the inner surface 558 of the loop 560, for accessing the arterial lumen, as shown in FIG. 50A. The loop 560 is manipulated by a control wire 562 to close off and protect the arterial inlet between dialysis sessions. For example, the arterial inlet is protected by advancing the control wire to collapse the loop 560, as shown in FIG. 50B. Collapsing the loop also permits easy insertion into an introducer sheath during deployment. The user may also cover the arterial inlet by retracting the wire 562 to force the loop 560 to bow inward and cover the inlet, as shown in FIG. 50C. The bowed shaped formation 564 may serve to peel back fibrin sheath formation around the tip of the catheter.

In another variation, the catheter 570 is configured with an apex of the catheter positioned within the center 566 of a cut-away section 568, as shown in FIG. 51. The tubing 574 is looped such that the center 566 of the cut-away zone 568 is at the apex of the tip. This design decreases the distal tip profile and allows for easier insertion into a small channel. In addition, the cut-away zone can be further configured with a tapered 576, 578 rather than a straight edge cut, such that the tip becomes even more streamlined for insertion, as illustrated in FIG. 52. This design allows the user to close both of the openings by retracting the control wire 580. Furthermore, adding an additional arterial inlet 580 on the inner surface of the loop does not affect the symmetry of the tip, as shown in FIG. 53. Optionally, the distal arterial inlet 582 is occluded using a heat process, thus allowing the side port 580 located on the inner surface of the loop 584 to serve as the primary arterial inlet.

The control wire can be manipulated from the proximal end of the catheter in a variety of ways to improve the efficiency and patency of the catheter. For example, if the tip of the catheter were to become occluded, the wire could be pushed in a distal direction or pulled in a proximal direction to break free any occluding formations. The tip itself would act as a constraint of motion to prevent damage to the venous wall and to prevent potential interference with the heart. Such manipulation with the wire would also be useful to protect/close the arterial inlet between dialysis sessions. The control wire also allows the user to destroy fibrin sheath that forms over the side wall of the blood vessel. A typical hemodialysis catheter that has been implanted for an extended period of time becomes prone to arterial insufficiency due to fibrin sheath formation around the distal portion of the catheter. To remove the fibrin sheath, the implanted catheter is first removed, and then an angioplasty balloon is positioned below the fibrin sheath, inflated, and then pulled back to destroy/remove the fibrin sheath.

Figure 55:
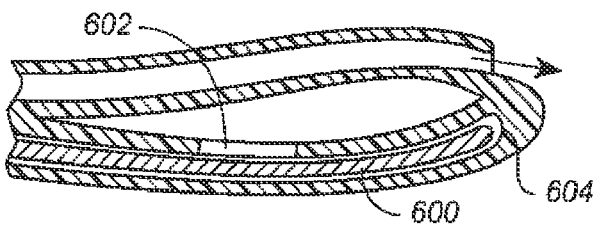
FIG. 55 illustrates the use of a mandrel inserted into the arterial lumen to straighten the catheter tip. The straightening of the catheter tip forces the loop to collapse and covers the arterial inlet. The deformation of the loop caused by the catheter straightening may also facilitate fibrous tissue from breaking off the surface of the catheter.

FIGS. 54A-54C is an example illustrating the use of a control wire to contract and expand the loop to remove and/or break apart fibrin sheath without the need for a catheter exchange. Once user detects that fibrin has form around the distal tip of the implanted catheter 590 (FIG. 54A), the tip 592 of the catheter is pulled back via a wire 594, causing the tip to buckle (FIG. 54B). As the tip 592 is pulled in a proximal direction, the fibrin sheath 596 is broken-up, after which the wire 594 is advanced distally, pushing the loop 598 back to its straightened position, and leaving the tip free from fibrin sheath (FIG. 54C). FIG. 55 illustrates another approach to protect the arterial inlet from occlusion. A disposable mandrel 600 is used to strengthen the tips, thus protecting the arterial inlet 602 between dialysis sessions. The mandrel is inserted into the arterial lumen and pushed against the distal end 604 of the arterial lumen. The lumen wall at the distal end of the catheter prevents the tip of the mandrel from engaging the vessel wall. The mandrel clears any obstruction in the arterial lumen and provides protection to the arterial inlet.

Figure 56:
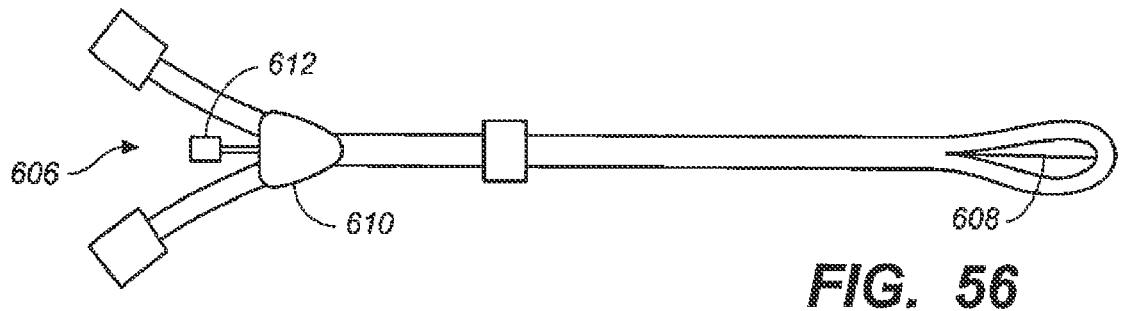
FIG. 56 illustrates another configuration of a loop-tip catheter with an integrated control shaft.
Figure 57:
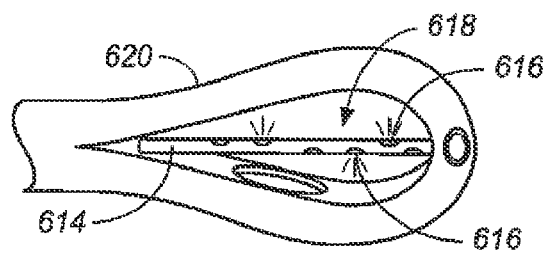
FIG. 57 is an expanded view of loop portion of the catheter of FIG. 56.

In one variation a control interface 606 is provided at the proximal end of the catheter to allow the user to easily manipulate the control wire 608. For example, the proximal portion of the control wire 608 may pass through a bifurcation 610 connected at the proximal end of the catheter, as shown in FIG. 56. A knob 612 or handle is connected to the proximal end of the control wire 608 to give the user better control over the control wire 608. In one embodiment, the control wire comprises a hollow cannula 614 with holes 616 at its distal end to facilitate localized delivery of heparin or other anticoagulant. Medications are injected into the proximal end of the control wire and then flushed into the center 618 of the catheter loop 620.

Figure 58A:
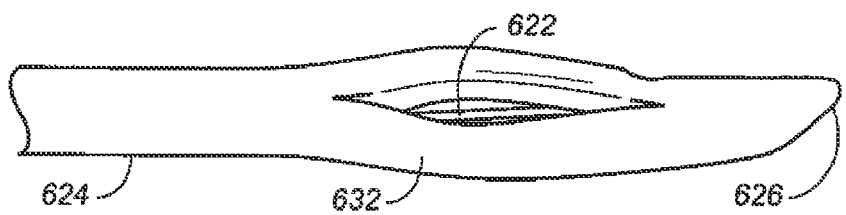
FIGS. 58A-58D show another variation of a loop-tip catheter with a closed distal tip. The drawings illustrate the retraction of the control wire, which forces the loop at the distal end of the catheter to collapse.
Figure 58B:
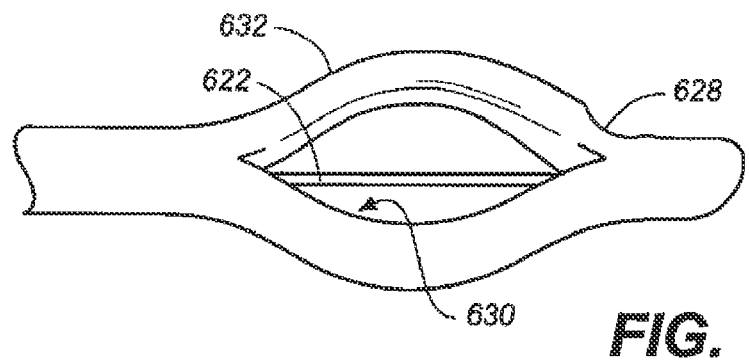
Figure 58C:
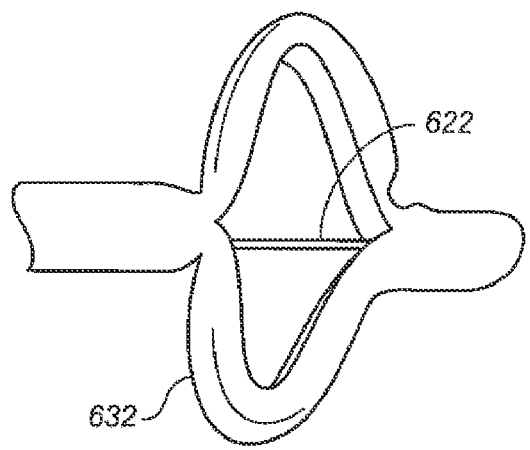
Figure 58D:
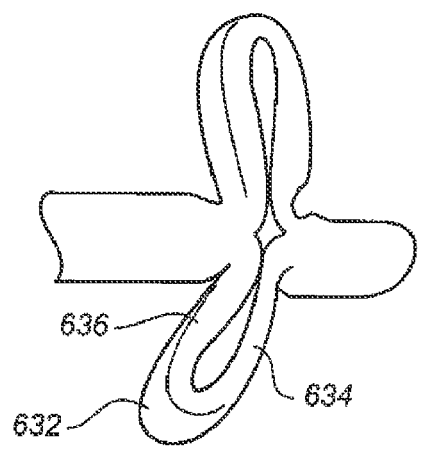

In another variation, the control wire 622 is implemented on a loop-tip catheter 624, including a tapered atraumatic distal end 626, as shown in FIG. 58A. The dual lumen catheter has a venous outlet 628 located on the outer surface of the loop and arterial inlet 630 located on the inner surface of the loop. FIG. 58A shows the control wire 622 advanced distally to straighten the loop 632 for insertion into an introducer sheath. FIG. 58B shows the control wire 622 partially retracted to maximize fluid intake at the arterial lumen 630. FIG. 58C shows the control wire 622 further retracted, forcing the loop 632 to expand away from the catheter axis. FIG. 58D shows the control wire 622 in the fully retracted position with the distal portion 634 of the loop collapsed onto the proximal portion 636 of the loop.

Figure 59A:
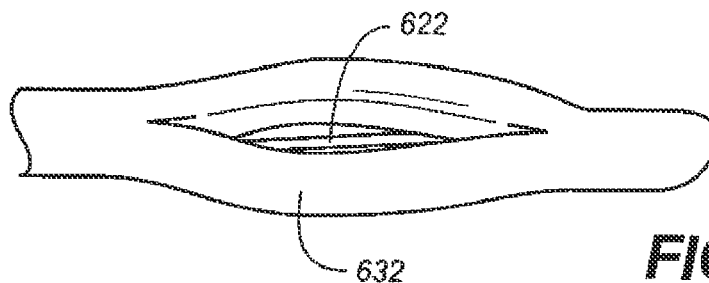
FIG. 59A illustrate a loop-tip catheter, which includes a control wire, in a relaxed state.
Figure 59B:
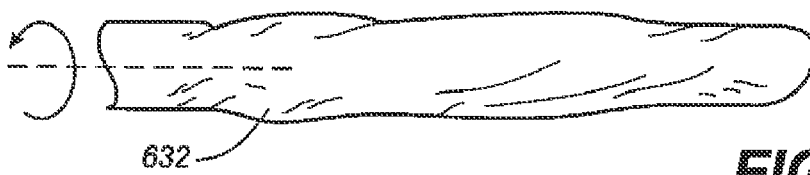
FIG. 59B illustrates the loop-tip catheter of FIG. 59A with its distal tip portion rotated in relation to the proximal portion of the catheter. The twisting motion caused by the rotation of the control wire forces the opening on the catheter to close.

In another variation, a wire embedded in a loop-tip catheter is configured such that a twisting motion applied to the wire 622 results in a twisting of the catheter's loop tip. In one application the twisting motion allows the user to close the arterial inlet. FIG. 59A shows the loop 632 in a relaxed state. FIG. 59B shows the rotation of the wire, resulting in the twisting of the loop 632 at the distal end of the catheter.

Figure 60:
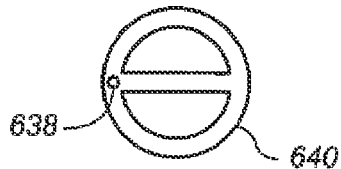
FIG. 60 is a cross-sectional view of a catheter shaft, showing one variation for the placement of a control wire. In this example, a channel off set from the axis of the catheter is provided to house the control wire.
Figure 61:
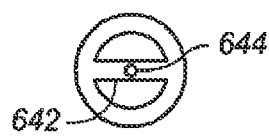
FIG. 61 is a cross-sectional view of a catheter shaft, showing another variation for the placement of a control wire. In this example, a lumen is positioned along the central axis of the catheter to house the control wire.
Figure 62:
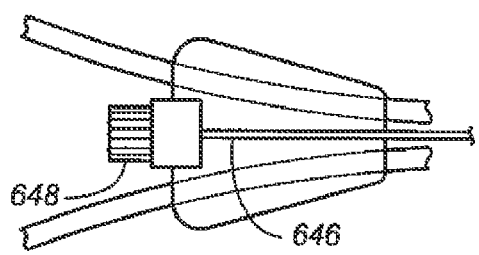
FIG. 62 illustrates a built-in knob positioned over the bifurcation for controlling a wire or flexible rod that is coupled to the loop at the distal end of the catheter.

The actuating/control wire may be placed in an existing lumen or it may be disposed within a separate wire lumen/channel. In one variation, the wire lumen 638 is offset from the central axis of the catheter 640 (FIG. 60). In another variation, the wire is placed within the septum 642 on the central axis 644 of the catheter (FIG. 61). Furthermore, the wire 646 may be connected at the proximal end thereof to a knob 648 or other mechanical instrument to allow easy manipulation by the user (FIG. 62). The knob or other mechanical instrument may be positioned within or adjacent to a bifurcation element.

Figure 63:
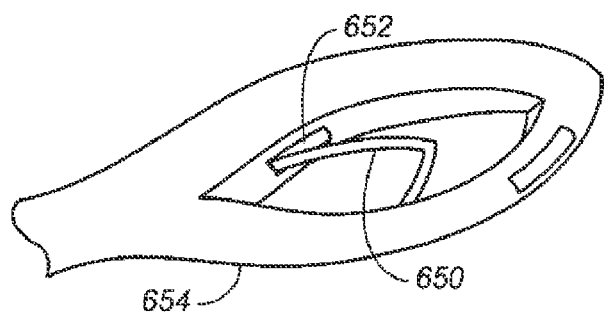
FIG. 63 illustrates another variation of a loop-tip catheter including a mechanism for protecting the arterial inlet. In this example, a wire is strung through the arterial lumen, out of the arterial inlet and into a pinhole positioned on the opposite side of the loop. The wire may be utilized to clean out the arterial inlet.
Figure 64:
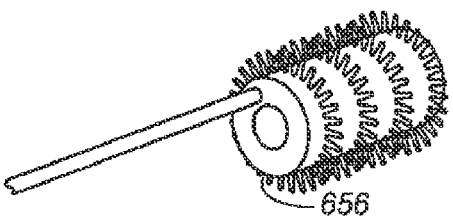
FIG. 64 shows an over-the-wire brush that can be deployed over the arterial lumen wire shown in FIG. 63 to clear the arterial inlet.

FIG. 63 shows another design where a wire 650 is placed through the arterial lumen, exiting through the arterial inlet 652 and into a venous "pin hole" located across from the arterial inlet on the opposite side of the loop 654. The wire 650 is used to manipulate the loop 654 and to fortify the separation of venous and arterial branches. Movement of the wire removes occlusions from the arterial lumen. The wire may also serve as a guide for introducing other instruments, such as brushes 656 (FIG. 64) to clean the lumen and/or arterial inlet 652. In addition, the wire 650 may be vibrated at a high frequency to shake off any fibrin sheath from the tip of the catheter. In another variation, the wire could itself have a lumen/channel for delivery of an antithrombogenic substance or other types of drugs to the tip in a localized manner.

Figure 65:
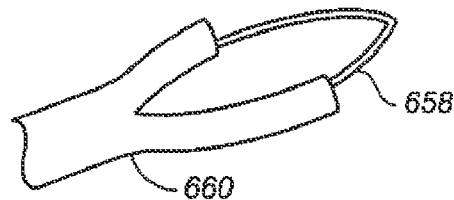
FIG. 65 illustrates another variation of a loop-tip catheter, which comprises a connector attached to the distal end of a split-tip catheter to form a loop that separates the catheter tips.
Figure 66:
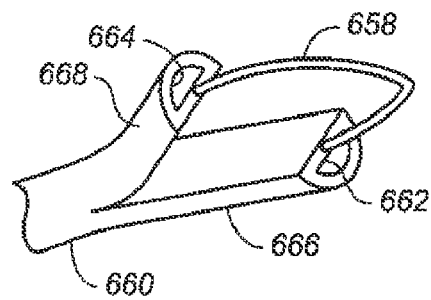
FIG. 66 illustrates another variation where the connector is coupled to the walls of the two separated catheter tips.
Figure 67:
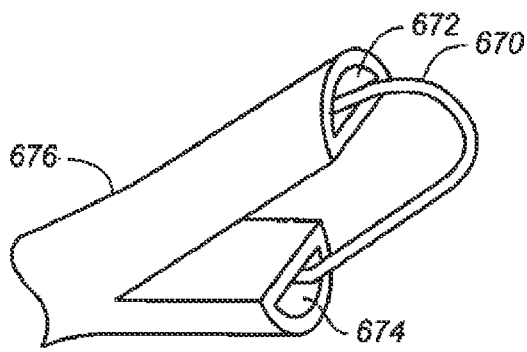
FIG. 67 illustrates yet another variation where the two legs of the connector/loop extend into the arterial and venous lumens of the catheter.
Figure 68:
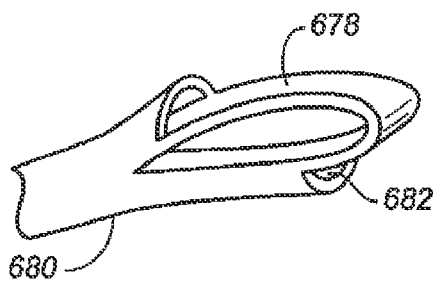
FIG. 68 illustrates another variation where a flat edge septum is utilized to form a loop at the distal end of a dual lumen catheter to protect the arterial inlet and minimize recirculation.
Figure 69:
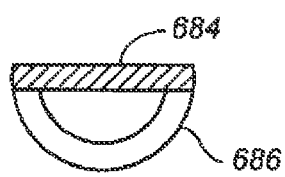
FIG. 69 is a cross-sectional view at the distal end of the venous branch extension from FIG. 68, showing the position of the septum.

In another aspect of the invention, the loop-tip catheter utilizes a hybrid design, which comprises two or more materials to form the loop and the catheter. This design may provide additional mechanical properties to the tip of the catheter. In one variation, the looping portion 658 comprises one material while the catheter portion 660 comprises another material, as shown in FIG. 65. The looping portion 658 may be connected directly to the catheter 660. For example, the looping portion 658 may comprise a metallic material and connects directly onto the distal ends 662, 664 of the bifurcating branches 666, 668 of the catheter, which may comprise polyurethane (FIG. 66). In another variation, the looping portion 670 is inserted within the lumens 672, 674 of the catheter 676, as shown in FIG. 67. In one example, the looping portion 670 is configured to be free floating in the lumens 672, 674 of the catheter. Optionally, the two ends of the looping portion inserted with the lumens of the catheter may be coupled thorough the septum within the shaft of the catheter to prevent it from accidentally dislodging from the catheter body. In yet another variation, the flat edges of the septum forming the loop 678 of the catheter may comprise a different material (e.g., higher durometer material, etc.) than the material forming the body 680 of the catheter. As illustrated in FIG. 69, a cross-section taken at the venous outlet 682 of the catheter of FIG. 68 shows the flat edge septum 684 and the rounded catheter outer wall 686 are comprised of two different materials.

Figure 70A:
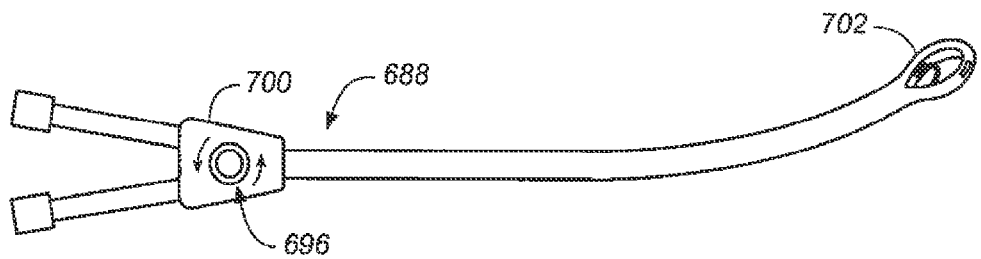
FIG. 70A illustrates another variation of loop-tip catheter with a built-in string system for clearing the arterial lumen opening.
Figure 70B:
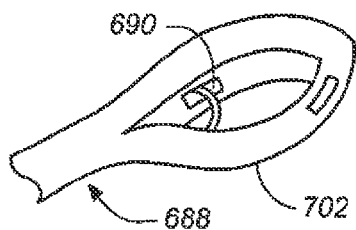
FIG. 70B is an expanded view of the distal portion of the loop-tip catheter of FIG. 70A, showing a wire that extends through the arterial lumen, exiting the arterial inlet and entering the venous lumen through a pin hole on the inner surface of the loop.
Figure 70C:
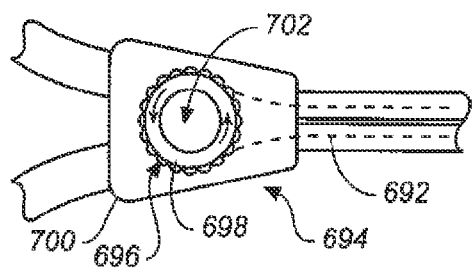
FIG. 70C is an expanded view of the bifurcate on the loop-tip catheter of FIG. 70A, illustrating the rotary dial for controlling the tension of the wire.

In another aspect of the invention, the loop-tip catheter 688 comprises a string that extends through the length of the catheter to allow the user to manipulate the loop 702 at the distal end of the catheter. In one example (FIG. 70A), a string is threaded through the arterial lumen, the arterial inlet (FIG. 70B), and the venous pin hole, and back down the venous lumen. The string 692 may be very thin (e.g., "floss-like"), and is wrapped at the proximal end 694 of the catheter around a spool 696 or the like, which is connected to a knob 698 on the outer portion of a bifurcation element 700 (FIG. 70C). The string 692 can be circulated through the catheter by turning the knob 698. In one variation, the string or floss is pre-coated with heparin or other medication before it is integrated within the catheter. For example, the string or floss may be coated or embedded with anti-infection or anti-thrombin agents. In another variation, a port 702 is integrated into the knob/spool 696 at the bifurcation 700 to hold drugs/coatings/heparin or other substances that may advantageously be circulated throughout the catheter. The port 702 may be accessed by inserting a needle through a septum. Thus, in addition to acting as a mechanical means of dislodging arterial inlet or venous outlet occlusions, the string 692 may also serve as a drug delivery device by absorbing the drug or other substance as it passes through the port, delivering the drug or other substance throughout the catheter. As one of ordinary skill in the art having the benefit of this disclosure would appreciate, this drug delivery method can be expanded to various multiple lumen catheter designs, irregardless of the tip geometry.

In another variation, the string is coupled to a knob and connected to the inner wall of the loop, such that when the knob is turned, the string will tighten. As the string is tightened, the loop wall of the loop across from the arterial inlet will be pulled toward the arterial inlet, eventually covering the arterial inlet.

Figure 71A:
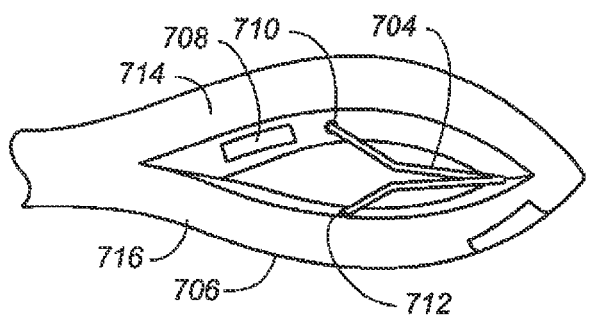
FIG. 71A illustrates another variation where a shaped wire positioned within the catheter loop is configured for collapsing the two inner walls in the loop.
Figure 71B:
FIG. 71B shows the shaped wire from FIG. 71A.
Figure 71C:
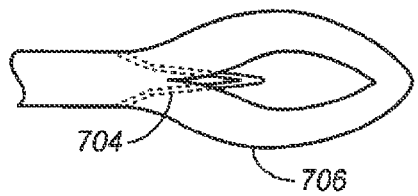
FIG. 71C shows that the proximal displacement of the shaped wire collapses the walls on the arterial and the venous side together, resulting in the arterial inlet being covered.

In another variation, a shaped wire 704 is employed, as shown in FIG. 71A, to compress the loop 706 in order to close the arterial inlet 708 between treatments. Two pin holes 710, 712 are made on the inner wall of the catheter loop 706 on both the arterial 714 and venous 716 sides. A shaped wire 704, shown in FIG. 71B, is threaded through pin holes 710, 712 toward the proximal end of the catheter. When shaped wire 704 is displaced in the proximal direction, the catheter loop 706 collapses, and the arterial inlet is covered by the venous sidewall, as shown in FIG. 71C. A rod or a wire, which can be slidably disposed within one of the catheter lumens, may be coupled to the shaped wire to allow the user to control the displacement of the shape wire from the proximal end of the catheter.

Figure 72:
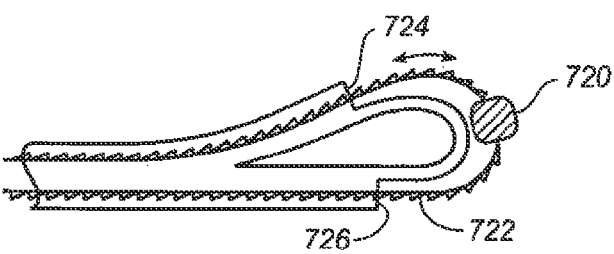
FIG. 72 illustrates one variation of a mechanism for displacing a plug between the arterial inlet and the venous outlet on a loop-tip catheter.
Figure 73A:
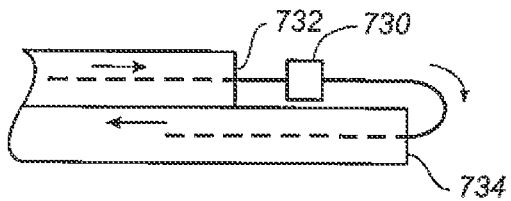
FIGS. 73A-73D illustrates the displacement of the plug to selectively close the arterial inlet or the venous outlet.
Figure 73B:
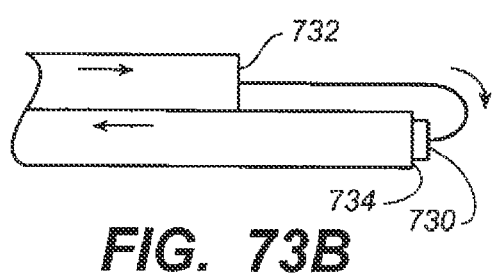
Figure 73C:
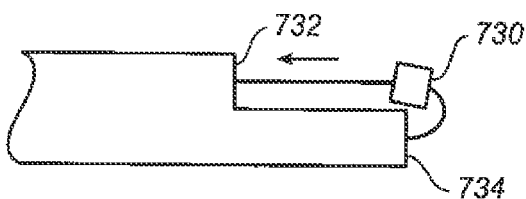
Figure 73D:
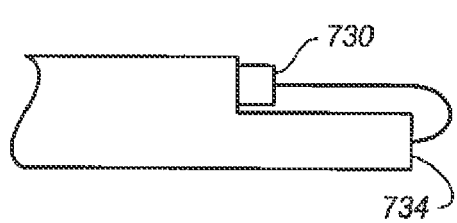

In another aspect of the invention, a plug 720 is attached to a string 722 and is threaded through both the arterial and the venous lumen to allow the user to selectively close or open the catheter lumens. The plug 720 positioned between the arterial 724 and venous 726 openings, as shown in FIG. 72, may be utilized to insure patency of the catheter lumens. Movement of the string in either direction moves the plug from one side of the loop-tip to the other. This allows the user to selectively block passage of fluid through either the arterial or the venous opening. Movement of the plug from one opening to the other may also act to remove any clot formations. In FIGS. 73A-73D, a movable plug 730 is being applied on another variation of a dual lumen catheter with staggered lumen openings. FIG. 73A shows the plug 730 being displaced in the distal direction toward the distally positioned venous outlet 732. FIG. 73B shows the plug 730 sealing the venous outlet 732. FIG. 73C shows the plug 730 being removed from the venous outlet 732 and retracted toward the proximally positioned arterial inlet 734. FIG. 73D shows the plug 730 sealing the arterial inlet 734.

Figure 74A:
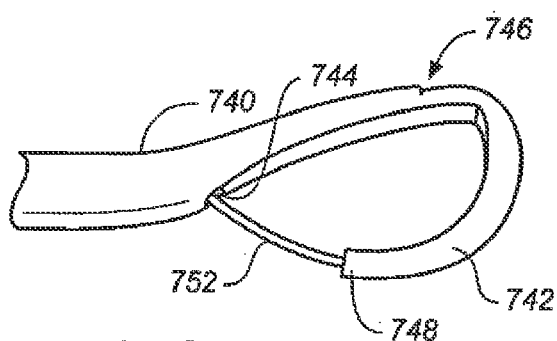
FIG. 74A illustrates another variation of a loop-tip catheter. In this example, the tip of the loop can be used as a plug to close the arterial inlet.
Figure 75:
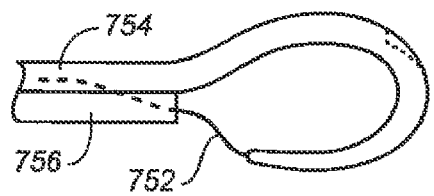
FIG. 75 illustrates one variation for implementing a wire for retracting the tip of the catheter loop. In this example, the wire is passed through the venous lumen.
Figure 74B:
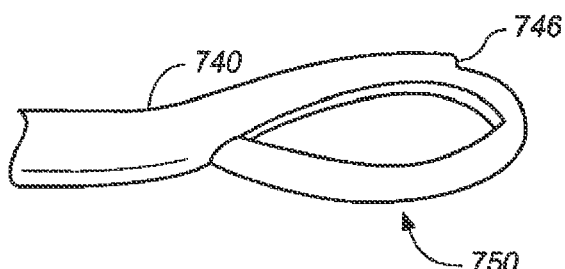
FIG. 74B shows the loop-tip catheter of FIG. 74A with the tip portion of the loop retracted into the arterial inlet.
Figure 76:
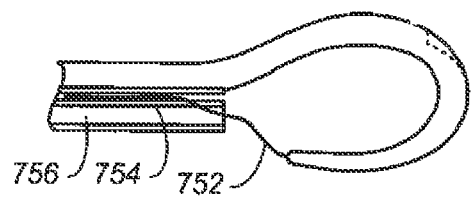
FIG. 76 illustrates another variation for implementing a wire for retracting the tip of the catheter loop. In this example, the wire is passed through a dedicated channel, which is located between the arterial and venous lumens.

In another aspect of the invention, the loop-tip catheter comprises a variable loop, which can be adjusted in size. In one variation, the loop-tip catheter 740 is created by pulling a venous tip 742 toward a proximal arterial inlet 744, as shown in FIG. 74A. A venous outlet 746 is positioned on the venous tip proximal to the distal end 748 of the venous tip, such that when the venous tip 742 is pulled in a proximal direction, a loop configuration 750 is formed, as shown in FIG. 74B. The venous outlet 746 is located on the outside surface of the loop configuration. A wire 752 is embedded in the distal end of the venous tip and is routed to the proximal end of the catheter 740 through either an independent lumen/channel or one of the arterial or venous lumens. FIG. 75 shows an example where the wire 752 is routed through the septum separating the lumens and down the venous lumen 754. FIG. 76 show another example where the wire 752 is routed through an independent channel 754 positioned between the venous 754 and the arterial 756 lumens. The catheter may be configured in such a way that when the wire is pulled in a proximal direction, the distal end of the venous tip moves toward the arterial inlet. If it is desired to close the arterial tip, such as between dialysis treatments, the distal end of the venous tip can be pulled into the arterial inlet, effectively blocking any fluid (e.g., blood) from entering.

Another method of protecting the arterial inlet comprises placing a balloon on or within the loop of the loop-tip catheter. The balloon can then be inflated to protect the lumen openings that are positioned within the inner surface of the loop. For example, in between dialysis sessions, the balloon can be inflated, such that it covers the arterial inlet. The balloon may also be expanded to remove particles or tissues that have built-up within the loop. In addition, the balloon may be used to expand the loop structure to break off tissues built-up around the loop.

In one variation, the balloon 760 is attached on a flexible cannula 762 positioned within the loop 764 of the catheter 766 as shown in FIG. 77A. The proximal portion of the cannula extends through the length of the catheter and into the loop 764 at the proximal end of the catheter body. The balloon 760 can then be inflated by injecting fluids into the proximal end of the cannula 762. When the balloon 760 is fully inflated, it compresses against the inner wall of the loop 764, thus covering any openings 768 thereon, as shown in FIG. 77B. The proximal end of the loop-tip catheter 766 may be further configured with a bifurcation 770. A septum port 772, which is in fluid communication with the flexible cannula 762, is integrated on the bifurcating element 770 to allow the user to inflate the balloon 760 by injecting fluid into the septum port 772, as shown in FIG. 78. One of ordinary skill in the art having the benefit of this disclosure would appreciate that instead of the cannula, channels or catheters may be built into the catheter shaft to provide a path for inflating and deflating the distally positioned balloon. Other interfaces that are well known to one of ordinary skill in the art may also be utilized to control fluid injection for inflating the balloon.

The balloon can be inflated with saline or other fluids. In one variation, the balloon comprises a semi-permeable material, so that when the balloon is inflated with a solution comprising heparin or other medications, the porosity of the balloon permits slow release of the medication within the loop. In another variation, the position of the balloon is configured such that contraction thereof would be away from the inlet (e.g., the deflated balloon is positioned proximal the arterial inlet). FIG. 79A illustrates one example where the balloon 780 is positioned at the base 782 of the loop 784, proximal the arterial inlet 786. This configuration may prevent the deflated balloon 780 from interfering with the arterial inlet 786 during treatment (i.e., aspiration through the arterial inlet). In between treatment sessions, the balloon 780 can be inflated, as shown in FIG. 79B, to cover the arterial inlet.

In another variation of the loop-tip catheter design, the catheter comprises triple lumens and a low profile loop positioned at the distal end of the catheter to protect the arterial inlet. An example of the low profile loop-tip catheter 790 is shown in FIG. 80. In this example, the catheter comprises three lumens 792, 794, 796, as shown in FIG. 81A. In one particular variation, the catheter has an outer diameter, OD1, of 0.193 inches, an inner diameter, ID1 of 0.132 inches, and a wall thickness, T1, of 0.024 inches. The two septa, each has a thickness, W1, W2, of 0.015 inches. The center lumen has a width, W4, of 0.04 inches, while the two adjacent lumens, each has a thickness, W3, W5, of 0.037 inches. The center lumen 794 opens 998 into the loop 800 positioned at the distal end of the catheter, while the walls supporting the two adjacent lumens extend distally to form the loop 800. The distally extending portion of the catheter may be tapered. The two adjacent lumens 792, 796 exit at the distal end of the catheter 802, 804, as shown in FIG. 81B. In the particular variation shown, the distal tip has a outer diameter, DO2, of 0.158 inches, a inner diameter, ID2, of 0.104 inches, and a wall thickness, T2, of 0.024 inches.

In one variation, the low profile loop-tip catheter is configured from a standard triple lumen catheter 810 (i.e., one in which the cross-sectional configuration of the lumens features one rectangular lumen between two D-shaped lumens). The wall of the center lumen 812 is cut a pre-determined distance from the distal end to create two separate tips 814, 816, as shown in FIG. 82. The tips 814, 816 are then joined together at the tip portion to form the loop. In one variation, a separate through-hole is provided in one of the inside edges of the distal venous tips to permit passage of a wire therethrough and into the arterial lumen.

Figure 83A:
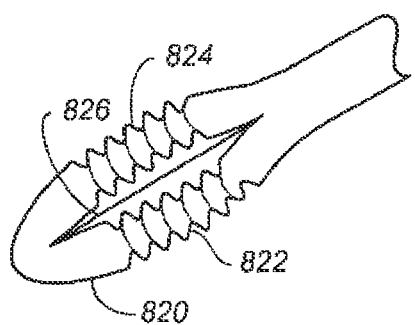
FIG. 83A illustrates another variation of a loop-tip catheter which comprises corrugated segments along the length of the loop. The corrugated segments allow the dimension of the loop to be expanded or contracted.
Figure 83B:
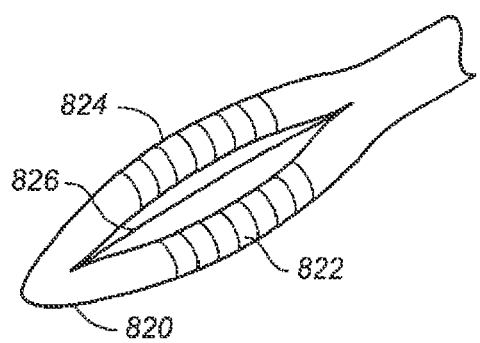
FIG. 83B shows the loop-tip catheter of FIG. 83A with its loop in an expanded state.
Figure 84A:
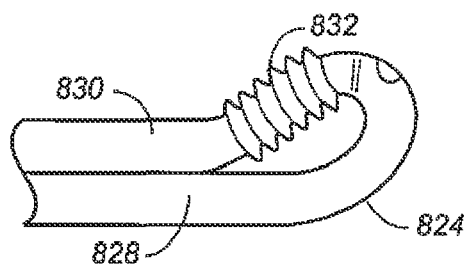
FIG. 84A illustrates another variation of a corrugated loop-tip catheter. In this particular example, only one corrugated segment is implanted along the length of the loop. The loop is shown in a contracted state.
Figure 84B:
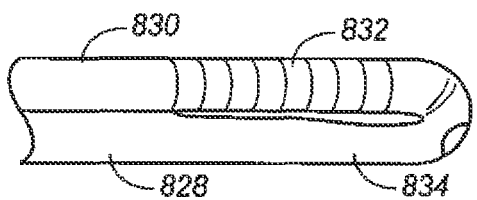
FIG. 84B shows the corrugated loop-tip catheter of FIG. 84A in an expanded state.

In another variation of the loop-tip catheter, the loop portion comprises a corrugated section. The corrugated section provides an increase in the range of motion when the loop is being expanded or compressed. An actuator may be integrated within the catheter for manipulating the configuration of the loop. An example, shown in FIG. 83, comprises a loop 820 with two corrugated section 822, 824. An actuating wire 826 threaded through the length of the catheter is provided to allow the user to expand or contract the corrugated loop 820. The distal end of the actuating wire 826 is coupled to the distal portion of the loop. When the user retracts the actuating wire, the distal portion of the loop is displaced proximally and the loop is contracted. When the actuating wire 826 is advanced distally, the distal portion of the loop 820 is pushed out and the loop 820 expands, as shown in FIG. 83B. The corrugated loop-tip catheter may be configured with one or more arterial inlet and venous outlet. The inlets/outlets may be placed on various locations along the length of the loop. In another example, a catheter is configured with a single functional lumen 828 for infusing/aspirating fluids, while a second lumen 830 is utilized to extend the loop structure, as shown in FIG. 84A. In this particular design, the loop 834 comprises a single corrugated section 832. When the user wishes to extend the loop 834, fluid is injected into the expansion lumen 830 to pressurize the expansion lumen 830. As the expansion lumen pressurizes, the corrugated section 832 expands. As a result, the loop 834 will straighten in the distal direction as shown in FIG. 84B. To contract the corrugated section 832 to form the loop, fluids are suctioned out of the expansion lumen 830.

Figure 85:
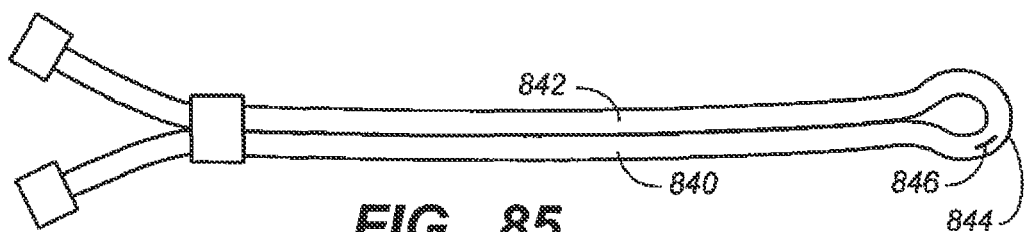
FIG. 85 illustrates another variation of a loop-tip catheter implemented with a slit valve.

In another aspect of the invention, the loop at the distal end of the loop-tip catheter is configured as a shunt at the distal end of the catheter, such that the entire catheter can be flushed from the proximal end. This feature allows the user to regularly flush out the catheter to maintain patency and/or minimize risk of lumen infection proliferation. In one variation, the catheter comprises two lumens 840, 842 that extend down the length of the catheter. The two lumens 840, 842 that are in fluid communication through the loop 844 at the distal end of the catheter, as shown in FIG. 85. The catheter further comprises a valve 846 positioned on the distal portion of the catheter. The valve allows the user to deliver fluid into the patient's body therethrough, but depending on the fluid pressure, also allows the user to flush the entire catheter (i.e., the valve stays closed). In one example, the valve comprises a slit valve (e.g., Groshong type slit valve, etc.). The catheter may comprise one or more slit valves positioned on distal portion of the catheter.

Figure 86:
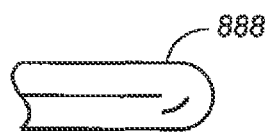
FIG. 86 illustrates one variation of the loop-tip catheter of FIG. 85. In this variation, the loop portion is configured such that there is no center opening through the distal portion of the catheter where the tubing loops back on itself.

To utilize the catheter for infusion, the user may seal off one lumen opening while injecting fluid into another lumen opening. The pressure built up inside the catheter overcomes the resistance of the slit valve and forces the fluid inside the lumen to exit into the patient's body through the valve. To flush the catheter, saline or other fluids (e.g., heparin solution, etc.) can be injected into one lumen opening while leaving the other lumen open. The fluid travels down one lumen and back up the second lumen and exits at the catheter at the proximal end. This self-flushing feature allows the user to flush the catheter while preventing the flushing fluids from entering the patient's body. FIG. 86 illustrates another variation of the loop-tip 888 where the fluid channel is configured to loop back at the distal end of the catheter. However, in this configuration, the catheter is configured without a physical opening between the distal looped portions of the catheter. One of ordinary skill in the art having the benefit of this disclosure would appreciate that the self-flushing feature may also be implemented on catheters with three or more lumens. For example, a triple lumen catheter is configured, such that fluid injected through a first lumen can loop back through the second and the third lumen, and exit at the proximal end of the catheter.

Figure 87:
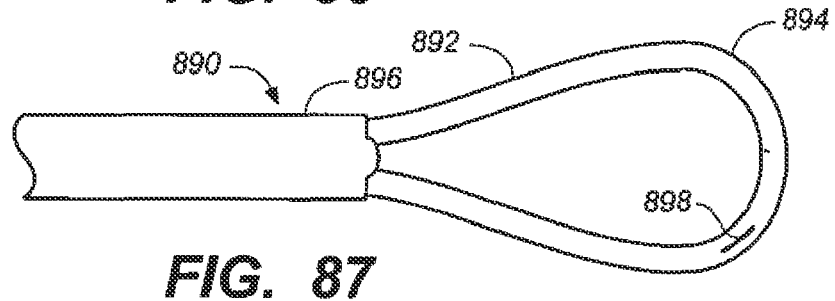
FIG. 87 illustrates another variation of a loop-tip catheter comprising a single continuous tubing looped back on itself to form the loop structure, the proximal portion of the overlaid tubing being covered by a sheath.

FIG. 87 illustrates another variation, where the loop-tip catheter 890 comprises a silicone tube 892 folded onto itself to form the loop 894. A polyurethane sheath 896 is the placed over the proximal overlapping portion of the silicone tube 892 to bind the two segments of the tube together. A slit 898 is then cut into the loop portion 894 of the silicone tube 892 to form the slit valve.

Figure 88A:
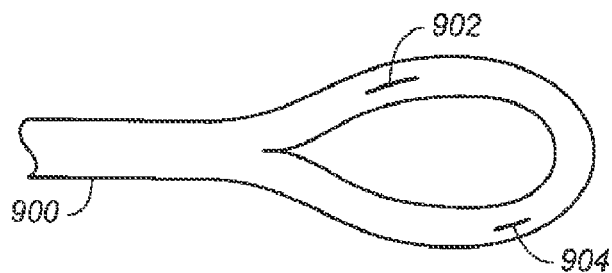
FIG. 88A illustrates another variation of a loop-tip catheter comprising a dual lumen catheter shaft with bifurcating branches extending distally at the distal end of the catheter shaft to form a loop at the distal end. A plurality of slit valves are implemented along the length of the loop.
Figure 88B:
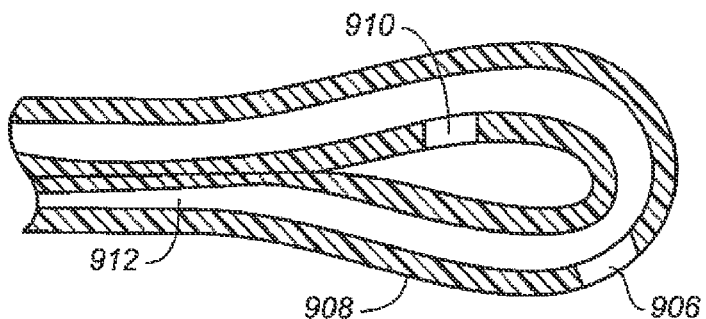

FIG. 88A illustrates another variation, where the loop-tip catheter 900 comprises a homogenous material. Two or more slit valves 902, 904 are placed on the loop section of the catheter. In certain applications, it may be beneficial to place a slit valve on an inner surface of the loop. FIG. 88B shows one example where a first slit valve 906 is positioned on the outer circumferential surface of the loop, while a second valve is place on the inner circumferential surface of the loop 908. In this example, a single lumen 912 extends from the proximal end to the distal end and loops back through the loop 908.

Figure 88C:
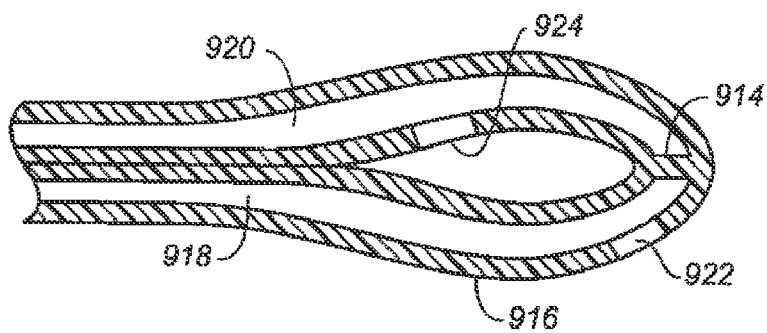

FIG. 88C illustrates another variation where a seal 914 is created within the loop 916 to separate the lumen into two separate channels. In one example, the seal 914 or separation is implemented with a septum or divider. The catheter is configured with venous lumen 918 and a slit valve positioned at the distal end of the catheter to serve as the venous outlet 922; a slit valve 924 positioned on the inner surface of the loop is configured to serve as the arterial inlet for accessing the arterial lumen 920.

Figure 89:
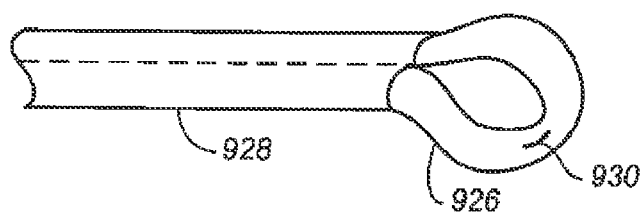
Figure 90:
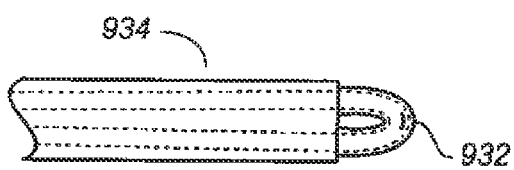

In another variation, a short silicone tube 926 is inserted into the distal end of a dual lumen polyurethane catheter 928 to form a loop-tip catheter, as shown in FIG. 89. A slit valve 930 can be implemented on the silicone tube 926. The looped silicone tube may minimize trauma to the vessel when the catheter is being advanced within the catheter. In addition, slit valves that are placed on the silicone tube may perform better than slit valves that are placed on tubing with higher durometers. FIG. 90 illustrates another example of a silicone tube 932 connected to the distal end of an elongated catheter 934, which comprises a material with a higher durometer than the silicone tube. The silicone tube can be anchored into the elongated catheter's shaft using a braid, wire extension, or other methods that are well known to one of ordinary skill in the art.

Figure 91:
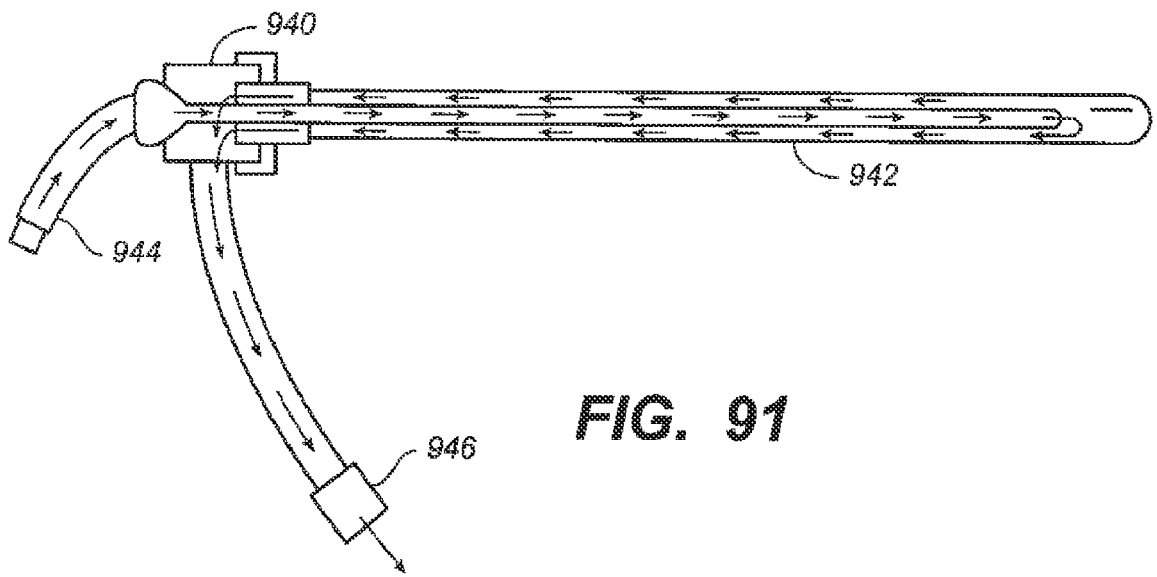

As discussed above, the loop-tip catheters shown in FIGS. 85-87 permit self flushing without the need for the flushing fluid to enter into the body. FIG. 91 illustrates fluids being infused into a catheter through the adaptor 940 to flush out the lumen of the catheter 942. In this example, a dual lumen coaxial Groshong catheter is implemented with a proximal interface for connection to the adaptor 940. The flushing liquid is directed into a first port 944 of the adaptor, and travels down a first lumen (i.e., center lumen) in the catheter 942 to the distal end of the catheter. Once the fluid reaches the distal end of the catheter, it travels back towards the proximal end of the catheter through a second lumen (i.e., outer coaxial lumen). Eventually, the fluid flows out of the adaptor through an exit port 946. In other applications, the catheter may also be adapted to support infusion of fluids at a high flow rate at low pressure. For example, conveying attachment 948, as shown in FIG. 92A, allows the user to inject fluids into both lumens 950, 952 simultaneously. To flush the catheter, the conveying attachment is removed and fluids are flushed down one lumen, while flush fluids are collected from the extension leg connected to the second lumen.

In another variation a bridge 954 is provided between the two hubs 956, 958, as shown in FIG. 92B. A valve 960 is provided on the bridge 954 to control fluid flow through the bridge 954. To infuse through both lumens, one of the extension hubs is capped 962, and fluid is infused through a second hub while keeping the valve 960 open. To flush the catheter, the valve 960 is closed to terminate fluid flow through the bridge 954. With the cap 962 removed, flushing solution is infused through one extension port 956 and then collected from the second extension port 958. In yet another variation, a clamp 964 is positioned over a first extension leg 966 which is in fluid communication with one of the two lumens. A second extension leg 970 connected to the second lumen is used to infuse fluid into the catheter 972. When the clamp is closed, the catheter functions as a fluid delivery device. The clamp 964 can be opened to permit flushing of the catheter. When the catheter is flushed using the technique described above, if the user's desire to prevent the flushing fluid from entering the patient's circulatory system, it may be desirable to keep the flushing pressure below the valve open pressure. In another approach for flushing the catheter, the opening on one of the extension legs of the catheter is placed within a flushing solution, while suction is applied to the other extension leg to aspirate flushing fluid through the catheter.

In yet another variation, a dual septa port 980 is utilized with a self-flushable catheter 982, as shown in FIG. 93. This configuration allows the user to implant the complete assembly under the skin, while still allowing the user to flush the catheter by infusion and extracting the flushing solution through the two septa 984, 986. Optionally, a valve 988, which is accessible with a needle instrument, is positioned between the two chambers in the port to control fluid communication between the two chambers. The valve can be opened to improve flow rate when medication is to be infused into the patient's body. To flush the catheter, the valve is closed to allow the user to infuse flushing solution into one chamber and remove the flushed solution out of the adjacent chamber.

In another aspect of the invention, a multi-lumen catheter is configured with a loop at the distal end to serve as an interface for engaging other instrumentations. In one variation, the catheter comprises a dual lumen catheter 990 with a loop 992 at the distal tip of the catheter, as shown in FIG. 94A. The catheter may be further configured with a lumen opening 994 position on the top side of the catheter for accessing a first lumen 998, while the second lumen opening 996 is positioned on the under side of the catheter, proximal of the first opening 994, for accessing the second lumen 1000, as shown in FIG. 94B. In one example, the loop-tip catheter of FIG. 94 is configured from a D-shaped tubing 1002 as shown in FIG. 95. At the midpoint 1004 of the tubing, two openings 1006, 1008 are cut into the top and bottom sides of the tubing. An extended opening 1010 is cut on the top side, proximal to the midpoint, to form the opening into the first lumen of the catheter. A second extended opening 1012 is cut on the bottom side, distal to the midpoint, to form the opening into the second catheter lumen. By varying the locations of the openings along the length of the catheter, one can configure a catheter with different flow characteristics. The tubing 1002 is then folded in half along the midpoint 1004. Supporting mandrels are then inserted into the two lumens, and the two folded sections are bonded together in a heat or solvent process. The distal loop provides an interface to allow the user to easily connect an instrument to the tip of the catheter. For example, a tunneler with a hook can latch onto the tip of the catheter. This particular design provides an atraumatic tip with an interface for coupling the tip of the catheter to another medical instrument.

In another variation, a through hole 1014 is established through the distal end of the catheter 1016 entering into one of the lumens, as shown in FIG. 96, to allow over-the-guidewire placement of the catheter. In another variation, the lumen openings are configured as slit valves 1018, 1020, such that the openings can stay closed when the catheter is not being utilized for fluid infusion and/or aspiration, as shown in FIG. 97.

FIG. 98 illustrates another aspect of the invention where the proximal end of a dual lumen catheter 1022 is bifurcated 1024, and the proximal tips of the two bifurcating branches 1026, 1028 are connected to each other to form a loop 1030 at the proximal end of the catheter. The proximal loop design may be utilized with catheters of various dimensions and different tip configurations. The proximal loop design may be helpful for reverse tunneling of the catheter after the distal end of the catheter has been implanted. Various medical instruments can be easily connected to the loop structure. The proximal loop may also minimize contamination of the catheter lumen and prevent air from entering the proximal end of the catheter. In addition, the proximal loop can prevent bodily fluid from exiting the proximal end of the catheter, and air from entering the proximal end of the catheter. The proximal loop may also allow the user to pre-load the catheter with fluid before implantation. Saline injected into one distal opening on the catheter travels through the proximal loop, and pushes out any air in the catheter lumen. Once the catheter is implanted, the user can simply cut the loop and connect luer fittings onto the proximal ends of the bifurcating branches.

In another aspect of the invention, a latching mechanism 1032, which can be secured to a distal or proximal catheter loop 1034, is provided for attaching the catheter to medical instrumentation. For example, the latching mechanism can be a Velcro strap 1032 that can be placed around the catheter loop 1034, as shown in FIG. 99. An interface 1036 is provided on the strap for connection to a tunneler. FIG. 100 illustrates another method for engaging a loop on the catheter. A tunneler 1038 with a hook 1040 is latched onto the loop 1042 of the catheter 1044, and a protective sleeve 1046 is slid over the interface to secure the connection, and to prevent the catheter 1044 from accidentally sliding off the hook. FIG. 101 shows another design, where a fastener 1048 is placed around the loop 1050 on a catheter 1052. A ring 1054 coupled to the fastener 1048 allows the user to hook a tunneler 1056 onto the fastener 1048. FIG. 102 illustrates the use of strings 1058 to connect a tunneler 1060 to the catheter loop 1062. A string or threads, which have been looped through the catheter loop, can be coupled onto hooks or indented profiles on a tunneler. The catheter can then be used to tunnel the catheter. FIG. 103 illustrates one variation of an adaptor clip 1064. The adaptor clip can be latched around the catheter loop. An interface 1066 (e.g., ring, etc) connected to the adaptor clip 1064 may then be utilized for connection to a medical instrument. In another variation, a through hole 1068 is placed into distal portion of the catheter 1070 to provide a medium for connecting to a medical instrument. In one example, as shown in FIG. 104, a through hole 1068 is placed through the proximal portion of a double-D tube 1070. A hook or threads may than be inserted through the through hole to engage the proximal end of the catheter.

In another aspect of the invention, the loop-tip catheter comprises a loop positioned on the mid-shaft at the distal section of the catheter. One of the catheter lumens may be configured to open distally into the center of the loop structure. In an exemplary approach, the catheter is configured by cutting a slit 1080 through the mid-shaft 1082 of a double D tube 1084, as shown in FIG. 105. The tube is then partitioned at the slit to form a loop. If the slit is cut right above the septum 1090, access to the top lumen becomes readily available. Additional side wall sections of the upper loop 1086 may be removed to enlarge the loop and increase access to the top lumen 1088. If the slit 1080 is placed within the septum 1090, the inner face of the upper loop 1086 may be removed to provide an access port to the upper lumen 1088. The shape of the loop 1090 is then thermoformed to stabilize the loop structure. The distal tip portion 1092 of the catheter can be modified through RF welding or thermoformed, to fuse the septum to one side of the tubing to create a single channel for accessing the lower lumen 1094. As shown in FIG. 106, the upper lumen 1088 opens in the distal direction right into the center 1096 of the loop structure 1090. The lower lumen 1094 opens distally at the distal tip 1098 of the catheter. In one application, the catheter is utilized for hemodialysis, with the upper lumen serving as the arterial lumen, and the lower lumen serving as the venous lumen.

FIG. 107 illustrates another variation of a catheter that can resist sidewall suction, and also allow over the wire placement and exchange. In one design, a slit 1100 is cut into the septum of a double D catheter 1102. However, the slit does not penetrate through the entire cross-section of the septum. The slotted section is flared open 1104, as shown in FIG. 107. The operator may modify the angle of the flared section 1106 to meet particular design needs. The distal flare portion of the catheter can then be set in place through thermoformation or other methods that are well known to one of ordinary skill in the art. Additional materials, such as metallic or polymeric inserts, may be provided to reinforce the flared structure. Once the flare segment is set in place, the operator may remove segments of the lumen walls to modify the location of the lumen exits. For example, distal segment 1108 of one of the lumen wall 1110 may be removed to form a lumen opening 1112 that is proximally positioned from the distal tip 1114 of the catheter, as shown in FIG. 108. One or more orifices 1116, 1118 are then placed on the partitioned septum surfaces 1120, 1122, as shown in FIG. 109, to provide additional access ports to one or both lumens 1124, 1126. Since these additional orifices are located on the septum wall within the flare section, they are less prone to obstruction from the side wall of the vessel. In a design variation, the proximal lumen opening is sealed, and a large side hole is created in the flare segment on the septum surface for accessing the proximal lumen. To facilitate the placement of the catheter, the flared sections can be compressed together for sheath placement and over-the-guidewire placement.

In another design, the flared section 1130 is created at the mid-shaft of the catheter 1132 instead of the distal end 1134, as shown in FIG. 110A. An orifice 1136 is created on one of the septum walls 1138 in the flared section 1130 to serve as the inlet to the arterial lumen, as shown in FIG. 110A. The distal tip portion of the catheter is RF welded to fuse the septum against inner wall of the arterial lumen, and to form a single channel for accessing the venous lumen. At the proximal shaft, one lumen serves as the arterial lumen 1140 and one lumen serves as the venous lumen 1142, as shown in FIG. 110B. The arterial lumen 1140 aspirates fluid from the inlet 1136 positioned in the flared section, and the venous lumen 1142 directs fluids to flow through the flared section into the distal tip portion of the catheter, as shown in FIG. 110C. The infused fluids in the venous lumen then exit the distal tip of the catheter through the venous outlet 1144.

In another design variation, two slits 1146, 1147, are placed onto a dual lumen catheter to form two flared openings 1150, 1151, for accessing the two lumens 1148, 1149 in the catheter, as shown in FIGS. 111A and 111B. In one variation, the two flared openings are positioned side by side, to form an axially symmetric catheter as shown in FIG. 111B. In another variation, the two flared openings are staggered along the length of the catheter. An optional distal opening 1153 may be implemented to provide an additional access port for one of the lumens. The distal opening may allow over-the-guidewire placement of the catheter. As shown in FIG. 111A, a distal opening can be provided for accessing the lower lumen 1149. It is also contemplated that the distal end of the catheter may be sealed and configured with an atraumatic tip profile. In yet another variation, the dual lumen catheter is provided with one flared opening, such that the upper lumen of the catheter opens into the flared opening, while the lower lumen passes through the flared section and exit at the distal end of the catheter. As discussed earlier, the flared sections can be compressed together for sheath placement and/or over-the-guidewire placement.

FIGS. 112A-112B illustrate another variation where a portion of the flared section is reserved (e.g., re-sealed) for later use. A catheter 1152 with a flared segment 1154 with an elongated opening 1156 for accessing the arterial lumen is created first (FIG. 113). Then the proximal portion 1158 of the flared segment 1154 is sealed to form a catheter with a shortened flared segment (FIG. 114). This catheter with the shortened flared segment, as shown in FIG. 112A, is then implanted within the patient. Overtime, tissue growth or clot formation may block opening(s) within the shortened flared segment. The user may then extend the flared segment by exposing reserved proximal flared segment 1160, as shown in FIG. 112B. In one variation, the flared segment is extended with the introduction of a mandrel or other instruments. In another variation, a balloon catheter is introduced and inflated in the arterial lumen of the catheter to open the reserved section of the flared segment.

In yet another aspect of the invention, a multi-lumen catheter comprising a raised profile on the inner walls of the catheter lumen is provided to prevent aspiration collapse of the catheter lumen. In one variation, the septum in the catheter is modified with a contoured profile to prevent aspiration collapse. The catheter may further comprise a flexible or pliable septum to allow the expansion of one of the lumens within the catheter, to permit power (i.e., high flow rate) injection.

FIG. 115A illustrates one variation where raised surface profiles 1170, 1172 (e.g., ridges, bumps, protrusions, etc.) are provided on the inner walls 1174, 1176 of a dual lumen 1182, 1184 catheter 1180 to prevent complete collapse of the catheter lumens. The raised profile can support the septum 1178 and prevent the septum from collapsing against the wall of the catheter when a large suction is applied to the lumen of the catheter. The raised profile may also be used maintain the patency of the catheter when an adjacent catheter is experiencing high pressure due to power injection in the adjacent lumen. As power injection is applied to one lumen, the septum expands toward the catheter wall of the adjacent lumen. The raised surface profile on the catheter wall within the second lumen prevents the septum from completely collapsing against the catheter wall, thus allowing the user to continue to utilize the second lumen for infusion or aspiration. In another variation, the septum comprises flexible or pliable material, such that when power injection is applied to a first lumen within the catheter, the lumen can expand and increase the cross-sectional area of first lumen to decrease resistance and permit higher flow rate. The raised surface profile within the adjacent lumen prevents the flexible septum from completely collapsing against the catheter wall, and permits fluids to be infused or aspirated through the adjacent lumen. A raised profile may also be provided within the first lumen, so that when suction is utilized in the first lumen to aspirate fluids, the flexible septum is prevented from completely collapsing against the wall of the catheter.

In one exemplary application, a dual lumen catheter is configured with a septum that has a lower durometer than the circumferential wall of the catheter. A raised surface profile is provided on the inner catheter wall of one of the two lumens. The raised surface profile may extend along the length of the catheter from the proximal end of the catheter to the distal end of the catheter. Optionally, raised surface profiles are provided within both of the catheter lumens.

FIG. 115B shows another variation where the raised surface profiles 1186, 1188 are provided next to the septum 1190 of the catheter 1192. FIG. 115C illustrates another variation, where raised surface profiles 1194, 1196, 1198, 1200 are provided on both sides of the septum 1202 to support the septum. As shown in this figure, the septum may further comprise a flexible material, such that during high flow rate infusion, the infused lumen may expand towards the adjacent lumen to allow a larger throughput of fluids. FIG. 115D illustrates another variation where the raised profiles 1204, 1206 are provided on the septum 1208. Using raised profiles on the septum wall and/or the circumferential surface of the catheter inner wall, one is able to create a catheter with lumens of unequal size, while preventing the smaller lumen from collapsing onto itself. FIG. 115E shows yet another variation where the septum 1210 is configured with a curved profile 1212 to prevent the septum 1210 from completely collapsing against the wall 1214 of the catheter. The septum 1210 may comprise a channel 1216 extending along the length of the septum from the proximal end of the catheter towards the distal end of the catheter. In such a design, when the septum 1210 is forced against the inner wall 1214 of the catheter, a fluid conduit is still provided through the channel 1216 on the septum, as illustrated in FIG. 115E. One of ordinary skill in the art having the benefit of this disclosure would appreciate that variations of raised surface profile and/or the flexible lumen design may also be implemented in catheter with three or more lumens.

This invention has been described and specific examples of the invention have been portrayed. While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well. Finally, all publications and patent applications cited in this specification are herein incorporated by reference in their entirety as if each individual publication or patent application were specifically and individually put forth herein.

What is claimed is:

1. A hemodialysis catheter, comprising an elongate body including an outer wall enclosing an arterial lumen and a venous lumen extending from a proximal end of the body to a distal end thereof, the outer wall extending from the distal end of the body to form a continuous loop beginning at a first side of the distal end of the body and ending at a second side thereof to define an enclosed opening, the loop including an arterial inlet on an interior wall facing the enclosed opening, the arterial inlet in fluid communication with the arterial lumen, the loop further including a venous outlet on an exterior wall, the venous outlet in fluid communication with the venous lumen, the venous outlet positioned distal of the arterial inlet.

2. The hemodialysis catheter according to claim 1, wherein the arterial lumen and venous lumen are separated along the elongate body by a septum.

3. The hemodialysis catheter according to claim 1, one of the arterial inlet and venous outlet comprising a slit valve.

4. The hemodialysis catheter according to claim 3, both of the arterial inlet and venous outlet comprising a slit valve.

5. The hemodialysis catheter according to claim 1, the loop enclosing a lumen including a seal positioned between the arterial inlet and venous outlet.

6. The hemodialysis catheter according to claim 1, further comprising a wire extending through the elongate body, the wire having a distal end coupled to the loop.

7. The hemodialysis catheter according to claim 1, wherein the wire includes a channel extending from a proximal end of the wire to a distal portion of the wire.

8. The hemodialysis catheter according to claim 1, further comprising an atraumatic tip.

9. The hemodialysis catheter according to claim 1, wherein the exterior wall includes a tubular portion extending therefrom, the venous outlet positioned on the tubular portion.

10. The hemodialysis catheter according to claim 1, wherein the loop includes a corrugated section.

* * * * *